United States Patent
Rinn et al.

(10) Patent No.: US 10,920,221 B2
(45) Date of Patent: Feb. 16, 2021

(54) METHODS OF MAKING AND USING GUIDE RNA FOR USE WITH CAS9 SYSTEMS

(71) Applicant: President and Fellows of Harvard College, Cambridge, MA (US)

(72) Inventors: John L. Rinn, Boston, MA (US); David M. Shechner, Arlington, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/571,321

(22) PCT Filed: May 13, 2016

(86) PCT No.: PCT/US2016/032255
§ 371 (c)(1),
(2) Date: Nov. 2, 2017

(87) PCT Pub. No.: WO2016/183402
PCT Pub. Date: Nov. 17, 2016

(65) Prior Publication Data
US 2019/0106693 A1    Apr. 11, 2019

Related U.S. Application Data

(60) Provisional application No. 62/160,829, filed on May 13, 2015.

(51) Int. Cl.
| | | |
|---|---|---|
| C12N 15/63 | (2006.01) | |
| C12N 15/11 | (2006.01) | |
| C07H 1/00 | (2006.01) | |
| C07H 21/02 | (2006.01) | |
| C12N 9/22 | (2006.01) | |
| C12N 15/90 | (2006.01) | |

(52) U.S. Cl.
CPC .............. *C12N 15/11* (2013.01); *C07H 1/00* (2013.01); *C07H 21/02* (2013.01); *C12N 9/22* (2013.01); *C12N 15/63* (2013.01); *C12N 15/907* (2013.01); *C12N 2310/20* (2017.05); *C12N 2740/16043* (2013.01); *C12N 2800/80* (2013.01)

(58) Field of Classification Search
CPC .................................................. C12N 2310/20
See application file for complete search history.

(56) References Cited

U.S. PATENT DOCUMENTS

| | | | |
|---|---|---|---|
| 2014/0068797 A1* | 3/2014 | Doudna | ................. C12N 15/63 800/18 |
| 2015/0071900 A1 | 3/2015 | Liu et al. | |
| 2017/0166912 A1* | 6/2017 | Brower-Toland | ........................... C12N 15/8213 |
| 2017/0226533 A1* | 8/2017 | Frisch | ..................... C12N 9/16 |

OTHER PUBLICATIONS

Konermann et al in "Genome-scale transcriptional activation by an engineered CRISPR-Cas9 complex". (Nature vol. 517, published Jan. 29, 2015, pp. 583-600; IDS reference). (Year: 2015).*
Cuello et al. Transcription of the human U2 snRNA genes continues beyond the 3' box in vivo. EMBO J May 17, 1999 vol. 18 No. 10 pp. 2867-2877.
Konermann et al. Genome-scale transcriptional activation by an engineered CRISPR-Cas9 complex. Nature Jan. 19, 2015 vol. 517 No. 7536 pp. 583-588.
Nissim et al. Multiplexed and programmable regulation of gene networks with an integrated RNA and CRISPR/Cas toolkit in human cells. Molecular Cell May 22, 2014 vol. 54 No. 4 pp. 698-710.

* cited by examiner

*Primary Examiner* — Catherine S Hibbert
(74) *Attorney, Agent, or Firm* — Banner & Witcoff, Ltd.

(57) ABSTRACT

CRISPR/Cas Systems are provided where guide RNAs include one or more selected RNA sequences for delivery to a target nucleic acid sequence.

14 Claims, 47 Drawing Sheets

Specification includes a Sequence Listing.

FIG. 7A
FIG. 7B
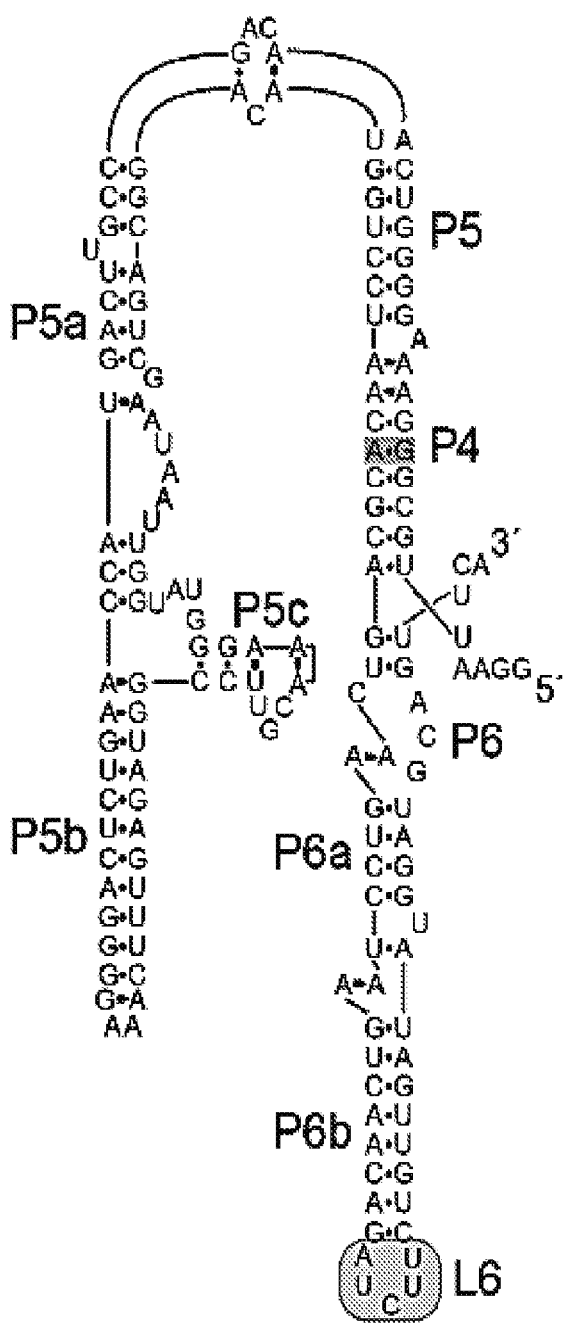
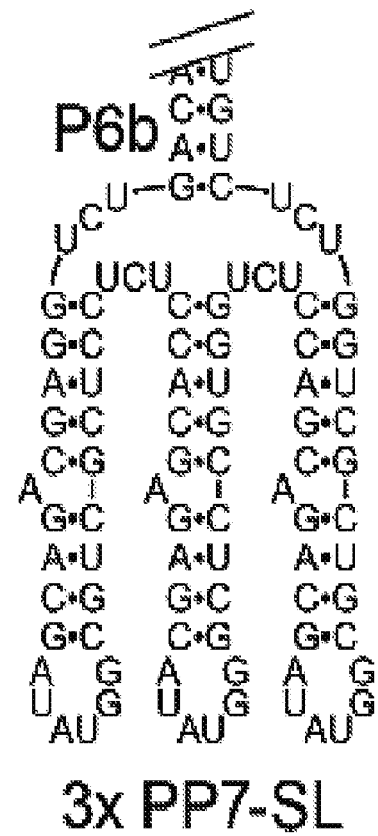
3x PP7-SL

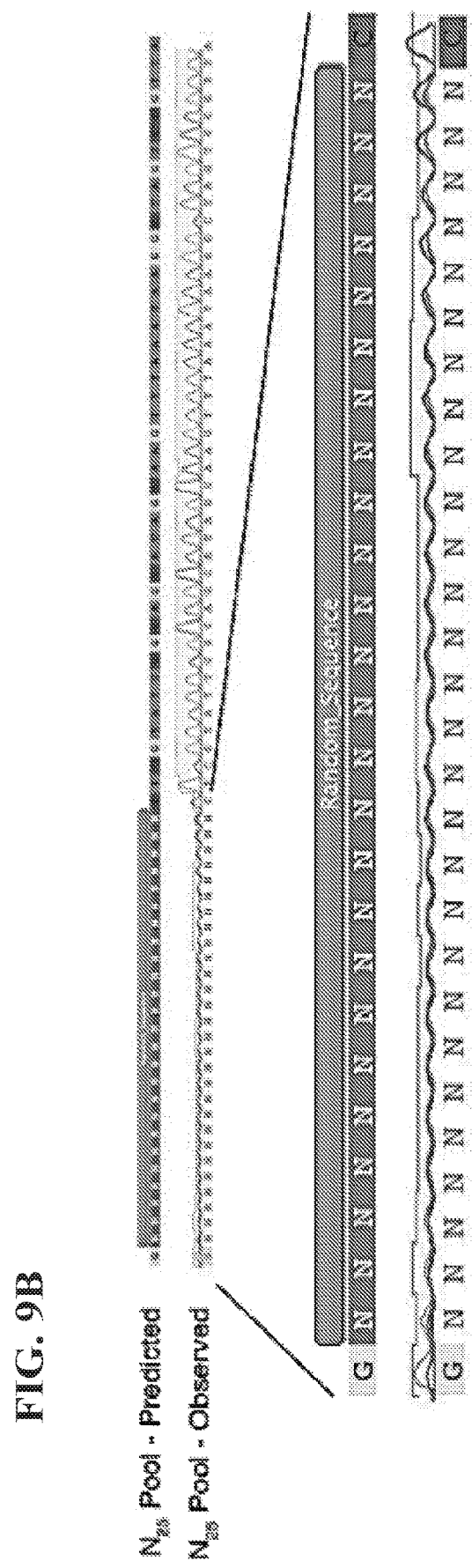

"Spinach2"

"Baby Spinach"

"Bunch of Baby Spinach" (BoBS)

sgRNA Core

METHODS OF MAKING AND USING GUIDE RNA FOR USE WITH CAS9 SYSTEMS

RELATED APPLICATIONS

This application is a National Stage Application under 35 U.S.C. 371 of co-pending PCT application PCT/US16/32255 designating the United States and filed May 13, 2016; which claims the benefit of Provisional application No. 62/160,829 and filed May 13, 2015 each of which are hereby incorporated by reference in their entireties.

STATEMENT OF GOVERNMENT INTERESTS

This invention was made with government support under GM099117, ES020260, and MH102416 awarded by National Institutes of Health. The government has certain rights in the invention.

BACKGROUND

The CRISPR type II system is a recent development that has been efficiently utilized in a broad spectrum of species. See Friedland, A. E., et al., Heritable genome editing in C. elegans via a CRISPR-Cas9 system. Nat Methods, 2013. 10(8): p. 741-3, Mali, P., et al., RNA-guided human genome engineering via Cas9. Science, 2013. 339(6121): p. 823-6, Hwang, W. Y., et al., Efficient genome editing in zebrafish using a CRISPR-Cas system. Nat Biotechnol, 2013, Jiang, W., et al., RNA-guided editing of bacterial genomes using CRISPR-Cas systems. Nat Biotechnol, 2013, Jinek, M., et al., RNA-programmed genome editing in human cells. elife, 2013. 2: p. e00471, Cong, L., et al., Multiplex genome engineering using CRISPR/Cas systems. Science, 2013. 339(6121): p. 819-23, Yin, H., et al., Genome editing with Cas9 in adult mice corrects a disease mutation and phenotype. Nat Biotechnol, 2014. 32(6): p. 551-3. CRISPR is particularly customizable because the active form consists of an invariant Cas9 protein and an easily programmable guide RNA (gRNA). See Jinek, M., et al., A programmable dual-RNA-guided DNA endonuclease in adaptive bacterial immunity. Science, 2012. 337(6096): p. 816-21. Of the various CRISPR orthologs, the *Streptococcus pyogenes* (Sp) CRISPR is the most well-characterized and widely used. The Cas9-gRNA complex first probes DNA for the protospacer-adjacent motif (PAM) sequence (-NGG for Sp Cas9), after which Watson-Crick base-pairing between the gRNA and target DNA proceeds in a ratchet mechanism to form an R-loop. Following formation of a ternary complex of Cas9, gRNA, and target DNA, the Cas9 protein generates two nicks in the target DNA, creating a blunt double-strand break (DSB) that is predominantly repaired by the non-homologous end joining (NHEJ) pathway or, to a lesser extent, template-directed homologous recombination (HR). CRISPR methods are disclosed in U.S. Pat. Nos. 9,023,649 and 8,697,359.

SUMMARY

Aspects of the present disclosure are directed to a method of delivering a selected RNA sequence to a target nucleic acid in a cell including providing to the cell a Cas9 protein and providing to the cell a guide RNA including a spacer sequence and a tracr mate sequence forming a crRNA and a tracr sequence and having a selected RNA domain attached to the guide RNA wherein the guide RNA and the Cas9 protein form a co-localization complex with the target nucleic acid to deliver the selected RNA sequence to the target nucleic acid. According to one aspect, the guide RNA includes a selected RNA sequence attached to the 3' end of the tracr sequence. According to one aspect, the guide RNA includes a selected RNA sequence attached to the 3' end of the tracr sequence and wherein the tracr sequence and the crRNA sequence may be separate or connected by the linker. According to one aspect, the guide RNA includes a selected RNA sequence attached to the 5' end of the spacer sequence. According to one aspect, the guide RNA includes a selected RNA sequence attached to the 5' end of the spacer sequence and wherein the tracr sequence and the crRNA sequence may be separate or connected by the linker. According to one aspect, the crRNA and the tracr sequence of the guide RNA are separate sequences, and wherein the selected RNA sequence is attached to the 5' end of the tracr sequence or the 3' end of the crRNA sequence. According to one aspect, the crRNA and the tracr sequence are connected by a linker sequence and the linker sequence includes the selected RNA sequence. According to one aspect, the Cas9 protein is provided to the cell by introducing into the cell a first foreign nucleic acid encoding the Cas9 protein and wherein the guide RNA is provided to the cell by introducing into the cell a second foreign nucleic acid encoding the guide RNA, wherein the guide RNA and the Cas9 protein are expressed, and wherein the guide RNA and the Cas9 protein co-localize to the target nucleic acid to deliver the selected RNA sequence to the target nucleic acid. According to one aspect, the Cas9 protein is an enzymatically active Cas9 protein, a Cas9 protein nickase or a nuclease null or nuclease deficient Cas9 protein. According to one aspect, the cell is in vitro, in vivo or ex vivo. According to one aspect, the cell is a eukaryotic cell or prokaryotic cell. According to one aspect, the cell is a bacteria cell, a yeast cell, a fungal cell, a mammalian cell, a plant cell or an animal cell. According to one aspect, the selected RNA sequence is between about 10 and about 10,000 nucleotides. According to one aspect, the target nucleic acid is genomic DNA, mitochondrial DNA, plastid DNA, viral DNA, exogenous DNA or cellular RNA. According to one aspect, the selected RNA sequence is an aptamer, a noncoding RNA, a ribozyme, a functional RNA sequence, a pool of random RNA sequences, an RNA scaffold, a naturally occurring lncRNA or a lncRNA subdomain.

According to one aspect, a cell is provided which includes a Cas9 protein and guide RNA including a spacer sequence and a tracr mate sequence forming a crRNA and a tracr sequence and having a selected RNA domain attached to the guide RNA and wherein the guide RNA and the Cas9 protein are members of a co-localization complex for the target nucleic acid. According to one aspect, the cell is a eukaryotic cell or prokaryotic cell. According to one aspect, the cell is a bacteria cell, a yeast cell, a fungal cell, a mammalian cell, a plant cell or an animal cell. According to one aspect, the selected RNA sequence is between about 10 and about 10,000 nucleotides. According to one aspect, the selected RNA sequence is an aptamer, a noncoding RNA, a ribozyme, a functional RNA sequence, a pool of random RNA sequences, an RNA scaffold, an RNA-based sensor or signal processor, an RNA-based signaling device, a naturally occurring lncRNA or a lncRNA subdomain, a synthetic lncRNA, or synthetic lncRNA subdomain.

According to one aspect, a genetically modified cell is provided including a first foreign nucleic acid encoding a Cas9 protein and a second foreign nucleic acid encoding a guide RNA including a spacer sequence and a tracr mate sequence forming a crRNA and a tracr sequence and having a selected RNA domain attached to the guide RNA and wherein the guide RNA and the Cas9 protein are members of a co-localization complex for the target nucleic acid. According to one aspect, the cell is a eukaryotic cell or prokaryotic cell. According to one aspect, the cell is a bacteria cell, a yeast cell, a fungal cell, a mammalian cell, a plant cell or an animal cell. According to one aspect, the selected RNA sequence is between about 10 and about 10,000 nucleotides. According to one aspect, the selected RNA sequence is an aptamer, a noncoding RNA, a ribozyme, a functional RNA sequence, a pool of random RNA sequences, an RNA scaffold, a naturally occurring lnc RNA or a lnc subdomain.

According to one aspect, a method of making a guide RNA including a selected RNA sequence is provided including constructing a nucleic acid sequence including a first nucleic acid sequence encoding a guide RNA having a spacer sequence, a tracr mate sequence and a tracr sequence, wherein the tracr mate sequence and the tracr sequence are optionally connected by a linker sequence, and wherein the selected RNA sequence is fused to the 3' end of the tracr sequence, the 5' end of the spacer sequence, the 5' end of the tracr sequence if present, or the selected RNA sequence is fused to the linker sequence if present, or the selected RNA sequence is the linker sequence and wherein the selected nucleic acid sequence includes from 10 to 10,000 nucleotides, and a Pol II promoter sequence and a Pol II terminator sequence, and introducing the nucleic acid sequence into a cell, and expressing the nucleic acid sequence to produce the guide RNA including the selected RNA sequence. According to one aspect, the Pol II promoter sequence is CMVPro or U1Pro and the Pol II terminator sequence is U1 3'Box, MASC or U2 smBox/U1 3'Box. According to one aspect, the cell is in vitro, in vivo or ex vivo. According to one aspect, the cell is a eukaryotic cell or prokaryotic cell. According to one aspect, the cell is a bacteria cell, a fungal cell, a yeast cell, a mammalian cell, a plant cell or an animal cell. According to one aspect, the selected RNA sequence is between about 20 and about 5,000 nucleotides.

Further features and advantages of certain embodiments of the present invention will become more fully apparent in the following description of embodiments and drawings thereof, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present embodiments will be more fully understood from the following detailed description of illustrative embodiments taken in conjunction with the accompanying drawings in which:

FIG. 1A depicts a schematic of a general, targeted ncRNA localization system: a ncRNA cargo (and potential associated proteins) is ectopically targeted to a DNA locus via a programmable protein conduit. FIG. 1B (SEQ ID NO:1-2) depicts an overview of DNA targeting by S. pyogenes dCas9, directed by a minimal sgRNA that targets the GLuc reporter. See Chen, B. et al. Dynamic imaging of genomic loci in living human cells by an optimized CRISPR/Cas system. Cell 155, 1479-1491 (2013) hereby incorporated by reference in its entirety. FIG. 1C depicts expression constructs in the dual reporter transcription activation system. Target and non-target sites in the Reporter and Normalizer are absent from the human genome and are multimerized to exploit the additivity of artificial transcription activators. See Mali, P. et al. CAS9 transcriptional activators for target specificity screening and paired nickases for cooperative genome engineering. Nature biotechnology 31, 833-838 (2013); Maeder, M. L. et al. CRISPR RNA-guided activation of endogenous human genes. Nature methods 10, 977-979 (2013); Perez-Pinera, P. et al. RNA-guided gene activation by CRISPR-Cas9-based transcription factors. Nature methods 10, 973-976 (2013) each of which are hereby incorporated by reference in their entireties. See also, Chavez, et al., (2015) Highly efficient Cas9-mediated transcriptional programming. Nature Methods, doi:10.1038/nmeth.3312 hereby incorporated by reference in its entirety. minCMV: a 60 nt minimal cytomegalovirus promoter; 2A: a 2A "self-cleaving" peptide. Lentiviral variants are shown; in transient reporter assays, regions bracketed by asterisks are removed. CRISPR construct design is modeled after that provided in Chen, B. et al. Dynamic imaging of genomic loci in living human cells by an optimized CRISPR/Cas system. Cell 155, 1479-1491 (2013). FIGS. 1D-1F are directed to reporter system visualization of locus-specific RNA-guided transcription activation, in HEK293FT cells. FIG. 1D depicts live cell fluorescence microscopy, using transient reporters. All images are 10× magnification. FIG. 1E depicts FACS analysis of the same experiment. Cells were gated with an mCherry co-transfection control (data not shown). The percentages of Venus and mCerulean positive cells (mean, ±standard deviation; n=3) are quoted. FIG. 1F depicts luciferase assays. Values are means±standard deviation, n=3.

FIG. 2A depicts design of "TOP" topology constructs. Accessory RNA domains are detailed in FIG. 7 All RNA constructs are expressed from a human U6 promoter (see FIG. 1C). FIG. 2B depicts schematics summarizing direct activation (dCas9~VP, left) and bridged activation (dCas9/PP7~VP, right) assays. FIG. 2C depicts luciferase reporter assays of the five topology constructs. Values are means±standard deviation; n=3. Student's one-tailed t-test, relative to negative controls (far left). FIG. 2D depicts FACS analyses on transient reporter assays. Means±standard deviation; n=3. FIG. 2E depicts RIP/qRT-PCR of dCas9•TOP1 and dCas9•TOP2. qPCR primers target the core sgRNA and the accessory domain (p1 and p2, respectively, right. Values are means±standard deviation. n=4., Student's one-tailed t-test. FIG. 2F depicts results of targeting large RNAs to endogenous loci, ASCL1, IL1RN, NTF3, TTN. GLuc activation was measured by luciferase assays; activation of all endogenous loci was measured using qRT-PCR. Values are means±standard deviation. n=4, Student's one-tailed t-test, relative to dCasVP alone negative control. NTF3-targeting constructs were mixed pools of four gRNAs.

FIG. 3A depicts Pol II expression systems for modified sgRNA constructs. EF1α and CMV, the human EF1α promoter and Cytomegalovirus (CMV) immediate-early promoter/enhancer, respectively. EF1α includes two short (33, 5 nt) exons flanking a 943 nt intron. SV40 pA, the SV40 early polyadenylation signal; U1 3' Box, the human U1 snRNA transcription termination motif. See Cuello, P., Boyd, D. C., Dye, M. J., Proudfoot, N. J. & Murphy, S.

Transcription of the human U2 snRNA genes continues beyond the 3' box in vivo. *The EMBO journal* 18, 2867-2877 (1999) hereby incorporated by reference in its entirety. FIG. 3B depicts direct activation by Pol II-driven TOP constructs, measured via luciferase reporter assays. Values are means±standard deviation. n=3, Student's one-tailed t-test, relative to negative controls (far left). "sg," minimal sgRNA. FIG. 3C-FIG. 3E are directed to Pol II expression restoring function to the TOP2 accessory domain. FIG. 3C depicts direct and bridged activation by the most effective constructs, using the CMV/3' Box system. Transient reporter assays are shown. Values are means±standard deviation, n=3; "sg," minimal sgRNA, driven from a U6 promoter. FIG. 3D depicts FACS analyses on transient reporter assays with CMV/3'Box constructs, as in FIGS. 1E and 2D. Data for the sgRNA controls are the same as in FIG. 2D. Values are the means±standard deviation. n=3. FIG. 3E depicts RIP/qRT-PCR of dCas9 complexed with CMV/3'-Box TOP1 or TOP2, as in FIG. 2E.

FIG. 4A depicts Left: Design of "Double TOP" constructs. Accessory domains are detailed in FIG. 7A-FIG. 7D; each P4-P6 domain is separated by a 25 nt unstructured linker, to produce 650 nt accessory domains. Right: Direct activation luciferase assays. Values are means±standard deviation. n=3, Student's one-tailed t-test, relative to negative controls (far left). Long ncRNAs were expressed from the CMV/3'Box backbone. FIG. 4B-FIG. 4C are directed to "Double TOP" constructs that retain intact accessory domains in CRISP/Cas complexes. FIG. 4B depicts direct and bridged activation assays, using transient reporters and Double TOP constructs. Error bars, means±standard deviation. n=3, Student's one-tailed t-test, relative to negative controls (far left). Long ncRNAs were expressed from the CMV/3'Box backbone. FIG. 4C depicts RIP/qRT-PCR of dCas9•Double TOP1 and dCas9•Double TOP2. Immunopurified RNA was analyzed by qPCR primers targeted sgRNA core, or spanned the two P4-P6 monomers in the accessory domain (p1 and p3, respectively, right. Values are means±standard deviation. n=4.

FIG. 4D is directed to sgRNAs appended with a battery of lncRNA domains that form functional complexes with dCas9~VP. Direct activation assays using (top) transient and (bottom) integrated reporters are shown. The minimal TIP5-binding NoRC-associated RNA stem ("pRNA") was displayed internally, as in INT; all other domains were appended on the sgRNA 3' terminus, as in TOP1. RNA constructs were expressed using the CMV/MASC system. Error bars, means±standard deviation. n=3, Student's one-tailed t-test, relative to negative control cells expressing dCas9~VP alone (far left). FIG. 4E depicts RIP/qRT-PCR of dCas9, complexed with a battery of lncRNA domains appended on the sgRNA scaffold. Immunopurified RNA was analyzed using qPCR primers targeting the sgRNA core (p1), or with sets of gene specific primers targeting intervals along the length the lncRNA domain (GSP1-GSP5). Above each primer set, the maximum distance between the qPCR amplicon and sgRNA core domain is indicated. Values are means±standard deviation. n=4. FIG. 4F is a graph of data from transient reporter assays with CRISP-Disp lncRNA constructs, grouped into putative repressors (middle) and activators (right). Values quoted are average (GLuc/CLuc), normalized relative to those of control cells expressing each sgRNA-lncRNA fusion alone. For comparison, bridged repression with U6-driven INT, complexed with dCas9 and PP7~SID is shown (left, light blue). Error bars, means±standard deviation. n=3, Student's one-tailed t-test, relative to negative control (far left) *, p<0.05. None of the constructs tested—including INT•SID—perturbed the activity of integrated reporters (not shown).

FIG. 5A depicts INT insert size having a modest effect on CRISP/Cas efficacy. Direct and bridged activation luciferase assays with constructs bearing internal cartridges of one, three or five PP7 stem-loops (insert lengths listed in red). FIG. 5B depicts functional INT inserts that can be large and structurally discontinuous with the sgRNA core. FIG. 5C (SEQ ID NO:3) depicts assembly of functional guide RNA having with an internal sequence inserted at the linker where function is independent of the sequence and structure near the insertion point. Direct activation assays with a mixed pool of ~1.2×10$^6$ unique INT-N$_{25}$ variants (see FIG. 9A-FIG. 9D). FIG. 5D depicts dCas9 binding to nearly all expressed INT-N$_{25}$ variants. See also FIG. 10A-FIG. 10C. FIG. 5E depicts assembling functional guide RNA bearing a wide assortment of natural and artificial RNA domains. Left: schematics depicting the INT constructs tested; insert lengths are listed below each in red. 51, an artificial streptavidin aptamer (see Walker, S. C., Good, P. D., Gipson, T. A. & Engelke, D. R. The dual use of RNA aptamer sequences for affinity purification and localization studies of RNAs and RNA-protein complexes. *Methods in molecular biology* 714, 423-444 (2011) hereby incorporated by reference in its entirety); MS2 SL, cognate stem-loop for the MS2 phage coat protein (see Chao, J. A., Patskovsky, Y., Almo, S. C. & Singer, R. H. Structural basis for the coevolution of a viral RNA-protein complex. *Nature structural & molecular biology* 15, 103-105 (2008) hereby incorporated by reference in its entirety); Csy4 SL, cognate stem-loop for the *P. aeruginosa* Csy4 protein (see Sternberg, S. H., Haurwitz, R. E. & Doudna, J. A. Mechanism of substrate selection by a highly specific CRISPR endoribonuclease. *Rna* 18, 661-672 (2012) hereby incorporated by reference in its entirety); GFP aptamer as in (see Tome, J. M. et al. Comprehensive analysis of RNA-protein interactions by high-throughput sequencing-RNA affinity profiling. *Nature methods* 11, 683-688 (2014) hereby incorporated by reference in its entirety); Spinach2, a small-molecule-binding fluorescent aptamer see (Song, W., Strack, R. L., Svensen, N. & Jaffrey, S. R. Plug-and-play fluorophores extend the spectral properties of Spinach. *Journal of the American Chemical Society* 136, 1198-1201 (2014) hereby incorporated by reference in its entirety; K-T, a cognate kink-turn for the *A. fulgidus* L7Ae protein (see Saito, H. et al. Synthetic translational regulation by an L7Ae-kink-turn RNP switch. *Nature chemical biology* 6, 71-78 (2010) hereby incorporated by reference in its entirety); BoBS, "Bunch of Baby Spinach," (see FIG. 11A-FIG. 11B). Right: direct activation activities of these constructs, sorted by insert length. Luciferase values are means±standard deviation. n=3. Student's one-tailed t-test, relative to a dCas9~VP alone negative controls. All RNA constructs were expressed from a human U6 promoter; insert sequences are listed in Table 5.

FIG. 6A depicts guide RNA design with selected RNA sequences enabling orthogonality. RNA constructs are as defined in FIG. 5E and Table 5; bridged activation assays employed L7Ae~VP, MS2~VP or PP7~VP. Values are means±standard deviation, n=3. Y-axes for "no RNA" and "3× K-T" data are different. FIG. 6B depicts performing distinct functions at multiple loci using a shared pool of dCas9. sgRNAs or INT derivatives bearing cassettes of PP7 and MS2 stem-loops ("INT-PP7," "INT-MS2") targeting GLuc and NTF3 were simultaneously coexpressed in direct and bridged activation assays. Left: direct activation. Middle: bridged activation with PP7~VP. Right: bridged activation with MS2~VP. Bottom: schematic summarizing the results. GLuc activation was measured by luciferase assays, NTF3 values by qRT-PCR; each is the mean±standard deviation, n=4. FIG. 6C depicts guide RNA allowing locus-specific targeting of novel RNA-based functions and aptamer-based imaging of DNA loci. Top: schematic of the experimental design. Telomere-targeting gRNA is described in Chen, B. et al. Dynamic imaging of genomic loci in living human cells by an optimized CRISPR/Cas system. *Cell* 155, 1479-1491 (2013) (see Table 2). Middle and Bottom: Confocal fluorescence images, at 63× magnification. Middle: in the absence of dCas9. Bottom: in the presence of dCas9. The GLuc-targeting construct targets a site absent in the human genome (see Table 1). See also FIG. 12. FIG. 6D depicts several strategies for guide RNA design based on the present disclosure. Multiple functions can be targeted to discrete sets of loci simultaneously.

FIG. 7A-FIG. 7D (SEQ ID NO:4-7) are directed to secondary structures of TOP1-4 and Double TOP0-2 accessory domains. FIG. 7A depicts the secondary structure of the thermostable ΔC209 mutant of the *T. thermophila* group I intron P4-P6 domain, from which the accessory domains of TOP1-4, and their Double TOP analogs, were derived. Base pairing geometries are indicated using Leontis and Westhof nomenclature; the Watson-Crick G•A base pair introduced by the ΔC209 mutation is highlighted in blue. PP7-SL and MS2-SL cassettes were grafted into L6, boxed in gray. FIG. 7B depicts secondary structure of the 3×PP7 cassette used in U6-driven TOP1-4. The identical cassette comprises the accessory domain of INT P4-P6[3×PP7-SL] (see FIG. 5B and FIG. 5E). FIG. 7C depicts secondary structure of the 5×PP7 cassette used in Double TOP0-2. FIG. 7D depicts secondary structure of the 5×MS2 cassette used in Double TOP0-2.

FIG. 8A is a graph depicting that the majority of CMV/3'Box transcripts are non-polyadenylated. Whole cell RNA was isolated from HEK293FT cells expressing TOP1-4 from CMV/SV40 pA or CMV/3'Box backbones, and cDNA was synthesized in parallel reactions using random hexamer or oligo-dT primers. The apparent abundance of each construct was measured by qPCR using primer pair p2 (see FIG. 2E and Table 3), and normalized to the signal observed with random hexamers. As a control, endogenous GAPDH was measured using the same protocol. FIG. 8B depicts Western blot analysis of four replicate samples. α/β-Tubulin and fibrillarin (Cell Signaling Technology) are cytoplasmic and nuclear markers, respectively. Whole cell lysates were generated from 5% of the initial samples, prior to fractionation, by boiling cells in RIPA buffer. 1 11 g of protein was loaded onto each lane. FIG. 8C is a graph depicting qRT-PCR analysis of three replicates. XIST and SNHG5 are nuclear and cytoplasmic ncRNAs, respectively. Data were processed as in RIP experiments, renormalizing observed CT values to the total mass of RNA isolated from each subcellular compartment. Whole cell RNA was isolated from 5% of cells prior to fractionation. The percent yield, relative to whole cell RNA, reflects the abundance of transcript in each compartment. Values are means±standard deviations; four technical replicates. Primers are listed in Table 3. FIG. 8D is a graph depicting CMV/3'Box transcripts that are preferentially nuclear-retained. Cells expressing TOP1 from each Pol II backbone were fractionated and analyzed as in FIG. 8C. The abundance in each compartment, relative to that observed with EF1α/SV40 pA-TOP1-expressing cells, is shown. cDNA was primed with random hexamers; abundances were measured by qPCR using primer pair p2 (see FIG. 2E and Table 3). Values are means±standard deviations, n=3.

FIG. 9A-FIG. 9D (SEQ ID NO:8-16) are directed to synthesizing and sequencing the INT-$N_{25}$ Pool. FIG. 9A depicts sequences and chromatograms of seven individual clones isolated during initial synthesis of the INT-$N_{25}$ plasmid pool, aligned to the consensus (top). Nucleotides that match the consensus are notated as dots. Analysis and alignment were performed in Geneious (Biomatters Ltd). FIG. 9B depicts a sequencing chromatogram of the aggregate INT-N25 pool, aligned to the consensus. Priming was initiated from a M15 Reverse site located downstream of the sgRNA 3' terminus (not shown). Heterogeneity 5' of the insert is likely due to the small population of molecules containing inserts greater than 25 nucleotides in length (e.g., colony 5, above). FIG. 9C is a schematic summarizing the primer design used to generate targeted deep sequencing libraries. Complete primer sequences are listed in Table 4. FIG. 9D depicts bioanalyzer traces of the final sequencing libraries. For each, the expected length is 220 nt. Green and purple bands correspond to lane markers.

FIG. 10A is a graph of read counts of 25mers observed in the plasmid pool vs. mean read counts observed in input (not immunoprecipitated) RNA libraries. All data are shown. Of the 783,612 unique sequences observed, 524 (0.07%) and 7,011 (0.9%) were significantly enriched or depleted in the input RNA libraries, respectively (red). FIG. 10B is a zoomed view of FIG. 10A showing the majority of the data. FIG. 10C is a graph of mean read counts of 25mers observed in the input vs FLAG-dCas9 immunoprecipitated libraries. All data are shown. Of the 1,028,868 unique sequences observed, 115 (0.01%) and 228 (0.02%) were significantly enriched or depleted in the RIP libraries (red). A zoomed view representing the majority of these data is shown in FIG. 5D. Sequence analysis of significantly enriched/depleted 25mers revealed no clear sequence preferences for sgRNA expression or for sgRNA incorporation into dCas9 complexes.

FIG. 11A Left is a secondary structure of the Spinach2 aptamer, as observed in crystal structures. FIG. 11A Right is a predicted secondary structure of a minimal Spinach aptamer, "Baby Spinach" A double G-quadruplex core, which is responsible for binding DFHBI-1T, the fluorophore ligand, is boxed in green. The core is abutted on both sides by base-paired stems for which absolute sequence identity is thought to be inconsequential to activity. FIG. 11B depicts design of the "BOBS" construct with three tandem copies of the Baby Spinach core (green boxes) embedded in a single, extended stem-loop, contiguous with the sgRNA core (gray box).

FIG. 16 depicts bridged imaging of chromatin loci.

DETAILED DESCRIPTION

Figure 1A:
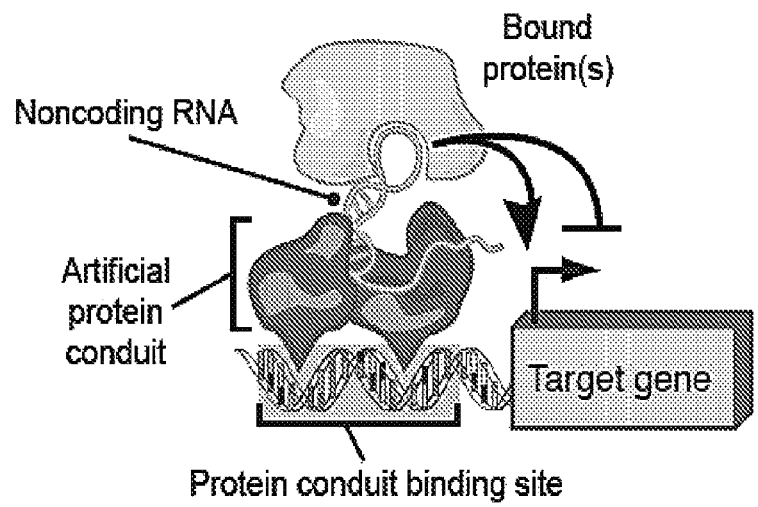
FIG. 1A-FIG. 1F relate to a dual reporter system for characterizing locus-specific ncRNA targeting strategies.

Embodiments of the present disclosure are directed to the use of a CRISPR/Cas system and, in particular, a guide RNA which includes a spacer sequence, a tracr mate sequence and a tracr sequence. The term spacer sequence is understood by those of skill in the art and may include any polynucleotide having sufficient complementarity with a target nucleic acid sequence to hybridize with the target nucleic acid sequence and direct sequence-specific binding of a CRISPR complex to the target sequence. The guide RNA may be formed from a spacer sequence covalently connected to a tracr mate sequence (which may be referred to as a crRNA) and a separate tracr sequence, wherein the tracr mate sequence is hybridized to a portion of the tracr sequence. According to certain aspects, the tracr mate sequence and the tracr sequence are connected or linked such as by covalent bonds by a linker sequence, which construct may be referred to as a fusion of the tracr mate sequence and the tracr sequence. The linker sequence referred to herein is a sequence of nucleotides, referred to herein as a nucleic acid sequence, which connect the tracr mate sequence and the tracr sequence. Accordingly, a guide RNA may be a two component species (i.e., separate crRNA and tracr RNA which hybridize together) or a unimolecular species (i.e., a crRNA-tracr RNA fusion, often termed an sgRNA).

A guide RNA as described herein also includes one or more of a selected RNA sequence, which may be referred to herein as a payload RNA sequence to the extent that the selected RNA sequence is connected to the guide RNA as described herein and is carried to a target nucleic acid, which may be DNA or RNA, for interaction with the target nucleic acid as described herein. Accordingly, methods are provided for localizing a selected RNA sequence at or near a target nucleic acid sequence, which may be DNA or RNA, so that the selected RNA sequence can perform a desired function or can carry an effector molecule to perform a desired function.

According to certain aspects, the spacer sequence is between about 13 and about 22 nucleotides in length. According to certain aspects, the tracr mate sequence is between about 17 and about 27 nucleotides in length. According to certain aspects, the tracr sequence is between about 65 and about 75 nucleotides in length. According to certain aspects, the linker nucleic acid sequence is between about 4 and about 6. According to certain aspects, the linker nucleic acid sequence is between about 4 and about 500 nucleotides. According to certain aspects, the linker nucleic acid sequence is between about 4 and about 400 nucleotides. According to certain aspects, the linker nucleic acid sequence is between about 4 and about 300 nucleotides. According to certain aspects, the linker nucleic acid sequence is between about 4 and about 250 nucleotides. According to certain aspects, the linker nucleic acid sequence is between about 4 and about 200 nucleotides.

According to certain aspects, the linker nucleic acid sequence is between about 20 and about 500 nucleotides. According to certain aspects, the linker nucleic acid sequence is between about 20 and about 400 nucleotides. According to certain aspects, the linker nucleic acid sequence is between about 20 and about 300 nucleotides. According to certain aspects, the linker nucleic acid sequence is between about 20 and about 250 nucleotides. According to certain aspects, the linker nucleic acid sequence is between about 20 and about 200 nucleotides.

According to certain aspects, the linker nucleic acid sequence is between about 25 and about 500 nucleotides. According to certain aspects, the linker nucleic acid sequence is between about 25 and about 400 nucleotides. According to certain aspects, the linker nucleic acid sequence is between about 25 and about 300 nucleotides. According to certain aspects, the linker nucleic acid sequence is between about 25 and about 250 nucleotides. According to certain aspects, the linker nucleic acid sequence is between about 25 and about 200 nucleotides.

According to certain aspects, the linker nucleic acid sequence is between about 30 and about 500 nucleotides. According to certain aspects, the linker nucleic acid sequence is between about 30 and about 400 nucleotides. According to certain aspects, the linker nucleic acid sequence is between about 30 and about 300 nucleotides. According to certain aspects, the linker nucleic acid sequence is between about 30 and about 250 nucleotides. According to certain aspects, the linker nucleic acid sequence is between about 30 and about 200 nucleotides.

According to certain aspects, the linker nucleic acid sequence is between about 50 and about 500 nucleotides. According to certain aspects, the linker nucleic acid sequence is between about 50 and about 400 nucleotides. According to certain aspects, the linker nucleic acid sequence is between about 50 and about 300 nucleotides. According to certain aspects, the linker nucleic acid sequence is between about 50 and about 250 nucleotides. According to certain aspects, the linker nucleic acid sequence is between about 50 and about 200 nucleotides.

According to certain aspects, the linker nucleic acid sequence is between about 75 and about 500 nucleotides. According to certain aspects, the linker nucleic acid sequence is between about 75 and about 400 nucleotides. According to certain aspects, the linker nucleic acid sequence is between about 75 and about 300 nucleotides. According to certain aspects, the linker nucleic acid sequence is between about 75 and about 250 nucleotides. According to certain aspects, the linker nucleic acid sequence is between about 75 and about 200 nucleotides.

According to certain aspects, the linker nucleic acid sequence is between about 100 and about 500 nucleotides. According to certain aspects, the linker nucleic acid sequence is between about 100 and about 400 nucleotides. According to certain aspects, the linker nucleic acid sequence is between about 100 and about 300 nucleotides. According to certain aspects, the linker nucleic acid sequence is between about 100 and about 250 nucleotides. According to certain aspects, the linker nucleic acid sequence is between about 100 and about 200 nucleotides.

According to aspects of the present disclosure, the guide RNA includes one or more selected RNA sequences at one or more guide RNA positions. A selected RNA sequence is understood to be an RNA sequence that is provided in addition to the spacer sequence, tracr mate sequence and tracr sequence. A selected RNA sequence is also understood to be that portion of a guide RNA in addition to the nucleic acid sequences defining the spacer sequence, tracr mate sequence and tracr sequence if the selected RNA sequence is attached to the spacer sequence, tracr mate sequence or tracr sequence. A selected RNA sequence may also be an RNA sequence that is provided in addition to a linker sequence. Linker sequences may be as short as a 4-6 nucleotide sequence and are used to connect the tracr mate sequence with the tracr sequence. A selected RNA sequence may be added to the linker sequence to increase its length, however, the combined linker sequence and selected RNA sequence may be referred to as a linker sequence insofar as the combination of a linker sequence and a selected RNA sequence function to link or connect the tracr mate sequence with the tracr sequence. Since the linker sequence connects the tracr mate sequence and the tracr sequence, a selected RNA sequence may be the portion of the linker sequence in addition to a 4-6 nucleotide linker sequence.

The selected RNA sequence may be joined, fused, connected, linked or otherwise tethered, such as by covalent bonds, to the guide RNA, such as at the 5' or 3' end of the guide RNA, such as at the 5' end of the spacer sequence or at the 3' end of the tracr sequence or the 5' end of the tracr sequence if not linked to the spacer sequence by a linker. The selected RNA sequence may be joined, fused, connected, linked or otherwise tethered, such as by covalent bonds, to either end of the guide RNA or internal to the guide RNA.

It is to be understood that production of guide RNA described herein may be by expression of a nucleic acid encoding the guide RNA sequence including one or more of a selected RNA sequence. Accordingly, reference to the selected RNA sequence being joined, fused, connected, linked or otherwise tethered, such as by covalent bonds, to the guide RNA, includes embodiments where a construct including a nucleic acid encoding such a guide RNA including one or more selected RNA sequences positioned at the 5' or 3' end of the guide RNA, such as at the 5' end of the spacer sequence or at the 3' end of the tracr sequence or the 5' end of the tracr sequence if not linked to the spacer sequence by a linker, or between and interconnecting the tracr mate sequence and the tracr sequence, and the guide RNA is expressed including one or more of a selected RNA sequence.

In addition to comparison with the spacer sequence, tracr mate sequence, tracr sequence and linker sequence, a selected RNA sequence may also be identified or described in terms of RNA species known to those of skill in the art. Such RNA species may have well known functions distinct from the functions of a spacer sequence, tracr mate sequence or tracr sequence and so a selected RNA sequence in a guide RNA may be identified or described as excluding those portions of a guide RNA having the function of a spacer sequence, tracr mate sequence or tracr sequence.

According to one aspect, the one or more selected RNA sequences have a nucleotide length between about 25 bases and about 10.0 kilobases. According to one aspect, the one or more selected RNA sequences have a nucleotide length between about 25 bases and about 5.0 kilobases. According to one aspect, the one or more selected RNA sequences have a nucleotide length between about 25 bases and about 4.8 kilobases. It is to be understood that reference to one or more selected RNA sequences having a nucleotide length within a range described herein means that each selected RNA sequence can have such a nucleotide length. According to one aspect, the one or more selected RNA sequences have a nucleotide length between about 30 bases and about 4.8 kilobases. According to one aspect, the one or more selected RNA sequences have a nucleotide length between about 35 bases and about 4.8 kilobases. According to one aspect, the one or more selected RNA sequences have a nucleotide length between about 40 bases and about 4.8 kilobases. According to one aspect, the one or more selected RNA sequences have a nucleotide length between about 45 bases and about 4.8 kilobases. According to one aspect, the one or more selected RNA sequences have a nucleotide length between about 50 bases and about 4.8 kilobases. According to one aspect, the one or more selected RNA sequences have a nucleotide length between about 55 bases and about 4.8 kilobases. According to one aspect, the one or more selected RNA sequences have a nucleotide length between about 60 bases and about 4.8 kilobases. According to one aspect, the one or more selected RNA sequences have a nucleotide length between about 65 bases and about 4.8 kilobases. According to one aspect, the one or more selected RNA sequences have a nucleotide length between about 70 bases and about 4.8 kilobases. According to one aspect, the one or more selected RNA sequences have a nucleotide length between about 75 bases and about 4.8 kilobases. According to one aspect, the one or more selected RNA sequences have a nucleotide length between about 80 bases and about 4.8 kilobases. According to one aspect, the one or more selected RNA sequences have a nucleotide length between about 85 bases and about 4.8 kilobases. According to one aspect, the one or more selected RNA sequences have a nucleotide length between about 90 bases and about 4.8 kilobases. According to one aspect, the one or more selected RNA sequences have a nucleotide length between about 95 bases and about 4.8 kilobases. According to one aspect, the one or more selected RNA sequences have a nucleotide length between about 100 bases and about 4.8 kilobases. According to one aspect, the one or more selected RNA sequences have a nucleotide length between about 200 bases and about 4.8 kilobases. According to one aspect, the one or more selected RNA sequences have a nucleotide length between about 200 bases and about 10.0 kilobases. According to one aspect, the one or more selected RNA sequences have a nucleotide length between about 300 bases and about 4.8 kilobases. According to one aspect, the one or more selected RNA sequences have a nucleotide length between about 300 bases and about 10.0 kilobases. According to one aspect, the one or more selected RNA sequences have a nucleotide length between about 400 bases and about 4.8 kilobases. According to one aspect, the one or more selected RNA sequences have a nucleotide length between about 400 bases and about 10.0 kilobases. According to one aspect, the one or more selected RNA sequences have a nucleotide length between about 500 bases and about 4.8 kilobases. According to one aspect, the one or more selected RNA sequences have a nucleotide length between about 500 bases and about 10.0 kilobases. According to one aspect, the one or more selected RNA sequences have a nucleotide length between about 600 bases and about 4.8 kilobases. According to one aspect, the one or more selected RNA sequences have a nucleotide length between about 600 bases and about 10.0 kilobases. According to one aspect, the one or more selected RNA sequences have a nucleotide length between about 700 bases and about 4.8 kilobases. According to one aspect, the one or more selected RNA sequences have a nucleotide length between about 700 bases and about 10.0 kilobases. According to one aspect, the one or more selected RNA sequences have a nucleotide length between about 800 bases and about 4.8 kilobases. According to one aspect, the one or more selected RNA sequences have a nucleotide length between about 800 bases and about 10.0 kilobases. According to one aspect, the one or more selected RNA sequences have a nucleotide length between about 900 bases and about 4.8 kilobases. According to one aspect, the one or more selected RNA sequences have a nucleotide length between about 900 bases and about 10.0 kilobases. According to one aspect, the one or more selected RNA sequences have a nucleotide length between about 1000 bases and about 4.8 kilobases. According to one aspect, the one or more selected RNA sequences have a nucleotide length between about 1000 bases and about 10.0 kilobases. According to one aspect, the one or more selected RNA sequences have a nucleotide length between about 1500 bases and about 4.8 kilobases. According to one aspect, the one or more selected RNA sequences have a nucleotide length between about 1500 bases and about 10.0 kilobases. According to one aspect, the one or more selected RNA sequences have a nucleotide length between about 2000 bases and about 4.8 kilobases. According to one aspect, the one or more selected RNA sequences have a nucleotide length between about 2000 bases and about 10.0 kilobases.

According to one aspect, embodiments described herein include guide RNA having a length including the sum of the lengths of a spacer sequence, tracr mate sequence, tracr sequence, linker sequence (if present) and one or more selected RNA sequences. Accordingly, such a guide RNA may be described by its total length which is a sum of its spacer sequence, tracr mate sequence, tracr sequence, linker sequence (if present) and one or more selected RNA sequences. According to this aspect, all of the ranges for the spacer sequence, tracr mate sequence, tracr sequence, linker sequence (if present) and one or more selected RNA sequences are incorporated herein by reference and need not be repeated. One of skill will readily be able to sum each of the portions of a guide RNA and the one or more of a selected RNA sequence to obtain the total length of the guide RNA sequence. For illustrative purposes, a guide RNA as describe herein may have a length of about 4909 bases where there are 13 spacer nucleotides+17 tracr mate nucleotides+65 tracr nucleotides+4 linker nucleotides+4.8 kilobase selected RNA nucleotides. A guide RNA as described herein may have a total length based on summing values provided by the ranges described herein. Aspects of the present disclosure are directed to methods of making such guide RNAs as described herein by expressing constructs encoding such guide RNA using promoters and terminators and optionally other genetic elements as described herein.

According to one aspect, the one or more selected RNA sequences are random RNA sequences. According to one aspect, the one or more selected RNA sequences are noncoding RNA sequences. According to one aspect, the one or more selected RNA sequences are long noncoding RNA sequences which have a nucleic acid length of about 200 nucleotides or greater. According to one aspect, the one or more selected RNA sequences are functional RNA sequences. According to one aspect, the selected RNA sequence has a desired function and interacts with the target nucleic acid in a manner to perform the desired function. According to one aspect, the selected RNA sequence is a functional RNA sequence that can bind to a functional domain, such as a transcriptional regulator protein or domain, which interacts with the target nucleic acid in a manner to perform the desired function. According to one aspect, the transcriptional regulator protein or domain is a transcriptional activator. According to one aspect, the transcriptional regulator protein or domain upregulates expression of the target nucleic acid. According to one aspect, the transcriptional regulator protein or domain is a transcriptional repressor. According to one aspect, the transcriptional regulator protein or domain downregulates expression of the target nucleic acid. Transcriptional activators and transcriptional repressors can be readily identified by one of skill in the art based on the present disclosure.

According to one aspect, the selected RNA sequence can bind directly or indirectly to a detectable label or marker, which can then be detected or imaged to identify the location of the target nucleic acid sequence. Detectable labels or markers can be readily identified by one of skill in the art based on the present disclosure.

Natural RNA domains useful in the present disclosure are known and have been adapted as components in artificial regulators, reporters and scaffolds. See Liang, J. C., Bloom, R. J. & Smolke, C. D. Engineering biological systems with synthetic RNA molecules. *Molecular cell* 43, 915-926 (2011); Chappell, J. et al. The centrality of RNA for engineering gene expression. *Biotechnology journal* 8, 1379-1395 (2013); Carothers, J. M., Goler, J. A., Juminaga, D. & Keasling, J. D. Model-driven engineering of RNA devices to quantitatively program gene expression. *Science* 334, 1716-1719 (2011); Delebecque, C. J., Lindner, A. B., Silver, P. A. & Aldaye, F. A. Organization of intracellular reactions with rationally designed RNA assemblies. *Science* 333, 470-474 (2011); Song, W., Strack, R. L., Svensen, N. & Jaffrey, S. R. Plug-and-play fluorophores extend the spectral properties of Spinach. *Journal of the American Chemical Society* 136, 1198-1201 (2014); and Auslander, S. et al. A general design strategy for protein-responsive riboswitches in mammalian cells. *Nat Meth* 11, 1154-1160 (2014) each of which are hereby incorporated by reference.

Useful selected RNA sequences include noncoding RNAs (ncRNAs) which are well known in the art. See Cech, T. R. & Steitz, J. A. The noncoding RNA revolution-trashing old rules to forge new ones. *Cell* 157, 77-94 (2014); Rinn, J. L. & Chang, H. Y. Genome regulation by long noncoding RNAs. *Annual review of biochemistry* 81, 145-166 (2012); and Ulitsky, I. & Bartel, D. P. lincRNAs: genomics, evolution, and mechanisms. *Cell* 154, 26-46 (2013) each of which are hereby incorporated by reference. Such noncoding RNAs may also include those referred to in the art as long noncoding RNAs or lncRNAs.

Additional useful RNA domains also include functional RNA motifs such as aptamers. Exemplary aptamers may function to sequester or recruit endogenous protein complexes to target loci. Other exemplary aptamers may function to sequester or recruit small molecules, such as dyes, fluorophores and metabolites, and recruit them to target loci. Additional useful RNA domains also include functional RNA motifs such as ribozymes. See Auslander, S. et al. A general design strategy for protein-responsive riboswitches in mammalian cells. *Nat Meth* 11, 1154-1160 (2014); Chen, X., Li, N. & Ellington, A. D. Ribozyme catalysis of metabolism in the RNA world. *Chemistry & biodiversity* 4, 633-655 (2007); Walker, S. C., Good, P. D., Gipson, T. A. & Engelke, D. R. The dual use of RNA aptamer sequences for affinity purification and localization studies of RNAs and RNA-protein complexes. *Methods in molecular biology* 714, 423-444 (2011); and Tome, J. M. et al. Comprehensive analysis of RNA-protein interactions by high-throughput sequencing-RNA affinity profiling. *Nature methods* 11, 683-688 (2014) each of which are hereby incorporated by reference. Exemplary ribozymes may function to tag nearby molecules with affinity tags or markers. Useful selected RNA sequences are disclosed in Liang, J. C., Bloom, R. J. & Smolke, C. D. Engineering biological systems with synthetic RNA molecules. *Molecular cell* 43, 915-926 (2011); Chappell, J. et al. The centrality of RNA for engineering gene expression. *Biotechnology journal* 8, 1379-1395 (2013); Delebecque, C. J., Lindner, A. B., Silver, P. A. & Aldaye, F. A. Organization of intracellular reactions with rationally designed RNA assemblies. *Science* 333, 470-474 (2011); Song, W., Strack, R. L., Svensen, N. & Jaffrey, S. R. Plug-and-play fluorophores extend the spectral properties of Spinach. *Journal of the American Chemical Society* 136, 1198-1201 (2014); Chen, X., Li, N. & Ellington, A. D. Ribozyme catalysis of metabolism in the RNA world. *Chemistry & biodiversity* 4, 633-655 (2007); Walker, S. C., Good, P. D., Gipson, T. A. & Engelke, D. R. The dual use of RNA aptamer sequences for affinity purification and localization studies of RNAs and RNA-protein complexes. *Methods in molecular biology* 714, 423-444 (2011) each of which are hereby incorporated by reference in their entireties.

According to certain aspects, a guide RNA including a spacer sequence, tracr mate sequence and tracr sequence may be referred to herein as a guide RNA scaffold to the extent that it may include one or more or a plurality of selected RNA sequences as defined herein to be used for certain one or more functions with a target nucleic acid sequence. For example, decorating loci with orthogonal RNA-based affinity tags (an embodiment of a selected RNA sequence) is useful for multiplexed dissection of locus-specific proteomes, transcriptomes and higher-order chromatin structures. Additionally, custom RNA scaffolds including one or more selected RNA sequences allow enzymatic activities to be uniquely targeted to discrete subnuclear sites. Additional useful selected RNA sequences include RNA domains such as sensors and processors. Exemplary sensors and processors can bind to an input signal (small molecule, protein or nucleic acid) and alter their structure and function in response. Additional useful RNA domains include long noncoding RNAs (lncRNAs) and their subdomains. LncRNAs may function to alter gene expression, the local chromatin environment, and the locus' association with subnuclear domains (i.e. the nucleolus, speckles, paraspeckles, and telomeres).

According to certain aspects of the present disclosure, the guide RNA includes a selected RNA sequence attached or connected to the 3' end of the tracr sequence (referred to herein as TOP1 or topology 1). According to this embodiment, the tracr sequence and the crRNA sequence may be separate or connected by the linker. When connected by a linker, this embodiment is referred to herein as TOP1 or topology 1. When not connected by a linker, this embodiment is referred to herein as TOP3 or topology 3.

According to certain aspects of the present disclosure, the guide RNA includes a selected RNA sequence attached or connected to the 5' end of crRNA, such as at the 5' end of the spacer sequence. According to this embodiment, the tracr sequence and the crRNA sequence may be separate or connected by the linker. When connected by a linker, this embodiment may be referred to as TOP2 or topology 2.

According to certain aspects of the present disclosure where the crRNA and the tracr sequence of the guide RNA are separate sequences, the selected RNA sequence may be attached or connected to the 5' end of the tracr sequence (referred to herein as TOP4 or topology 4) or the 3' end of the crRNA sequence.

According to certain aspects of the present disclosure, the guide RNA includes a selected RNA sequence as part of the linker sequence, i.e. the linker sequence includes a selected RNA sequence, such as the selected RNA sequence being connected in series with the linker or within the linker or attached to the linker (referred to herein as INT or internal).

According to certain aspects of the present disclosure, the guide RNA with the one or more selected RNA sequences is capable of binding to a target nucleic acid and otherwise complexing with an RNA guided binding protein of a CRISPR/Cas system. The RNA guided binding protein may be an RNA guided DNA binding protein or it may be an RNA guided RNA binding protein. According to this aspect, the spacer sequence is designed to bind to a target DNA sequence or a target RNA sequence so as to form a colocalization complex of the guide RNA and the RNA guided binding protein and either the target DNA sequence or target RNA sequence. The payload selected RNA sequence then interacts with the target DNA sequence or target RNA sequence or an effector molecule attached to the selected RNA sequence interacts with the target DNA sequence or target RNA sequence.

According to one aspect, guide RNAs including one or more selected RNAs as described herein can be designed to have a spacer sequence or other sequence, such as a selected RNA sequence, complementary to other cellular RNAs for example either for visualization of such cellular RNAs or potential inhibition or alteration of function of such cellular RNAs. By making guide RNAs as described herein that can complement a large portion of a target mRNA or lncRNA, a duplex could be formed and visualized for sub cellular localization, for example, if the RNA guided binding protein that colocalizes with the guide RNA at the target RNA includes a fluorescent moiety. According to one aspect, methods are provided to target cellular fusion proteins, such as those that result in disease, such as leukemia. Guide RNAs, such as long guide RNAs as described herein, complementary to large portions of mRNA which encode the fusion site of target fusion protein are designed to specifically target such mRNA.

According to certain aspects of the present disclosure, the guide RNA (such as a guide RNA scaffold) includes one or more selected RNA sequences (such as an RNA payload) at locations at or in or along the guide RNA which do not significantly interact with an RNA guided DNA binding protein so as to prevent the guide RNA from complexing with an RNA guided binding protein of a CRISPR/Cas system or otherwise prevent the colocalization of the guide RNA and the binding protein with the target nucleic acid, which may be DNA or RNA. According to certain aspects of the present disclosure, a plurality of selected RNA sequences may be connected at a particular location of the guide RNA described herein, such as being connected in series at a particular location of the guide RNA described herein, such as being connected in series at a 5' end, 3' end, linker or internal position of the guide RNA as described herein.

According to certain aspects, the selected RNA sequences may have any desirable conformation suitable for a particular purpose. Many possible RNA conformations are known based on RNA structure. Accordingly, the selected RNA sequences may include one or more of a hairpin structure or hairpin structures, three-way junctions, four-way junctions, higher order n-way junctions where n is 5-10, pseudoknots, structural scaffolds stabilized by a "kissing loop" or loop-bulge interactions, local triplex structures, higher order multi-stranded structures including guanosine quartets, and the like. This includes many known aptamers that can be employed to recruit proteins and their complexes to specific loci. Such aptamers include naturally occurring modules of non-host origin, such as the phage coat protein-binding stem-loops MS2 and PP7, or the archeal L7Ae protein-binding "kink-turn" motif. Exemplary RNA may further include domains from RNAs isolated from pathogens, such as the HIV TAR motif. Exemplary RNA may further include domains isolated from larger structured host RNAs, such as the XIST A-repeat ("RepA") motif, which binds Polycomb Repressive Complex 2 ("PRC2"). Exemplary RNA may further include artificial aptamers, such as those that specifically bind streptavidin or GFP.

According to certain aspects, the guide RNA, the selected RNA sequence, the nucleic acid binding protein which interacts with the guide RNA are foreign to the cell into which they are introduced. According to this aspect, the guide RNA, the selected RNA sequence, and the nucleic acid binding protein which interacts with the guide RNA are nonnaturally occurring in the cell in which they are presented. To this extent, cells may be genetically engineered or genetically modified to include the CRISPR systems described herein.

According to one aspect, methods disclosed herein include a nuclease null or nuclease inactive DNA binding protein, such as of a CRISPR/Cas system, such as a Cas9 protein that has been rendered nuclease inactive. The system of the present disclosure includes a guide RNA as described above having the one or more selected RNA sequences where the guide RNA binds or hybridizes to a target nucleic acid sequence and complexes with the DNA binding protein. A complex of the guide RNA, nuclease null or nuclease inactive DNA binding protein and the target nucleic acid result in the one or more selected RNA sequences or selected molecule or molecules bound or attached to the one or more selected RNA sequences such as proteins known to those of skill in the art as binding to RNA, being located at the target nucleic acid.

According to certain aspects, further useful selected RNA sequences or domains include synthetic or non-natural RNA domains that interact with a target nucleic acid. According to certain aspects, methods are provided for locus-targeted reconstitution of natural regulatory RNAs and for determining the mechanism of action of long noncoding RNAs. See Cech, T. R. & Steitz, J. A. The noncoding RNA revolution-trashing old rules to forge new ones. *Cell* 157, 77-94 (2014); Rinn, J. L. & Chang, H. Y. Genome regulation by long noncoding RNAs. *Annual review of biochemistry* 81, 145-166 (2012); Ulitsky, I. & Bartel, D. P. lincRNAs: genomics, evolution, and mechanisms. *Cell* 154, 26-46 (2013) and Bassett, A. R. et al. Considerations when investigating lncRNA function in vivo. *eLife* 3, e03058 (2014) each of which are hereby incorporated by reference in their entireties. According to certain aspects, methods are provided for locating an RNA domain, such as a long noncoding RNA—or subdomains within that RNA—to a given target nucleic acid, and determining if the RNA domain alone is functionally sufficient when decoupled from the act of its transcription.

According to one aspect as shown in FIG. 1A, a DNA binding protein is complexed with an RNA domain. The RNA domain may also include a selected RNA sequence, such as a noncoding RNA sequence which may have a protein bound thereto, and the DNA binding protein or DNA binding protein complex binds to the target nucleic acid thereby targeting the ncRNA and the bound protein to the target nucleic acid. The noncoding RNA may be one or more desired molecules bound or attached thereto.

Figure 1B:
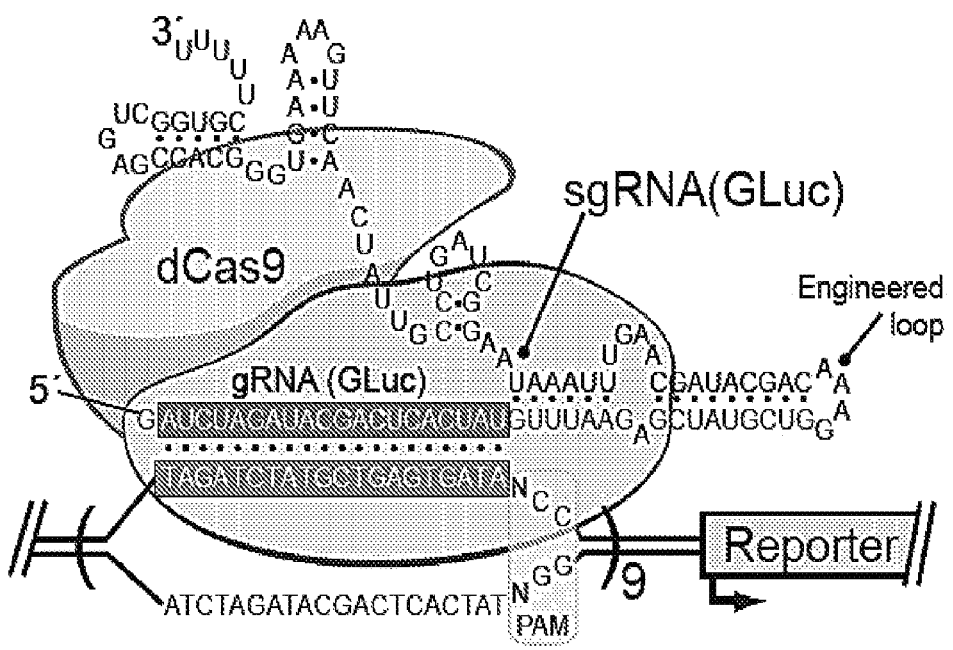

According to one aspect shown in FIG. 1B, a CRISPR/Cas system (such as a guide RNA and Cas9 system) is used to localize the selected RNA sequence at a target nucleic acid. FIG. 1B shows the sequence of an exemplary guide RNA, however, one of skill in the art will readily understand that a guide RNA may be designed to target any target nucleic acid, whether DNA or RNA, and may have any desirable spacer sequence, tracr mate sequence and tracr sequence and may include any desirable linker or engineered loop connecting the tracr mate sequence with the tracr sequence. One such CRISPR/Cas system uses the *S. pyogenes* Cas9 nuclease (Sp. Cas9), an extremely high-affinity (see Sternberg, S. H., Redding, S., Jinek, M., Greene, E. C. & Doudna, J. A. DNA interrogation by the CRISPR RNA-guided endonuclease Cas9. *Nature* 507, 62-67 (2014) hereby incorporated by reference in its entirety), programmable DNA-binding protein isolated from a type II CRISPR-associated system (see Garneau, J. E. et al. The CRISPR/Cas bacterial immune system cleaves bacteriophage and plasmid DNA. *Nature* 468, 67-71 (2010) and Jinek, M. et al. A programmable dual-RNA-guided DNA endonuclease in adaptive bacterial immunity. *Science* 337, 816-821 (2012) each of which are hereby incorporated by reference in its entirety). According to certain aspects, a nuclease null or nuclease deficient Cas 9 can be used in the methods described herein. Such nuclease null or nuclease deficient Cas9 proteins are described in Gilbert, L. A. et al. CRISPR-mediated modular RNA-guided regulation of transcription in eukaryotes. *Cell* 154, 442-451 (2013); Mali, P. et al. CAS9 transcriptional activators for target specificity screening and paired nickases for cooperative genome engineering. *Nature biotechnology* 31, 833-838 (2013); Maeder, M. L. et al. CRISPR RNA-guided activation of endogenous human genes. *Nature methods* 10, 977-979 (2013); and Perez- Pinera, P. et al. RNA-guided gene activation by CRISPR-Cas9-based transcription factors. *Nature methods* 10, 973-976 (2013) each of which are hereby incorporated by reference in its entirety. The DNA locus targeted by Cas9 (and by its nuclease-deficient mutant, "dCas9" precedes a three nucleotide (nt) 5'-NGG-3' "PAM" sequence, and matches a 15-22-nt guide or spacer sequence within a Cas9-bound RNA cofactor, referred to herein and in the art as a guide RNA. Altering this guide RNA is sufficient to target Cas9 or a nuclease deficient Cas9 to a target nucleic acid. In a multitude of CRISPR-based biotechnology applications (see Mali, P., Esvelt, K. M. & Church, G. M. Cas9 as a versatile tool for engineering biology. *Nature methods* 10, 957-963 (2013); Hsu, P. D., Lander, E. S. & Zhang, F. Development and Applications of CRISPR-Cas9 for Genome Engineering. *Cell* 157, 1262-1278 (2014); Chen, B. et al. Dynamic imaging of genomic loci in living human cells by an optimized CRISPR/Cas system. *Cell* 155, 1479-1491 (2013); Shalem, O. et al. Genome-scale CRISPR-Cas9 knockout screening in human cells. *Science* 343, 84-87 (2014); Wang, T., Wei, J. J., Sabatini, D. M. & Lander, E. S. Genetic screens in human cells using the CRISPR-Cas9 system. *Science* 343, 80-84 (2014); Nissim, L., Perli, S. D., Fridkin, A., Perez-Pinera, P. & Lu, T. K. Multiplexed and Programmable Regulation of Gene Networks with an Integrated RNA and CRISPR/Cas Toolkit in Human Cells. *Molecular cell* 54, 698-710 (2014); Ryan, O. W. et al. Selection of chromosomal DNA libraries using a multiplex CRISPR system. *eLife* 3 (2014); Gilbert, L. A. et al. Genome-Scale CRISPR-Mediated Control of Gene Repression and Activation. *Cell* (2014); and Citorik, R. J., Mimee, M. & Lu, T. K. Sequence-specific antimicrobials using efficiently delivered RNA-guided nucleases. *Nature biotechnology* (2014) each of which are hereby incorporated by reference in its entirety), the guide is often presented in a so-called sgRNA (single guide RNA), wherein the two natural Cas9 RNA cofactors (gRNA and tracrRNA) are fused via an engineered loop an example of which is shown in FIG. 1B.

According to one aspect, large RNA domains are provided to, attached to, bound to, linked to or are otherwise localized or complexed with a guide RNA at various locations within the guide RNA or at the ends of the guide RNA while maintaining RNA-directed localization of the Cas9 protein. Such attachment includes covalent and noncovalent attachment. The entire guide RNA with the selected RNA sequence or domain is encoded by a nucleic acid which is expressed by a cell to produce the guide RNA with the selected RNA sequence. The guide RNA is different from the selected RNA domain or sequence to which it is attached and may be referred to herein as a cargo sequence or payload sequence to the extent that the guide RNA is used to deliver the selected RNA sequence or sequences, molecules and combinations thereof, attached thereto if present to the target nucleic acid. According to one aspect, the selected RNA domain is directly linked or attached to the guide RNA (which may be referred to as "sgRNA") thereby carrying or delivering the RNA domain to the target nucleic acid sequence.

Embodiments of the present disclosure are directed to a method of delivering an RNA domain to a target nucleic acid in a cell comprising providing to the cell a Cas9 protein and a guide RNA having a selected RNA domain attached thereto or included therewith wherein the guide RNA and the Cas9 protein form a co-localization complex with the target nucleic acid. Methods described herein can be performed in vitro, in vivo or ex vivo.

According to one aspect, the cell is a eukaryotic cell or a prokaryotic cell. According to one aspect, the cell is a bacteria cell, a yeast cell, a mammalian cell, a plant cell or an animal cell. According to one aspect, the Cas9 protein is an enzymatically active Cas9 protein, a Cas9 protein wild-type protein, a Cas9 protein nickase or a nuclease null or nuclease deficient Cas9 protein. Additional exemplary Cas9 proteins include Cas9 proteins attached to, bound to or fused with functional proteins such as transcriptional regulators, such as transcriptional activators or repressors, a Fok-domain, such as Fok 1, an aptamer, a binding protein, PP7, MS2 and the like.

According to certain aspects, the Cas9 protein may be delivered directly to a cell by methods known to those of skill in the art, including injection or lipofection, or as translated from its cognate mRNA, or transcribed from its cognate DNA into mRNA (and thereafter translated into protein). Cas9 DNA and mRNA may be themselves introduced into cells through electroporation, transient and stable transfection (including lipofection) and viral transduction or other methods known to those of skill in the art. According to certain aspects, the guide RNA having an RNA domain attached thereto may be delivered directly to a cell as a native species by methods known to those of skill in the art, including injection or lipofection, or as transcribed from its cognate DNA, with the cognate DNA introduced into cells through electroporation, transient and stable transfection (including lipofection) and viral transduction.

According to certain aspects, a first nucleic acid encoding a Cas9 protein is provided to a cell. A second nucleic acid encoding guide RNA complementary to the target nucleic acid and having an RNA domain attached thereto is provided to the cell. The cell expresses the guide RNA and the Cas9 protein, wherein the guide RNA and the Cas9 protein form a co-localization complex with the target nucleic acid thereby delivering the selected RNA domain to the target nucleic acid. According to this aspect, the first nucleic acid encoding the Cas9 protein and the second nucleic acid encoding the guide RNA may be present on the same or different vectors. The cell may be any desired cell including a eukaryotic cell. An exemplary cell is a human cell. An exemplary cell is a stem cell, whether adult or embryonic. An exemplary cell is an induced pluripotent stem cell. An exemplary cell is an embryonic stem cell. According to this aspect, the embryonic stem cell which may then be implanted into an animal where the embryonic stem cell differentiates into a particular desired tissue type and the tissue type expresses the nucleic acids encoding the Cas9 and the guide RNA. According to certain aspects, the term CRISPR-Display refers to a CRISPR system including an RNA guided DNA or RNA binding protein and a guide RNA including a selected RNA sequence which is used to locate or display the selected RNA sequence at or near the target nucleic acid sequence. In this manner, a CRISPR-Display genetic animal model, such as a mouse model, is generated to deliver specific cargo (a selected RNA sequence or a molecule bound thereto) in vivo with combined transgenetic guide complexes (the guide RNAs with the selected RNA sequence attached thereto).

Embodiments of the present disclosure are directed to a method of delivering a Cas9 protein to cells within a subject comprising administering to the subject, such as systemically administering to the subject, such as by intravenous administration or injection, intraperitoneal administration or injection, intramuscular administration or injection, intracranial administration or injection, intraocular administration or injection, subcutaneous administration or injection, a Cas9 protein or a nucleic acid encoding the Cas9 protein.

Embodiments of the present disclosure are directed to a method of delivering a guide RNA having an RNA domain (selected RNA sequence) attached thereto to cells within a subject comprising administering to the subject, such as systemically administering to the subject, such as by intravenous administration or injection, intraperitoneal administration or injection, intramuscular administration or injection, intracranial administration or injection, intraocular administration or injection, subcutaneous administration or injection, a guide RNA having an RNA domain or a nucleic acid encoding the guide RNA having an RNA domain.

Embodiments of the present disclosure are directed to a method of delivering a Cas9 protein and a guide RNA to cells within a subject comprising administering to the subject, such as systemically administering to the subject, such as by intravenous administration or injection, intraperitoneal administration or injection, intramuscular administration or injection, intracranial administration or injection, intraocular administration or injection, subcutaneous administration or injection, a Cas9 protein or a nucleic acid encoding the Cas9 protein and a guide RNA or a nucleic acid encoding the guide RNA.

RNA guided DNA binding proteins are readily known to those of skill in the art to bind to DNA for various purposes. Such DNA binding proteins may be naturally occurring. DNA binding proteins having nuclease activity are known to those of skill in the art, and include naturally occurring DNA binding proteins having nuclease activity, such as Cas9 proteins present, for example, in Type II CRISPR systems. Such Cas9 proteins and Type II CRISPR systems are well documented in the art. See Makarova et al., *Nature Reviews, Microbiology*, Vol. 9, June 2011, pp. 467-477 including all supplementary information hereby incorporated by reference in its entirety.

In general, bacterial and archaeal CRISPR-Cas systems rely on short guide RNAs in complex with Cas proteins to direct degradation of complementary sequences present within invading foreign nucleic acid. See Deltcheva, E. et al. CRISPR RNA maturation by trans-encoded small RNA and host factor RNase III. *Nature* 471, 602-607 (2011); Gasiunas, G., Barrangou, R., Horvath, P. & Siksnys, V. Cas9-crRNA ribonucleoprotein complex mediates specific DNA cleavage for adaptive immunity in bacteria. *Proceedings of the National Academy of Sciences of the United States of America* 109, E2579-2586 (2012); Jinek, M. et al. A programmable dual-RNA-guided DNA endonuclease in adaptive bacterial immunity. *Science* 337, 816-821 (2012); Sapranauskas, R. et al. The *Streptococcus thermophilus* CRISPR/Cas system provides immunity in *Escherichia coli*. *Nucleic acids research* 39, 9275-9282 (2011); and Bhaya, D., Davison, M. & Barrangou, R. CRISPR-Cas systems in bacteria and archaea: versatile small RNAs for adaptive defense and regulation. *Annual review of genetics* 45, 273-297 (2011). A recent in vitro reconstitution of the *S. pyogenes* type II CRISPR system demonstrated that crRNA ("CRISPR RNA") fused to a normally trans-encoded tracrRNA ("trans-activating CRISPR RNA") is sufficient to direct Cas9 protein to sequence-specifically cleave target DNA sequences matching the crRNA. Expressing a gRNA homologous to a target site results in Cas9 recruitment and degradation of the target DNA. See H. Deveau et al., Phage response to CRISPR-encoded resistance in *Streptococcus thermophilus*. *Journal of Bacteriology* 190, 1390 (February, 2008).

Three classes of CRISPR systems are generally known and are referred to as Type I, Type II or Type III). According to one aspect, a particular useful enzyme according to the present disclosure to cleave dsDNA is the single effector enzyme, Cas9, common to Type II. See K. S. Makarova et al., Evolution and classification of the CRISPR-Cas systems. *Nature reviews. Microbiology* 9, 467 (June, 2011) hereby incorporated by reference in its entirety. Within bacteria, the Type II effector system consists of a long pre-crRNA transcribed from the spacer-containing CRISPR locus, the multifunctional Cas9 protein, and a tracrRNA important for gRNA processing. The tracrRNAs hybridize to the repeat regions separating the spacers of the pre-crRNA, initiating dsRNA cleavage by endogenous RNase III, which is followed by a second cleavage event within each spacer by Cas9, producing mature crRNAs that remain associated with the tracrRNA and Cas9. TracrRNA-crRNA fusions are contemplated for use in the present methods.

According to one aspect, the enzyme of the present disclosure, such as Cas9 unwinds the DNA duplex and searches for sequences matching the crRNA to cleave. Target recognition occurs upon detection of complementarity between a "protospacer" sequence in the target DNA and the remaining spacer sequence in the crRNA. Importantly, Cas9 cuts the DNA only if a correct protospacer-adjacent motif (PAM) is also present at the 3' end. According to certain aspects, different protospacer-adjacent motif can be utilized. For example, the *S. pyogenes* system requires an NGG sequence, where N can be any nucleotide. *S. thermophilus* Type II systems require NGGNG (see P. Horvath, R. Barrangou, CRISPR/Cas, the immune system of bacteria and archaea. *Science* 327, 167 (Jan. 8, 2010) hereby incorporated by reference in its entirety and NNAGAAW (see H. Deveau et al., Phage response to CRISPR-encoded resistance in *Streptococcus thermophilus*. *Journal of bacteriology* 190, 1390 (February, 2008) hereby incorporatd by reference in its entirety), respectively, while different *S. mutans* systems tolerate NGG or NAAR (see J. R. van der Ploeg, Analysis of CRISPR in *Streptococcus mutans* suggests frequent occurrence of acquired immunity against infection by M102-like bacteriophages. *Microbiology* 155, 1966 (June, 2009) hereby incorporated by refernece in its entirety. Bioinformatic analyses have generated extensive databases of CRISPR loci in a variety of bacteria that may serve to identify additional useful PAMs and expand the set of CRISPR-targetable sequences (see M. Rho, Y. W. Wu, H. Tang, T. G. Doak, Y. Ye, Diverse CRISPRs evolving in human microbiomes. *PLoS genetics* 8, e1002441 (2012) and D. T. Pride et al., Analysis of streptococcal CRISPRs from human saliva reveals substantial sequence diversity within and between subjects over time. *Genome research* 21, 126 (January, 2011) each of which are hereby incorporated by reference in their entireties.

In *S. pyogenes*, Cas9 generates a blunt-ended double-stranded break 3 bp upstream of the protospacer-adjacent motif (PAM) via a process mediated by two catalytic domains in the protein: an HNH domain that cleaves the complementary strand of the DNA and a RuvC-like domain that cleaves the non-complementary strand. See Jinek et al., *Science* 337, 816-821 (2012) hereby incorporated by reference in its entirety. Cas9 proteins are known to exist in many Type II CRISPR systems including the following as identified in the supplementary information to Makarova et al., Nature Reviews, Microbiology, Vol. 9, June 2011, pp. 467-477: *Methanococcus maripaludis* C7; *Corynebacterium diphtheriae*; *Corynebacterium efficiens* YS-314; *Corynebacterium glutamicum* ATCC 13032 Kitasato; *Corynebac-* terium glutamicum ATCC 13032 Bielefeld; *Corynebacterium glutamicum* R; *Corynebacterium kroppenstedtii* DSM 44385; *Mycobacterium abscessus* ATCC 19977; *Nocardia farcinica* IFM10152; *Rhodococcus erythropolis* PR4; *Rhodococcus jostii* RHA1; *Rhodococcus opacus* B4 uid36573; *Acidothermus cellulolyticus* 11B; *Arthrobacter chlorophenolicus* A6; *Kribbella flavida* DSM 17836 uid43465; *Thermomonospora curvata* DSM 43183; *Bifidobacterium dentium* Bd1; *Bifidobacterium longum* DJO10A; *Slackia heliotrinireducens* DSM 20476; *Persephonella marina* EX H1; *Bacteroides fragilis* NCTC 9434; *Capnocytophaga ochracea* DSM 7271; *Flavobacterium psychrophilum* JIP02 86; *Akkermansia muciniphila* ATCC BAA 835; *Roseiflexus castenholzii* DSM 13941; *Roseiflexus* RS1; *Synechocystis* PCC6803; *Elusimicrobium minutum* Pei191; uncultured Termite group 1 bacterium phylotype Rs D17; *Fibrobacter succinogenes* S85; *Bacillus cereus* ATCC 10987; *Listeria innocua; Lactobacillus casei; Lactobacillus rhamnosus* GG; *Lactobacillus salivarius* UCC118; *Streptococcus agalactiae* A909; *Streptococcus agalactiae* NEM316; *Streptococcus agalactiae* 2603; *Streptococcus dysgalactiae equisimilis* GGS 124; *Streptococcus equi zooepidemicus* MGCS10565; *Streptococcus gallolyticus* UCN34 uid46061; *Streptococcus gordonii* Challis subst CH1; *Streptococcus mutans* NN2025 uid46353; *Streptococcus mutans; Streptococcus pyogenes* M1 GAS; *Streptococcus pyogenes* MGAS5005; *Streptococcus pyogenes* MGAS2096; *Streptococcus pyogenes* MGAS9429; *Streptococcus pyogenes* MGAS10270; *Streptococcus pyogenes* MGAS6180; *Streptococcus pyogenes* MGAS315; *Streptococcus pyogenes* SSI-1; *Streptococcus pyogenes* MGAS10750; *Streptococcus pyogenes* NZ131; *Streptococcus thermophiles* CNRZ1066; *Streptococcus thermophiles* LMD-9; *Streptococcus thermophiles* LMG 18311; *Clostridium botulinum* A3 Loch Maree; *Clostridium botulinum* B Eklund 17B; *Clostridium botulinum* Ba4 657; *Clostridium botulinum* F Langeland; *Clostridium cellulolyticum* H10; *Finegoldia magna* ATCC 29328; *Eubacterium rectale* ATCC 33656; *Mycoplasma* gallisepticum; *Mycoplasma mobile* 163K; *Mycoplasma penetrans; Mycoplasma synoviae* 53; *Streptobacillus moniliformis* DSM 12112; *Bradyrhizobium* BTAi1; *Nitrobacter hamburgensis* X14; *Rhodopseudomonas palustris* BisB18; *Rhodopseudomonas palustris* BisB5; *Parvibaculum lavamentivorans* DS-1; Dinoroseobacter shibae DFL 12; *Gluconacetobacter diazotrophicus* Pal 5 FAPERJ; *Gluconacetobacter diazotrophicus* Pal 5 JGI; *Azospirillum* B510 uid46085; *Rhodospirillum rubrum* ATCC 11170; *Diaphorobacter* TPSY uid29975; *Verminephrobacter eiseniae* EF01-2; *Neisseria meningitides* 053442; *Neisseria meningitides* alpha14; *Neisseria meningitides* Z2491; *Desulfovibrio salexigens* DSM 2638; *Campylobacter jejuni* doylei 269 97; *Campylobacter jejuni* 81116; *Campylobacter jejuni; Campylobacter lari* RM2100; *Helicobacter hepaticus; Wolinella succinogenes; Tolumonas auensis* DSM 9187; *Pseudoalteromonas atlantica* T6c; *Shewanella pealeana* ATCC 700345; *Legionella pneumophila* Paris; *Actinobacillus succinogenes* 130Z; *Pasteurella multocida; Francisella tularensis novicida* U112; *Francisella tularensis* holarctica; *Francisella tularensis* FSC 198; *Francisella tularensis tularensis; Francisella tularensis* WY96-3418; and *Treponema denticola* ATCC 35405. The Cas9 protein may be referred by one of skill in the art in the literature as Csn1. An exemplary *S. pyogenes* Cas9 protein sequence is shown below. See Deltcheva et al., *Nature* 471, 602-607 (2011) hereby incorporated by reference in its entirety.

```
                                              (SEQ ID NO: 20)
MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD.
```

Modification to the Cas9 protein is a representative embodiment of the present disclosure. CRISPR systems useful in the present disclosure are described in R. Barrangou, P. Horvath, CRISPR: new horizons in phage resistance and strain identification. *Annual review of food science and technology* 3, 143 (2012) and B. Wiedenheft, S. H. Sternberg, J. A. Doudna, RNA-guided genetic silencing systems in bacteria and archaea. *Nature* 482, 331 (Feb. 16, 2012) each of which are hereby incorporated by reference in their entireties.

According to certain aspects, the DNA binding protein is altered or otherwise modified to inactivate the nuclease activity. Such alteration or modification includes altering one or more amino acids to inactivate the nuclease activity or the nuclease domain. Such modification includes removing the polypeptide sequence or polypeptide sequences exhibiting nuclease activity, i.e. the nuclease domain, such that the polypeptide sequence or polypeptide sequences exhibiting nuclease activity, i.e. nuclease domain, are absent from the DNA binding protein. Other modifications to inactivate nuclease activity will be readily apparent to one of skill in the art based on the present disclosure. Accordingly, a nuclease-null DNA binding protein includes polypeptide sequences modified to inactivate nuclease activity or removal of a polypeptide sequence or sequences to inactivate nuclease activity. The nuclease-null DNA binding protein retains the ability to bind to DNA even though the nuclease activity has been inactivated. Accordingly, the DNA binding protein includes the polypeptide sequence or sequences required for DNA binding but may lack the one or more or all of the nuclease sequences exhibiting nuclease activity. Accordingly, the DNA binding protein includes the polypeptide sequence or sequences required for DNA binding but may have one or more or all of the nuclease sequences exhibiting nuclease activity inactivated.

According to one aspect, a DNA binding protein having two or more nuclease domains may be modified or altered to inactivate all but one of the nuclease domains. Such a modified or altered DNA binding protein is referred to as a DNA binding protein nickase, to the extent that the DNA binding protein cuts or nicks only one strand of double stranded DNA. When guided by RNA to DNA, the DNA binding protein nickase is referred to as an RNA guided DNA binding protein nickase. An exemplary DNA binding protein is an RNA guided DNA binding protein nuclease of a Type II CRISPR System, such as a Cas9 protein or modified Cas9 or homolog of Cas9. An exemplary DNA binding protein is a Cas9 protein nickase. An exemplary DNA binding protein is an RNA guided DNA binding protein of a Type II CRISPR System which lacks nuclease activity. An exemplary DNA binding protein is a nuclease-null or nuclease deficient Cas9 protein.

According to an additional aspect, nuclease-null Cas9 proteins are provided where one or more amino acids in Cas9 are altered or otherwise removed to provide nuclease-null Cas9 proteins. According to one aspect, the amino acids include D10 and H840. See Jinek et al., *Science* 337, 816-821 (2012). According to an additional aspect, the amino acids include D839 and N863. According to one aspect, one or more or all of D10, H840, D839 and H863 are substituted with an amino acid which reduces, substantially eliminates or eliminates nuclease activity. According to one aspect, one or more or all of D10, H840, D839 and H863 are substituted with alanine. According to one aspect, a Cas9 protein having one or more or all of D10, H840, D839 and H863 substituted with an amino acid which reduces, substantially eliminates or eliminates nuclease activity, such as alanine, is referred to as a nuclease-null Cas9 ("Cas9Nuc") and exhibits reduced or eliminated nuclease activity, or nuclease activity is absent or substantially absent within levels of detection. According to this aspect, nuclease activity for a Cas9Nuc may be undetectable using known assays, i.e. below the level of detection of known assays.

According to one aspect, the Cas9 protein, Cas9 protein nickase or nuclease null Cas9 includes homologs and orthologs thereof which retain the ability of the protein to bind to the DNA and be guided by the RNA. According to one aspect, the Cas9 protein includes the sequence as set forth for naturally occurring Cas9 from *S. pyogenes* and protein sequences having at least 30%, 40%, 50%, 60%, 70%, 80%, 90%, 95%, 98% or 99% homology thereto and being a DNA binding protein, such as an RNA guided DNA binding protein.

Target nucleic acids include any nucleic acid sequence to which a co-localization complex as described herein can be useful to either cut, nick, regulate, identify, influence or otherwise target for other useful purposes using the methods described herein. Target nucleic acids include cellular RNA. Target nucleic acids include cellular DNA. Target nucleic acids include genes. For purposes of the present disclosure, DNA, such as double stranded DNA, can include the target nucleic acid and a co-localization complex can bind to or otherwise co-localize with the DNA at or adjacent or near the target nucleic acid and in a manner in which the co-localization complex may have a desired effect on the target nucleic acid. Such target nucleic acids can include endogenous (or naturally occurring) nucleic acids and exogenous (or foreign) nucleic acids. One of skill based on the present disclosure will readily be able to identify or design guide RNAs and Cas9 proteins which co-localize to a DNA including a target nucleic acid. One of skill will further be able to identify transcriptional regulator proteins or domains which likewise co-localize to a DNA including a target nucleic acid. DNA includes genomic DNA, mitochondrial DNA, viral DNA or exogenous DNA.

Foreign nucleic acids (i.e. those which are not part of a cell's natural nucleic acid composition) may be introduced into a cell using any method known to those skilled in the art for such introduction. Such methods include transfection, transduction, viral transduction, microinjection, lipofection, nucleofection, nanoparticle bombardment, transformation, conjugation and the like. One of skill in the art will readily understand and adapt such methods using readily identifiable literature sources.

Vectors are contemplated for use with the methods and constructs described herein. The term "vector" includes a nucleic acid molecule capable of transporting another nucleic acid to which it has been linked. Vectors used to deliver the nucleic acids to cells as described herein include vectors known to those of skill in the art and used for such purposes. Certain exemplary vectors may be plasmids, lentiviruses or adeno-associated viruses known to those of skill in the art. Vectors include, but are not limited to, nucleic acid molecules that are single-stranded, doublestranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, lentiviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." Common expression vectors of utility in recombinant DNA techniques are often in the form of plasmids. Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

Methods of non-viral delivery of nucleic acids or native DNA binding protein, native guide RNA or other native species include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration). The term native includes the protein, enzyme or guide RNA species itself and not the nucleic acid encoding the species.

Regulatory elements are contemplated for use with the methods and constructs described herein. The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector may comprise one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter and Pol II promoters described herein. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

Aspects of the methods described herein may make use of terminator sequences. A terminator sequence includes a section of nucleic acid sequence that marks the end of a gene or operon in genomic DNA during transcription. This sequence mediates transcriptional termination by providing signals in the newly synthesized mRNA that trigger processes which release the mRNA from the transcriptional complex. These processes include the direct interaction of the mRNA secondary structure with the complex and/or the indirect activities of recruited termination factors. Release of the transcriptional complex frees RNA polymerase and related transcriptional machinery to begin transcription of new mRNAs. Terminator sequences include those known in the art and identified and described herein.

Aspects of the methods described herein may make use of epitope tags and reporter gene sequences. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, betaglucuronidase, luciferase, green fluorescent protein (GFP), HcRed, DsRed, cyan fluorescent protein (CFP), yellow fluorescent protein (YFP), and autofluorescent proteins including blue fluorescent protein (BFP).

The present disclosure provides a method of making a guide RNA including a selected RNA sequence including constructing a nucleic acid sequence including a first nucleic acid sequence encoding a guide RNA having a spacer sequence, a tracr mate sequence and a tracr sequence, wherein the tracr mate sequence and the tracr sequence are optionally connected by a linker sequence, and wherein the selected RNA sequence is fused to the 3' end of the tracr sequence, the 5' end of the spacer sequence, the 5' end of the tracr sequence if present, or the selected RNA sequence is fused to the linker sequence if present, or the selected RNA sequence is the linker sequence and wherein the selected nucleic acid sequence includes from 10 to 10,000 nucleotides, and a Pol II promoter sequence and a Pol II terminator sequence, and introducing the nucleic acid sequence into a cell, and expressing the nucleic acid sequence to produce the guide RNA including the selected RNA sequence. The disclosure provides that the Pol II promoter sequence is CMVPro or U1Pro and the Pol II terminator sequence is U1 3'Box, MASC or U2 smBox/U1 3'Box. The disclosure provides that the cell is in vitro, in vivo or ex vivo. The disclosure provides that the cell is a eukaryotic cell or prokaryotic cell. The disclosure provides that the cell is a bacteria cell, a fungal cell, a yeast cell, a mammalian cell, a plant cell or an animal cell. The disclosure provides that the selected RNA sequence is between about 10 and about 10,000 nucleotides. The disclosure provides that the selected RNA sequence is between about 30 and about 5,000 nucleotides. The disclosure provides that the selected RNA sequence is between about 40 and about 5,000 nucleotides. The disclosure provides that the selected RNA sequence is between about 50 and about 5,000 nucleotides. The disclosure provides that the selected RNA sequence is between about 60 and about 5,000 nucleotides. The disclosure provides that the selected RNA sequence is between about 70 and about 5,000 nucleotides. The disclosure provides that the selected RNA sequence is between about 80 and about 5,000 nucleotides. The disclosure provides that the selected RNA sequence is between about 90 and about 5,000 nucleotides. The disclosure provides that the selected RNA sequence is between about 100 and about 5,000 nucleotides. The disclosure provides that the selected RNA sequence is between about 110 and about 5,000 nucleotides. The disclosure provides that the selected RNA sequence is between about 120 and about 5,000 nucleotides. The disclosure provides that the selected RNA sequence is between about 130 and about 5,000 nucleotides. The disclosure provides that the selected RNA sequence is between about 140 and about 5,000 nucleotides. The disclosure provides that the selected RNA sequence is between about 150 and about 5,000 nucleotides. The disclosure provides that the selected RNA sequence is between about 175 and about 5,000 nucleotides. The disclosure provides that the selected RNA sequence is between about 200 and about 5,000 nucleotides. The disclosure provides that the selected RNA sequence is between about 250 and about 5,000 nucleotides. The disclosure provides that the selected RNA sequence is between about 300 and about 5,000 nucleotides. The disclosure provides that the selected RNA sequence is between about 400 and about 5,000 nucleotides. The disclosure provides that the selected RNA sequence is between about 500 and about 5,000 nucleotides. The disclosure provides that the selected RNA sequence is an aptamer, a noncoding RNA, a ribozyme, a functional RNA sequence, a pool of random RNA sequences, an RNA scaffold, an RNA-based sensor or signal processor, an RNA-based signaling device, a naturally occurring lncRNA, a naturally occurring lncRNA subdomain, a synthetic lncRNA, or synthetic lncRNA subdomain.

The disclosure provides a cell including a first nucleic acid sequence encoding a guide RNA having a spacer sequence, a tracr mate sequence and a tracr sequence, wherein the tracr mate sequence and the tracr sequence are optionally connected by a linker sequence, and wherein the selected RNA sequence is fused to the 3' end of the tracr sequence, the 5' end of the spacer sequence, the 5' end of the tracr sequence if present, or the selected RNA sequence is fused to the linker sequence if present, or the selected RNA sequence is the linker sequence and wherein the selected nucleic acid sequence includes from 10 to 10,000 nucleotides, and a Pol II promoter sequence and a Pol II terminator sequence.

The following examples are set forth as being representative of the present disclosure. These examples are not to be construed as limiting the scope of the present disclosure as these and other equivalent embodiments will be apparent in view of the present disclosure, figures and accompanying claims.

Example I

Plasmid Synthesis

Mammalian expression and reporter constructs were generated using standard restriction enzyme-based and ligation-independent cloning methods. *Gaussia* and *Cypridina* luciferases were derived from pGLuc-Basic and pCLuc-Basic, respectively (New England Biolabs). dCas9 (*S. pyogenes* D10A/H841A Cas9) was isolated from Addgene plasmid 47754, the EF1α promoter from Addgene plasmid 11154, mCerulean from Addgene plasmid 23244, Venus from Addgene 15753 and the human Ubiquitin C promoter (hUBCPro) used to drive expression of L7Ae~VP and PP7~VP from Addgene plasmid 17627. All other components were synthesized de novo from gBlocks or from smaller synthetic oligonucleotides (Integrated DNA Technologies).

The backbone for Lentiviral reporter constructs was derived from pLenti6.3/TO/V5-DEST (Life Technologies), from which the Tet-reponsive promoter and Gateway cloning sites were removed. The backbone for the MS2~VP constructs was derived from pcDNA3.1(+) (Life Technologies) in which the Neomycin expression cassette was removed. All other constructs were cloned into pNEB193 (New England Biolabs).

L7Ae, MS2 and PP7 were codon-optimized for expression in human cells and synthesized as gBlocks (Integrated DNA Technologies). The PP7 construct consists of two tandem copies of the non-aggregating ΔFG mutant (see Chao, J. A., Patskovsky, Y., Almo, S. C. & Singer, R. H. Structural basis for the coevolution of a viral RNA-protein complex. *Nature structural & molecular biology* 15, 103-105 (2008) hereby incorporated by reference in its entirety) joined by a flexible seven amino acid linker with the sequence GSTSGSG. Similarly, the MS2 construct consists of two tandem copies of the non-aggregating V75E/A81G mutant (see LeCuyer, K. A., Behlen, L. S. & Uhlenbeck, O. C. Mutants of the bacteriophage MS2 coat protein that alter its cooperative binding to RNA. *Biochemistry* 34, 10600-10606 (1995) hereby incorporated by reference in its entirety) joined by the same linker. L7Ae was designed according to a published sequence (see Saito, H. et al. Synthetic translational regulation by an L7Ae-kink-turn RNP switch. *Nature chemical biology* 6, 71-78 (2010) hereby incorporated by reference in its entirety).

Exemplary internally appended constructs ("INT") are shown in FIG. 5A, FIG. 5B, FIG. 5C and FIG. 5E. Sequences are provided in Table 5. Such internally appended constructs were cloned as follows. An INT general-purpose cloning vector was first cloned, "sgINTgpc," containing the following pertinent sequence (SEQ ID NO:21):

*GATCTAGATACGACTCACTATGTTTAAGAGCTATGCTGCGAATACGAGAA*

GTCTTCTTTTTTGAAGACAATCGTATTCGCAGCATAGCAAGTTTAAATAA

GGCTAGTCCGTTATCAACTTGAAAAAGTGGCACCGAGTCGGTGCTTTTTT

T

Italicized nucleotides denote the GLuc-targeting protospacer sequence as shown in Table 1 and Table 2, where underlined nucleotides denote an extended sgRNA stem1 and bold nucleotides denote two outward-facing BbsI restriction sites. This cassette is under expression of a human U6 promoter (not shown). Inserts cloned into this backbone had the general format: 5'-<u>CGAG</u>-[Insert]-<u>CTCGT</u>-3', wherein underlined nucleotides denote the sticky ends used for cloning; the additional C following the insert restores base-pairing at the end of stem1. These inserts were generated by PCR and restriction digestion with BbsI, or by annealing synthetic, 5'-phosphorylated oligonucleotides (following the protocol used for the $N_{25}$ pool, below). Inserts were ligated into BbsI-digested, gel-purified sgINTgpc using the Quick Ligation Kit (New England Biolabs).

All sgRNAs and derivatives were initially cloned bearing a GLuc-targeting protospacer. NTF3- and telomere-targeting constructs data for which is provided in FIG. 2F, FIG. 5F, FIG. 6B and FIG. 6C were derived from these parental constructs using an inverse-PCR method, using a forward primer that anneals downstream of the protospacer and a reverse primer that anneals to the 3'-end of the U6 promoter. Namely, PCR products were amplified with primers of the general format (SEQ ID NO:22-23):

```
Forward: TAGTAGAAGACAAXXXXXXXXXXXXXGTTTAAGAGCTATGC
TGCGAATACG

Reverse: TAGTAGAAGACAAYYYYYYYYYYYYGGTGTTTCGTCCTTTC
CAC
```

Bold nucleotides denote BbsI restriction sites; X's denote nucleotides 9-21 of the new protospacer sequence; Y's denote the reverse complement of nucleotides 1-9 of the new protospacer; underlined nucleotides are reverse complementary to one another. PCR products were purified using the QIAgen PCR cleanup kit, digested with BbsI and DpnI, purified again and quantified by UV-vis spectroscopy. Products (25 ng, in 11 µL final) were self-ligated using the Quick Ligation Kit (New England Biolabs).

Constructs employing the U1 3' Box terminator ended with the sequence (SEQ ID NO:24):

```
ACTTTCTGGAGTTTCAAAAGTAGACTGTACGCTAAGGGTCATATCTTTTT
TTGTTTGGTTTGTGTCTTGGTTGGCGTCTTAA
```

The italicized nucleotides comprise a linker, and the remainder comprise the U1 3' Box terminator (hereinafter, "U1 3' Box").

The U1 promoter sequence (hereinafter, "U1Pro") used in U1/sm/3'Box constructs was (SEQ ID NO:25):

```
CTAAGGACCAGCTTCTTTGGGAGAGAACAGACGCAGGGGCGGGAGGGAAA
AAGGGAGAGGCAGACGTCACTTCCCCTTGGCGGCTCTGGCAGCAGATTGG
TCGGTTGAGTGGCAGAAAGGCAGACGGGGACTGGGCAAGGCACTGTCGGT
GACATCACGGACAGGGCGACTTCTATGTAGATGAGGCAGCGCAGAGGCTG
CTGCTTCGCCACTTGCTGCTTCACCACGAAGGAGTTCCCGTGCCCTGGGA
GCGGGTTCAGGACCGCTGATCGGAAGTGAGAATCCCAGCTGTGTGTCAGG
GCTGGAAAGGGCTCGGGAGTGCGCGGGGCAAGTGACCGTGTGTGTAAAGA
GTGAGGCGTATGAGGCTGTGTCGGGGCAGAGGCCCAAGATCTC
```

These constructs terminated with the following sequence (SEQ ID NO:26):

```
CAGCAAGTTCAGAGAAATCTGAACTTGCTGGATTTTTGGAGCAGGGAGAT
GGAATAGGAGCTTGCTCCGTCCACTCCACGCATCGACCTGGTATTGCAGT
ACCTCCAGGAACGGTGCACCCACTTTCTGGAGTTTCAAAAGTAGACTGTA
CGCTAAGGGTCATATCTTTTTTGTTTGGTTTGTGTCTTGGTTGGCGTCT
TAA
```

Italicized nucleotides comprise a linker, bold nucleotides comprise the U2 snRNA sm-box (hereinafter, "U2 smBox"), and the remaining 3' sequence comprises the linker and U1 3'Box terminator as defined above.

Constructs employing the MALAT1-derived MASC structure ended with the sequence (SEQ ID NO:27):

```
GATTCGTCAGTAGGGTTGTAAAGGTTTTTCTTTTCCTGAGAAAACAACCT
TTTGTTTTCTCAGGTTTTGCTTTTTGGCCTTTCCCTAGCTTTAAAAAAAA
AAAAGCAAAAGACGCTGGTGGCTGGCACTCCTGGTTTCCAGGACGGGGTT
CAAGTCCCTGCGGTGTCTTTGCTT
```

The bold, larger AG denote the nucleotides adjoining the RNase P processing site, italicized nucleotides denote the MASC RNA.

En toto, Pol II-driven modified sgRNA were assembled by standard restriction enzyme-based or ligation-independent methods. Unless otherwise stated, constructs employed the standard Cytomegalovirus (CMV) immediate-early promoter/enhancer, hereafter termed "CMVPro" Construct sequences had the following general forms:

```
CMV/3'BOX (SEQ ID NO: 28):
[CMVPro]-[modified sgRNA or crRNA]-
ACTTTCTGGAGTTTCAAAAGTAGACTGTACGCTAAGGGTCATATCTTTTT
TTGTTTGGTTTGTGTCTTGGTTGGCGTCTTAA CMV/MASC (SEQ ID NO: 29):
[CMVPro]-[modified sgRNA or crRNA]-
GATTCGTCAGTAGGGTTGTAAAGGTTTTTCTTTTCCTGAGAAAACAACCT
TTTGTTTTCTCAGGTTTTGCTTTTTGGCCTTTCCCTAGCTTTAAAAAAAA
AAAAGCAAAAGACGCTGGTGGCTGGCACTCCTGGTTTCCAGGACGGGGTT
CAAGTCCCTGCGGTGTCTTTGCTT U1/sm/U2 (SEQ ID NO: 30):
CTAAGGACCAGCTTCTTTGGGAGAGAACAGACGCAGGGGCGGGAGGGAAA
AAGGGAGAGGCAGACGTCACTTCCCCTTGGCGGCTCTGGCAGCAGATTGG
TCGGTTGAGTGGCAGAAAGGCAGACGGGGACTGGGCAAGGCACTGTCGGT
GACATCACGGACAGGGCGACTTCTATGTAGATGAGGCAGCGCAGAGGCTG
CTGCTTCGCCACTTGCTGCTTCACCACGAAGGAGTTCCCGTGCCCTGGGA
GCGGGTTCAGGACCGCTGATCGGAAGTGAGAATCCCAGCTGTGTGTCAGG
GCTGGAAAGGGCTCGGGAGTGCGCGGGGCAAGTGACCGTGTGTGTAAAGA
GTGAGGCGTATGAGGCTGTGTCGGGGCAGAGGCCCAAGATCTC-[modi-
fied sgRNA or crRNA]-CAGCAAGTTCAGAGAAATCTGAACTTGCT
GGATTTTTGGAGCAGGGAGATGGAATAGGAGCTTGCTCCGTCCACTCCAC
GCATCGACCTGGTATTGCAGTACCTCCAGGAACGGTGCACCCACTTTCTG
GAGTTTCAAAAGTAGACTGTACGCTAAGGGTCATATCTTTTTTGTTTGG
TTTGTGTCTTGGTTGGCGTCTTAA
```

All plasmid sequences were confirmed by Sanger sequencing (GeneWiz) prior to use.

Example II

Cloning the N$_{25}$ Pool

Pool oligonucleotides (Integrated DNA Technologies) were as follows:

```
                                              (SEQ ID NO: 31)
5'-[P]-CGAGNNNNNNNNNNNNNNNNNNNNNNNNNC-3'

(SEQ ID NO: 32)
5'-[P]-ACGAGNNNNNNNNNNNNNNNNNNNNNNNNNN-3'
```

Figure 9A:
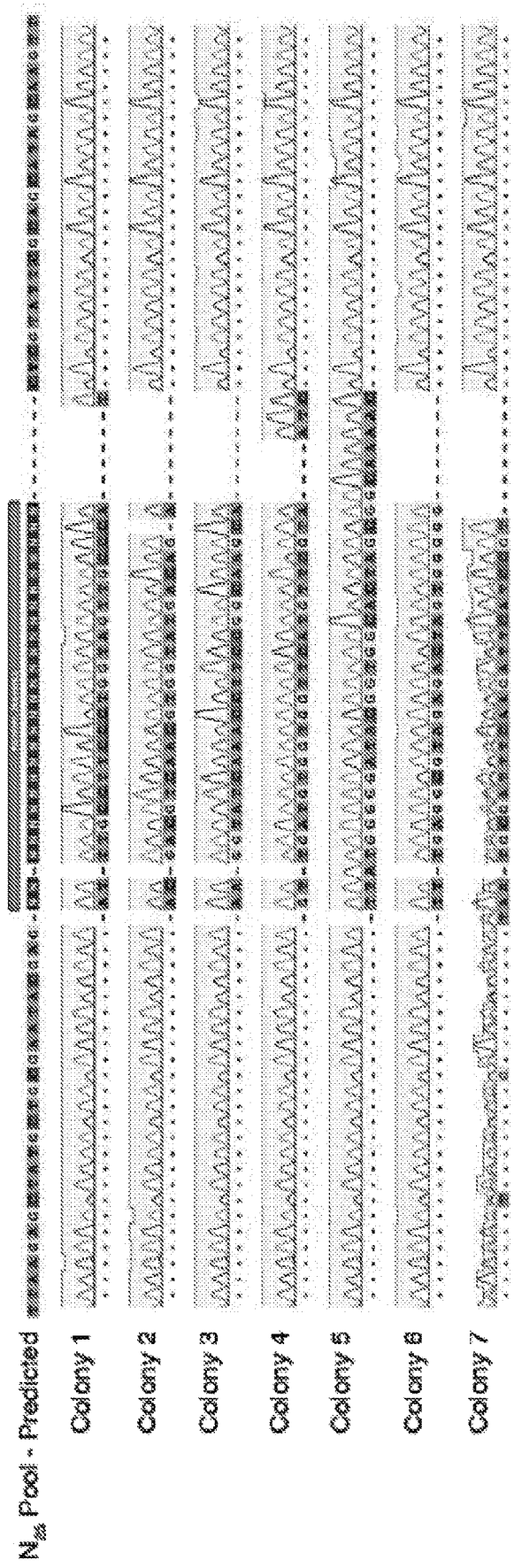

5'-[P] denotes a 5' Phosphate, and N denotes an equimolar mixture of all four nucleotides. Oligonucleotides were resuspended in annealing buffer (10 mM Tris, pH 7.0, 50 mM NaCl) to 100 µM. 10 µL of each oligo were mixed in a 0.2 mL PCR tube; this mixture was heated to 95° C. for 10 minutes and slowly annealed to 25° C. over the course of two hours in a thermocycler. The reaction was snap-cooled on ice and diluted 100-fold with ice-cold annealing buffer. 1 µL of this diluted duplex mix was ligated into 25 ng of BbsI-cut sgINTgpc, in 12 µL final volume, using the Quick Ligation Kit (New England Biolabs). The entire reaction was transformed into 120 µL of XL10-Gold ultracompetent cells (Agilent), plated onto 12 LB Ampicillin plates and grown overnight at 37° C. Seven bacterial colonies were picked for Sanger sequencing, data for which is shown in FIG. 9A, and the remainder were pooled by scraping the plates into 100 mL of liquid LB(Amp). Bacteria were pelleted by ultracentrifugation, and the plasmid pool was harvested in a single plasmid maxi-prep (QIAgen) data for which is shown in FIG. 9B.

Example III

Cell Culture, Stable and Transient Transgene Expression

HEK 293FT cells (ATCC) were maintained on gelatinized plates in high glucose Dulbecco's modified Eagle's medium (DMEM, Gibco), supplemented with 10% FBS, lx penicillin/streptomycin and 2 mM L-Glutamine (Gibco). Cells were grown at 37° C. and 5% $CO_2$ in a humidified incubator.

Figure 6A:
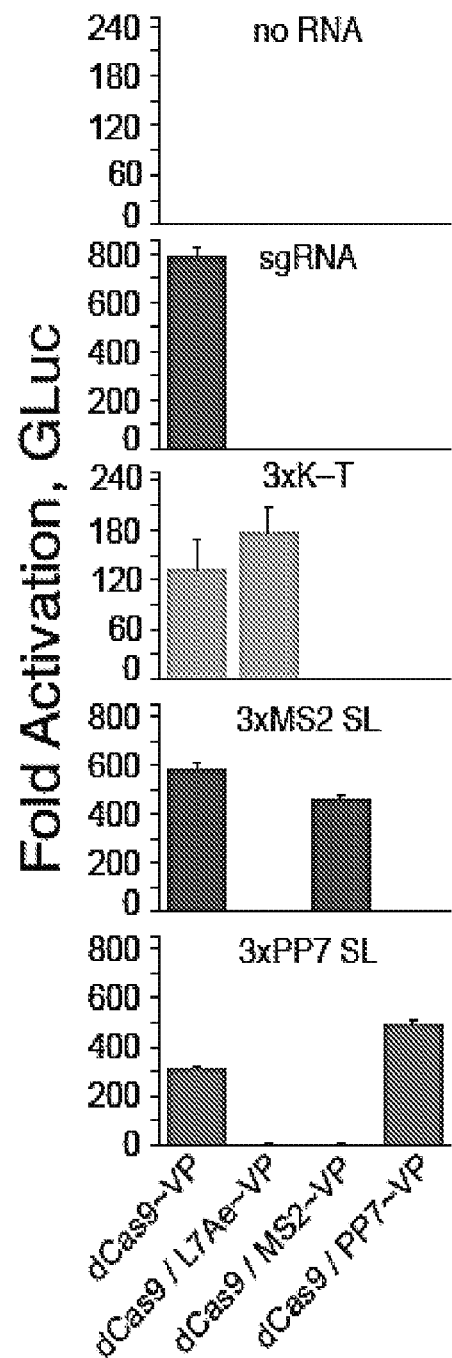
FIG. 6A-FIG. 6D are directed to guide RNA expanding the functional repertoire of CRISPR-based methods enabling modular, simultaneous control of multiple functions.

Lentiviral particles were generated using standard second generation packaging plasmids, in 293T cells. Integrated reporter cells were generated as follows: 250,000 HEK 293FT cells were plated per well of a gelatinized six-well dish and incubated overnight. Growth media was thereafter removed; cells were washed once in warmed PBS, and supplied with 1.7 mL fresh warmed media supplemented with 200 µL CLuc reporter lentivirus and 8 µg/mL polybrene. After 24 hours this process was repeated with a second dose of CLuc virus. Cells were subsequently passaged onto 10 cm gelatinized plates and selected with 2 µg/mL puromycin. CLuc reporter cells were then plated onto gelatinized six-well dishes and transduced with GLuc reporter lentivirus following the same transduction protocol. GLuc-transduced cells were not selected with hygromycin prior to use. A lentiviral variant of the EF1α-dCas9 construct shown in FIG. 1C was also used for aptamer-based imaging results of which are shown in FIG. 6C following the same transduction protocol without antibiotic selection. To enrich for cells that expressed low levels of dCas9, GLuc reporter, U6-INT and PP7~VP plasmids were transiently transfected, as in analytical luciferase assays, and collected GLuc$^+$ cells by FACS.

Figure 2A:
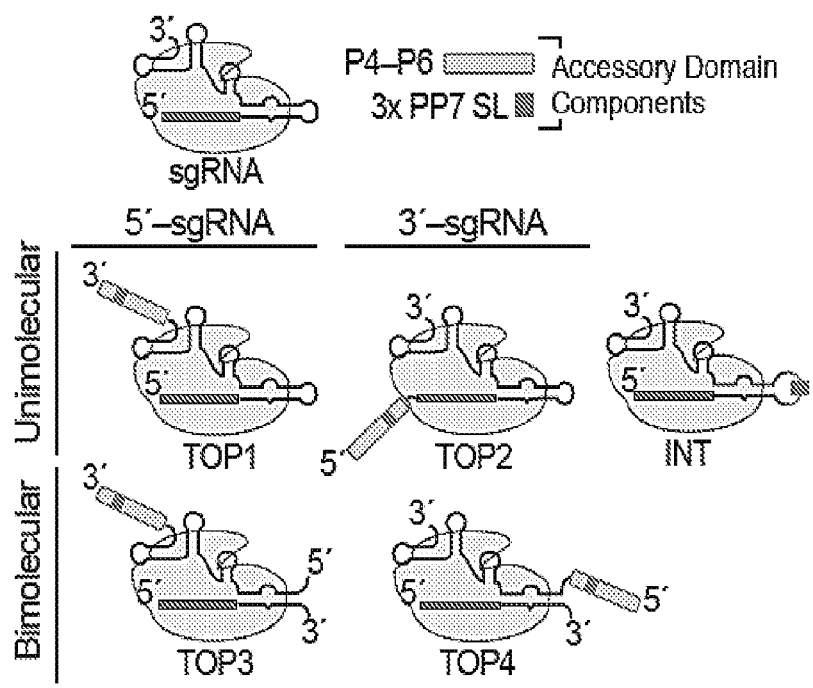
FIG. 2A-FIG. 2F are directed to large structured RNA domains which can be functionally appended onto the sgRNA scaffold at multiple points.
Figure 2B:
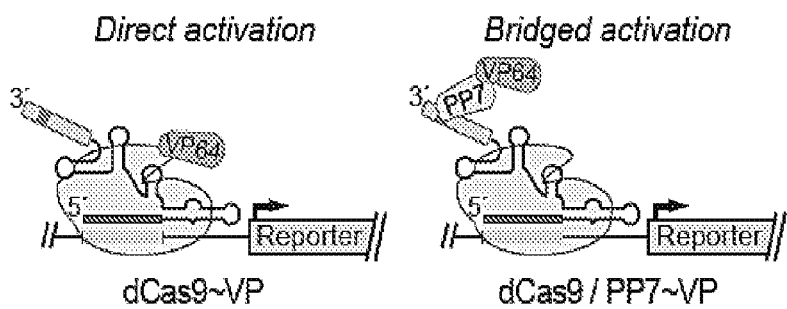
Figure 2C:
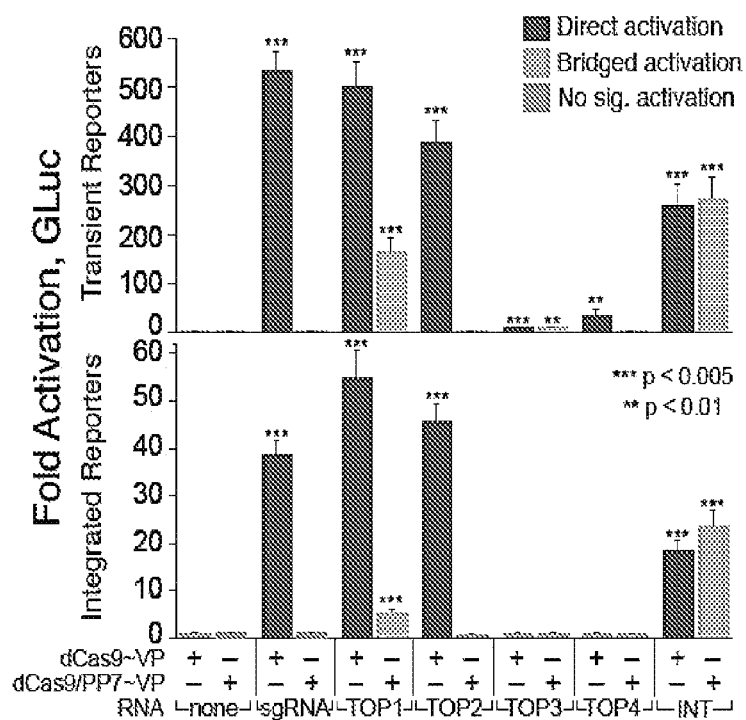
Figure 2D:
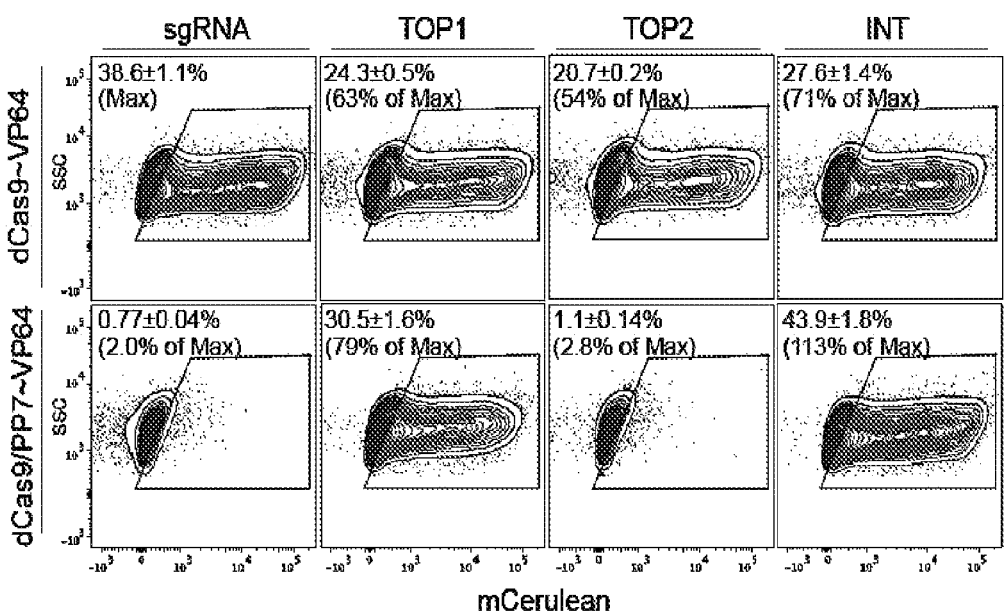
Figure 3A:
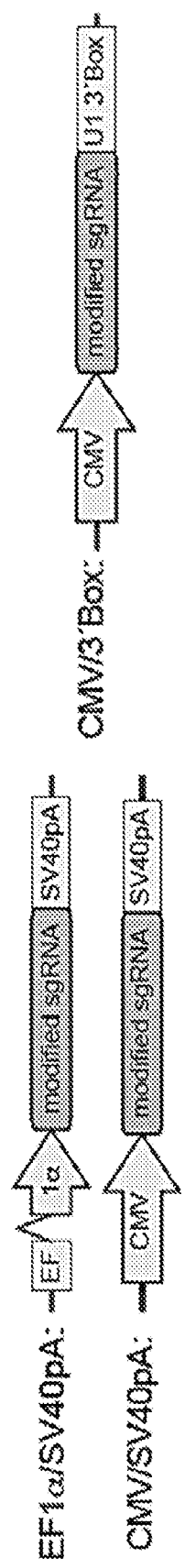
FIG. 3A-FIG. 3E are directed to CRISP/Cas complexes with guide RNAs being generated as RNA polymerase II transcripts.
Figure 11A:
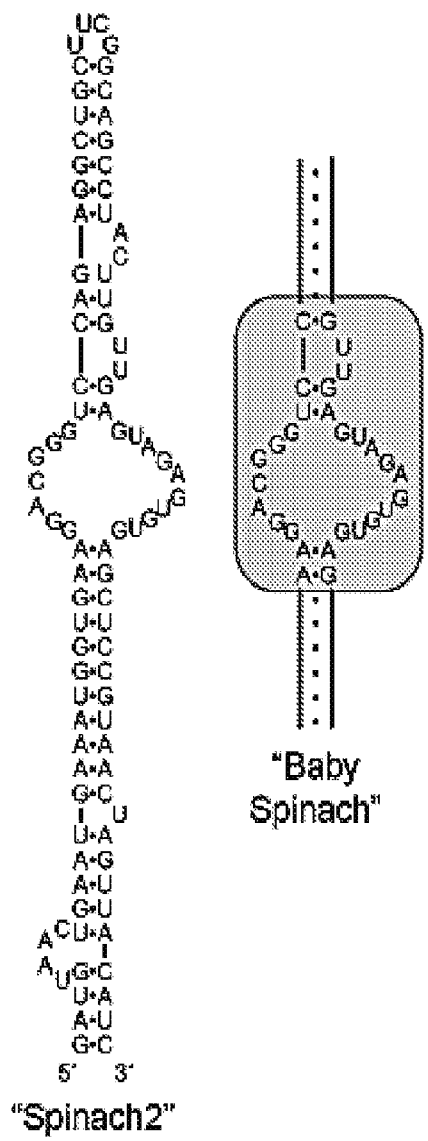
FIG. 11A-FIG. 11B (SEQ ID NO:17-19) are directed to a design of the "Bunch of Baby Spinach" (BoBS) construct.
Figure 11B:
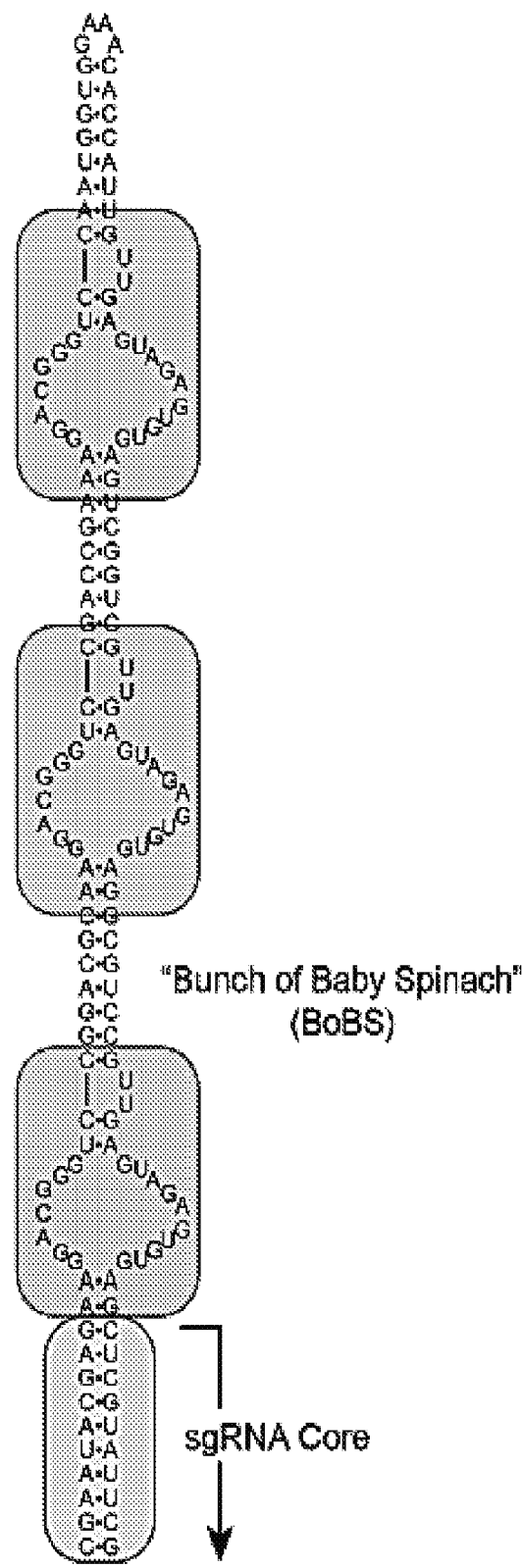

Transient transfections were performed using Lipofectamine 2000 (Life Technologies), following the manufacturer's protocol. For luciferase assays, 125,000 cells in 0.6 mL media were plated per well of gelatinized 12-well dishes and incubated overnight. Transfection mixes contained 33 ng of each luciferase reporter plasmid (where appropriate), 59 ng of dCas9 or dCas9~VP plasmid, 66 ng of PP7~VP, L7Ae~VP or MS2~VP (where appropriate), 11.6 ng of U6-driven or 542 ng of Pol II-driven sgRNA variants. For experiments using TOP3 and TOP4 as shown in FIG. 2A, 11.6 ng of a separate U6-driven gRNA plasmid was also included. For FACS data of which is shown in FIG. 2D and FIG. 3D, transfection mixes also contained 10 ng of an mCherry cotransfection control. In all cases, the total transfected plasmid mass was brought to 750 ng per well using pNEB193 (New England Biolabs) in 18 µL final volume, with 2.25 µL Lipofectamine 2000.

Figure 2E:
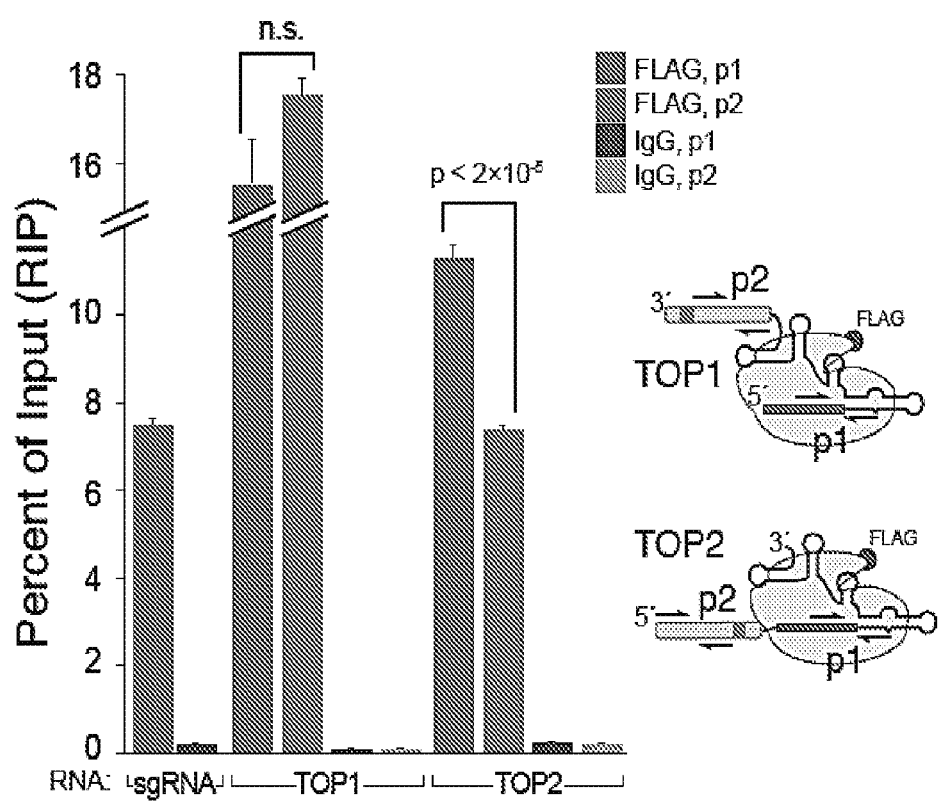
Figure 2F:
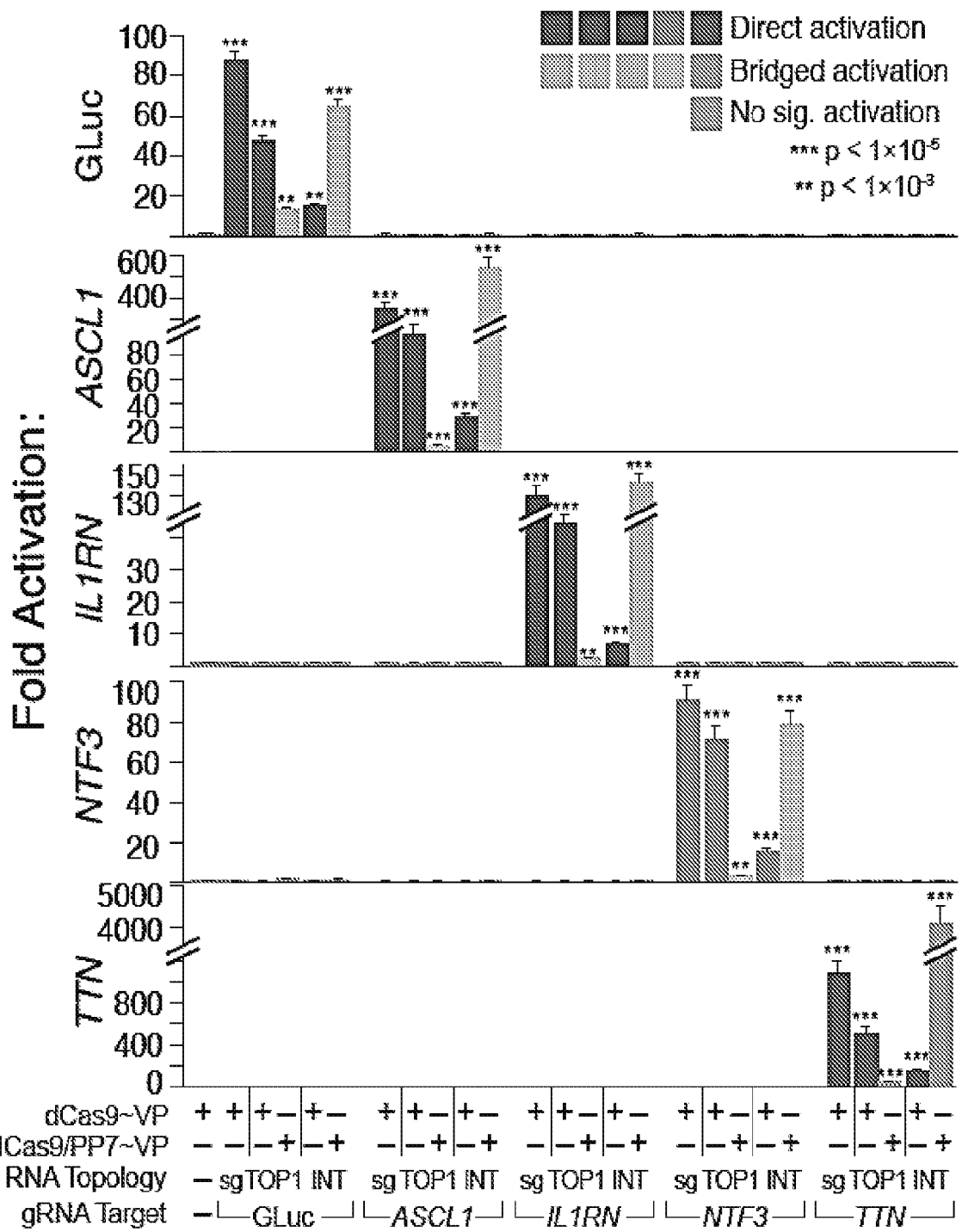

To test the modified guide RNAs including the selected RNA sequences at the identified positions of the guide RNA in a CRISPR/Cas system targeting the NTF3 locus results of which are shown in FIG. 2F, cells were plated in gelatinized 12-well dishes as in standard luciferase assays. Transfection mixes were similar to those described in Maeder, M. L. et al. CRISPR RNA-guided activation of endogenous human genes. *Nature methods* 10, 977-979 (2013), and contained 500 ng dCas9 or dCas9~VP plasmid, 500 ng GLuc-Targeting sgRNA construct or 500 ng of a mix containing equal masses (125 ng each) of four NTF3-targeting constructs. Where appropriate, 556 ng of PP7~VP plasmid was also included. All mixes were brought to 1556 ng per well using pNEB193, in 38 uL final volume, with 4.7 µL Lipofectamine 2000.

Figure 6B:
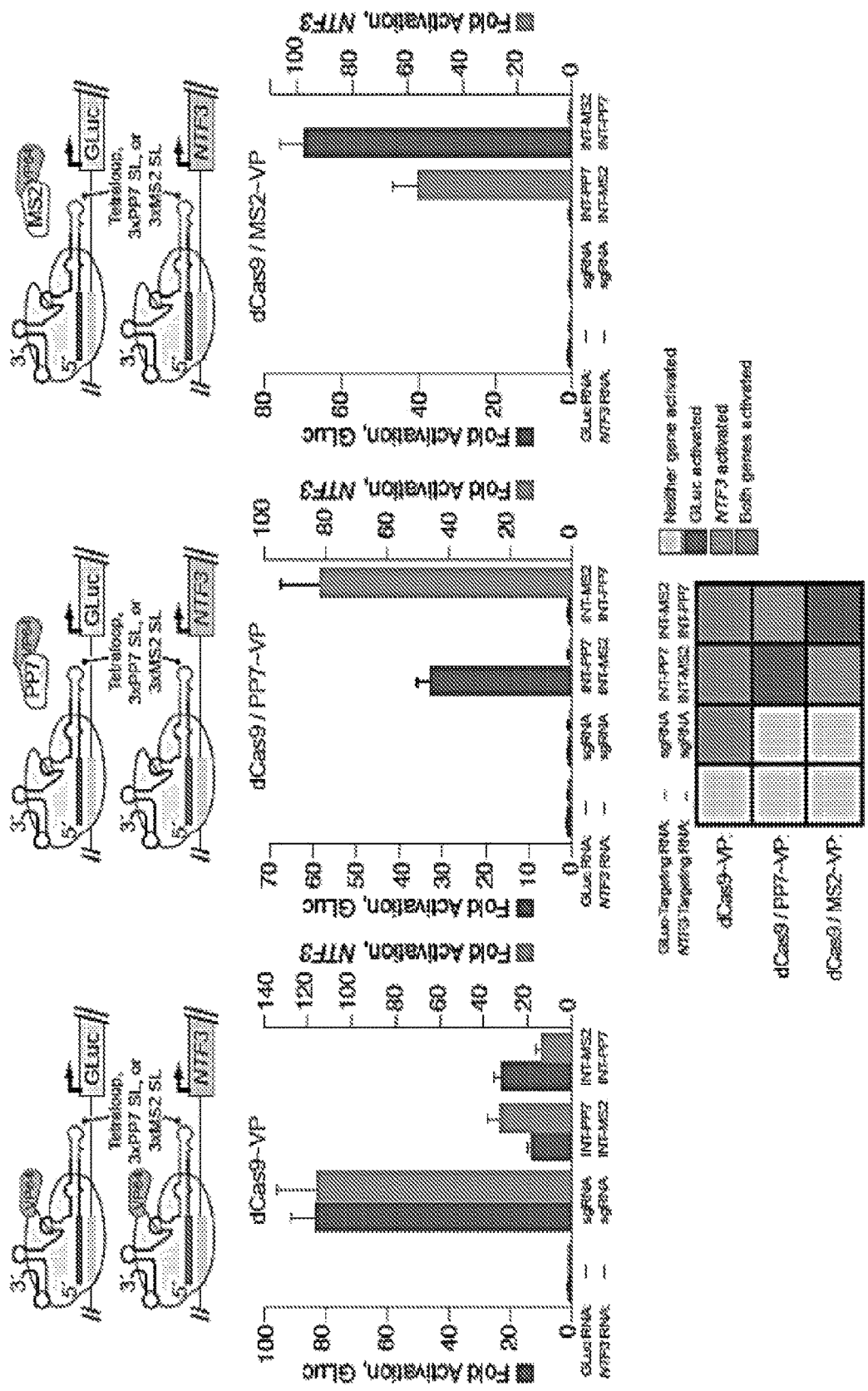
Figure 6C:
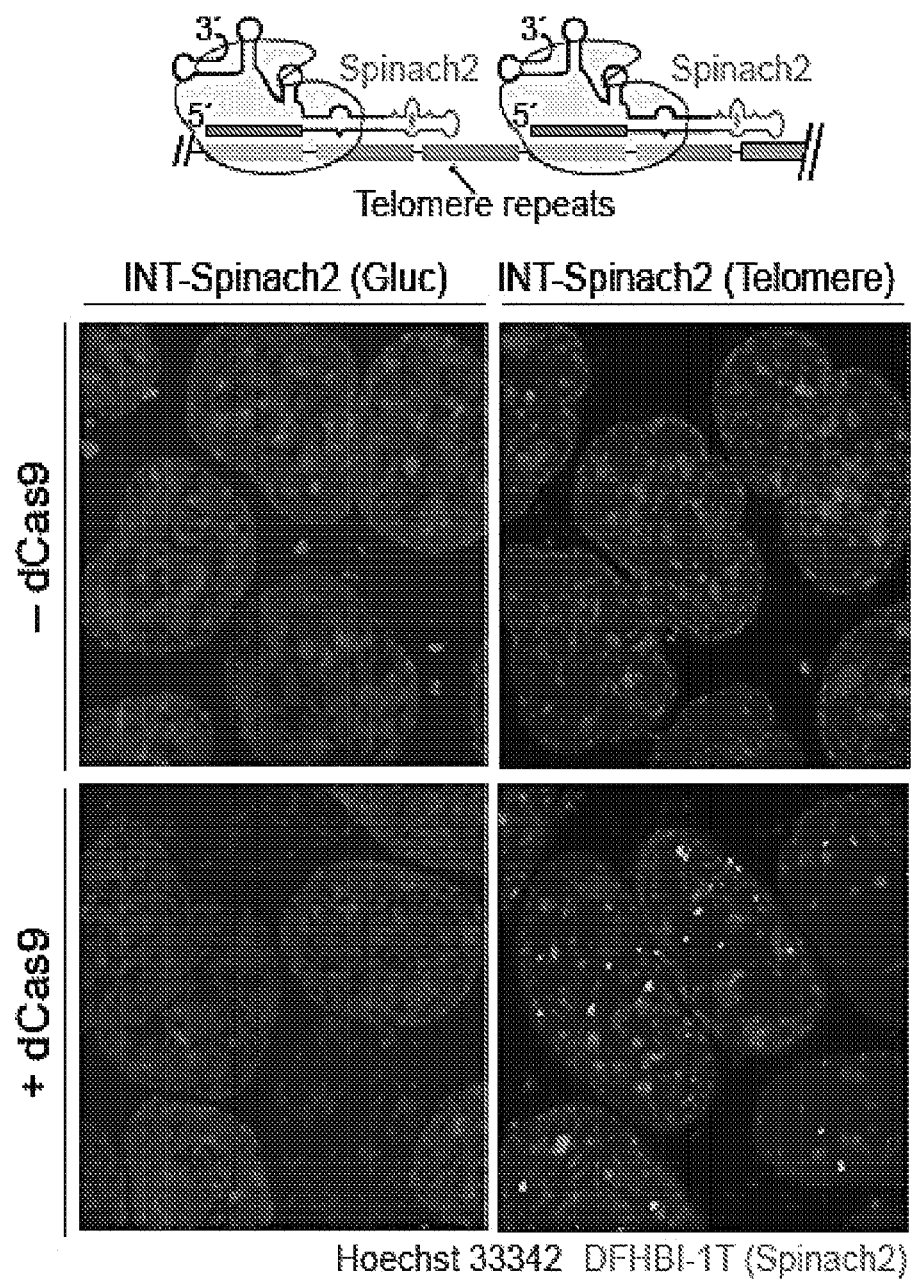

For multiplexing experiments results of which are shown in FIG. 6B, cells were plated in gelatinized 12-well dishes as above. Transfection mixes contained 250 ng dCas9 or dCas9~VP, 250 ng GLuc-targeting sgRNA variant, 250 ng of a mix containing equal masses (62.5 ng each) of four NTF3-targeting constructs, and 278 ng of PP7~VP or MS2~VP, where appropriate. In all cases the total transfected mass was brought to 1028 ng using pNEB193, in 30 µL volume, with 3.1 µL Lipofectamine 2000.

For RNA immunoprecipitation (RIP) and RIP-Seq experiments, 2.1 million cells in 10 mL growth media were plated onto gelatinized 10 cm dishes and grown overnight. Transfection mixes were as described above, but all masses and volumes were scaled 15.7-fold to account for the increase in growth area and cell number. RIP transfection mixes included each luciferase reporter to independently monitor CRISP-Disp function.

For aptamer-based imaging results of which are shown in FIG. 6C, 80,000 dCas9-transduced ("+dCas9," see above) or untransduced ("−dCas9") cells in 1 mL growth media were plated per well of Nunc Lab-Tek glass two-chamber slides (Thermo Scientific) that had been treated as follows. Wells were coated with 100 µg/mL poly-L-lysine (Millipore) overnight at 4° C. The next day, wells were washed twice with $ddH_2O$, UV sterilized for five minutes in a biosafety cabinet, coated with 100 µg/mL rat collagen-I (Corning) and 50 µg/mL laminin (Life Technologies) for two hours at 37° C., and dried prior to plating cells. Transfections were performed 24 hours thereafter, with 600 ng (telomere- or GLuc-targeting) INT-spinach2 construct, 600 ng of pNEB193 and 4.5 ng of an mCherry cotransfection control, in a total volume of 11.4 µL, with 3.8 µL Lipofectamine 2000, according to the manufacturer's protocol. Cells were imaged after 48-72 hours.

Example IV

Luciferase and FACS Assays

Luciferase assays were performed using the BioLux *Gaussia* and *Cypridina* Luciferase Assay kits (New England Biolabs), following the manufacturer's protocols. Growth media (200 µL) was harvested three days after transfection and, if not used immediately, was stored in the dark at 4° C. in parafilm-sealed 96-well dishes. 20 µL of each experimental sample was manually pipetted into black-walled 96-well plates (Corning) and assayed using a FLUOstar OPTIMA Luminometer equipped with automatic injectors (BMG Labtech). *Gaussia* and *Cypridina* assays were performed in parallel; for each, a single empirically determined gain was applied to all samples within an experimental series. Each sample was injected with 50 µL of luciferase assay buffer and mixed for two seconds prior to data acquisition. Signal was integrated over 20 seconds using an open (unfiltered) top-down optic.

For each sample, experimental raw luciferase signals were background-subtracted, and the ratio of Luciferase values, (GLuc/CLuc), was calculated. Biological replicates (at least three per experiment) were used to calculate a mean value, <GLuc/Cluc>. Fold activation was then calculated relative to a control sample in which dCas~VP was expressed in the absence of an sgRNA construct:

$$\text{Fold Activation} = \frac{\left(\frac{GLuc}{CLuc}\right)(\text{Experimental Sample})}{\left(\frac{GLuc}{CLuc}\right)(dCas9 \sim VP \text{ alone})}$$

Statistical significance testing likewise used this dCas9~VP control as the basis of comparison.

For FACS assays, cells were propagated and transfected in gelatinized 12-well dishes, as described for luciferase assays, and analyzed three days after transfection. Cells were harvested by trypsinization, quenched by the addition of chilled growth media, diluted threefold in chilled staining media (Hank's Balanced Salt Solution (HBSS, Gibco), supplemented with 2% Donor Bovine Serum (DBS, Atlanta Biologicals)), and pelleted at 200 g in a swinging bucket rotor. Cells were resuspended in chilled staining media and analyzed on a BD LSR II Flow Cytometer (BD Sciences), equipped with HcRed, CFP and YFP filters. Voltages, compensations and gates were empirically determined using unstained and single color controls, via standard methods. 100,000 mCherry$^+$ cells were recorded from each sample.

Example V

RNA Immunoprecipitation (RIP)

Cells were propagated on gelatinized 10-centimeter dishes, transfected as described above, and harvested three days after transfection. Thereafter, RIP was performed essentially as described in Kelley, D. R., Hendrickson, D., Tenen, D. & Rinn, J. L. Transposable elements modulate human gene abundance and splicing via specific RNA-protein interactions. *Genome Biology* (2014) hereby incorporated by reference in its entirety. Growth media was collected, and cells were washed twice with 10 mL room temperature PBS (Gibco). Cells were crosslinked by incubation in 0.1% (v/v) formaldehyde in PBS for 10 minutes at room temperature, under very gentle agitation. Crosslinking was quenched by the addition of Glycine to 133 mM and gentle agitation for an additional five minutes at room temperature, after which the liquid phase was aspirated. Crosslinked cells were washed twice with room temperature PBS, harvested by scraping, allotted into samples of 1×10$^7$ cells (typically three samples per 10 cm dish), and pelleted at 200 g in a swinging bucket rotor. PBS was aspirated and cell pellets were flash-frozen in liquid nitrogen and stored at −80° C. until use.

Cell pellets were thawed on ice, gently resuspended into 1 mL of ice-cold RIPA(+) buffer (standard RIPA supplemented with 0.1 U/µL RNAseOUT (Life Technologies), lx EDTA-free Proteinase Inhibitor Cocktail (Thermo Scientific) and 0.5 mM DTT), and lysed for 10 minutes at 4° C. with end-over-end agitation. Samples were then sheared using a Branson Digital Sonifier 250 (Emerson Industrial Automation) at 10% amplitude for three 30-second intervals (0.7 seconds on+1.3 seconds off), with 30-second resting steps between intervals. Samples were held in ice-cold metal thermal blocks throughout sonication. Sheared samples were then clarified by ultracentrifugation and diluted with 1 mL each of ice-cold Native Lysis Buffer(+) (25 mM Tris, pH 7.4, 150 mM KCl, 5 mM ETA, 0.5% (v/v) NP-40, supplemented with inhibitors and DTT, as above), filtered through a 0.45 µm syringe-mounted filter, and flash-frozen in liquid nitrogen before use.

Clarified lysates were thawed on ice and pre-cleared by incubation with buffer-equilibrated magnetic Protein G beads (Life Technologies) for 30 minutes at 4° C., with end-over-end rotation. 100 µL aliquots were removed and frozen, to serve as "input" normalization controls. Cleared lysates corresponding to 5×10$^6$ cells were then incubated with 6 µg rabbit anti-FLAG (SIGMA) or Rabbit normal IgG (Cell Signaling Technology), for two hours at 4° C. with end-over-end rotation. Buffer-equilibrated magnetic Protein G beads were then added and the samples were again rotated end-over-end for one hour at 4° C. Beads were collected and twice washed with Native Lysis Buffer(+) for 10 minutes at 4° C., with end-over-end rotation. Immunoprecipitated RNA was thereafter isolated as described below.

Example VI

RNA Isolation and Quantitative RT-PCR

Whole cell RNA and RNA from subcellular fractions data for which are shown in FIG. 8A-FIG. 8D were isolated by extraction with Trizol and Trizol-LS Reagent (Life Technologies), respectively, following the manufacturer's protocols. RNA was precipitated with isopropanol using GlycoBlue (Life Technologies) as a carrier, and subsequently purified using RNEasy spin columns (QIAgen), following the manufacturer's "RNA Cleanup" protocol, with on-column DNase treatment.

RNA from RIP and RIP-Seq experiments data for which is shown in FIG. 2E, FIG. 3E, FIG. 4C and FIG. 5D was isolated as follows. Following RIP (see above), protein G beads were suspended in 56 µL nuclease-free water, and processed alongside input samples (56 µL; 5.6% of the total). All samples were brought to 100 µL with 3× Reverse Crosslinking Buffer (final concentrations: 1×PBS, 2% N-Lauroyl Sarcosine, 10 mM EDTA, 5 mM DTT, 0.4 U/µL RNAseOUT and 2 mg/mL proteinase K (Ambion)). Formaldehyde crosslinks were reversed by incubation in a thermocycler at 42° C. for one hour, and then 55° C. for one hour. RNA was thereafter purified using four volumes (400 µL) Agencourt RNAClean XP Beads (Beckman Coulter), following the manufacturer's protocol, and eluted into 30 µL nuclease-free water. Residual DNA was removed by treatment with 5 U RNase-free DNAs (RQ1, Promega) in 50 µL, following the manufacturer's protocol. RNA was subsequently purified using four volumes (200 µL) Agencourt RNAClean XP beads, eluted into 20 μL nuclease-free water, and stored at −20° C. until use.

cDNA was synthesized using SuperScript III Reverse Transcriptase (Life Technologies), according to the manufacturer's protocol, priming from anchored oligo-dT$_{21}$, random hexamers (Life Technologies) or a gene specific primer (Integrated DNA Technologies), where appropriate. Target RNA abundance was quantified by qRT-PCR on a 7900HT Fast Real-Time PCR System (Applied Biosystems), using Rox-normalized FastStart Universal SYBR Green Master Mix (Roche) and gene-specific primers shown in Table 3, in quadruplicate. Non-reverse-transcribed RNA was used as a negative control. "Clipped" data were processed using Real-time PCR Miner (see Zhao, S. & Fernald, R. D. Comprehensive algorithm for quantitative real-time polymerase chain reaction. *Journal of computational biology: a journal of computational molecular cell biology* 12, 1047-1064 (2005) hereby incorporated by reference in its entirety), to calculate $C_T$ and primer efficiency values. Bulk gene expression measurements data for are shown in FIG. 2F and FIG. 6B were normalized to a GAPDH internal control; RIP measurements were normalized to input RNA levels. In subcellular fractionation experiments data for which are shown in FIG. 8C and FIG. 8D, the yield of RNA in each compartment was quantified relative to the unfractionated input level, as in RIP experiments. Data analysis was performed using standard methods.

Example VII

Error Propagation

For Luciferase and qRT-PCR assays, experimental uncertainties were propagated as follows. Namely, given S, the sum or difference of values A, B, uncertainty was calculated using the formula:

$$\sigma_S = \sqrt{(\sigma_A)^2 + (\sigma_B)^2}$$

wherein $\sigma_A$ and $\sigma_B$ are the measurement errors of A and B, respectively. For P, the product or quotient of values A and B, uncertainty was calculated using the formula:

$$\sigma_P = P \times \sqrt{\left(\frac{\sigma_A}{A}\right)^2 + \left(\frac{\sigma_B}{B}\right)^2}$$

The uncertainty of other functions, F(x), was calculated using the first derivative approximation:

$$\sigma_{f(x)} = \sigma_x \times f'(x)$$

Example VIII

Subcellular Fractionation

Figure 8A:
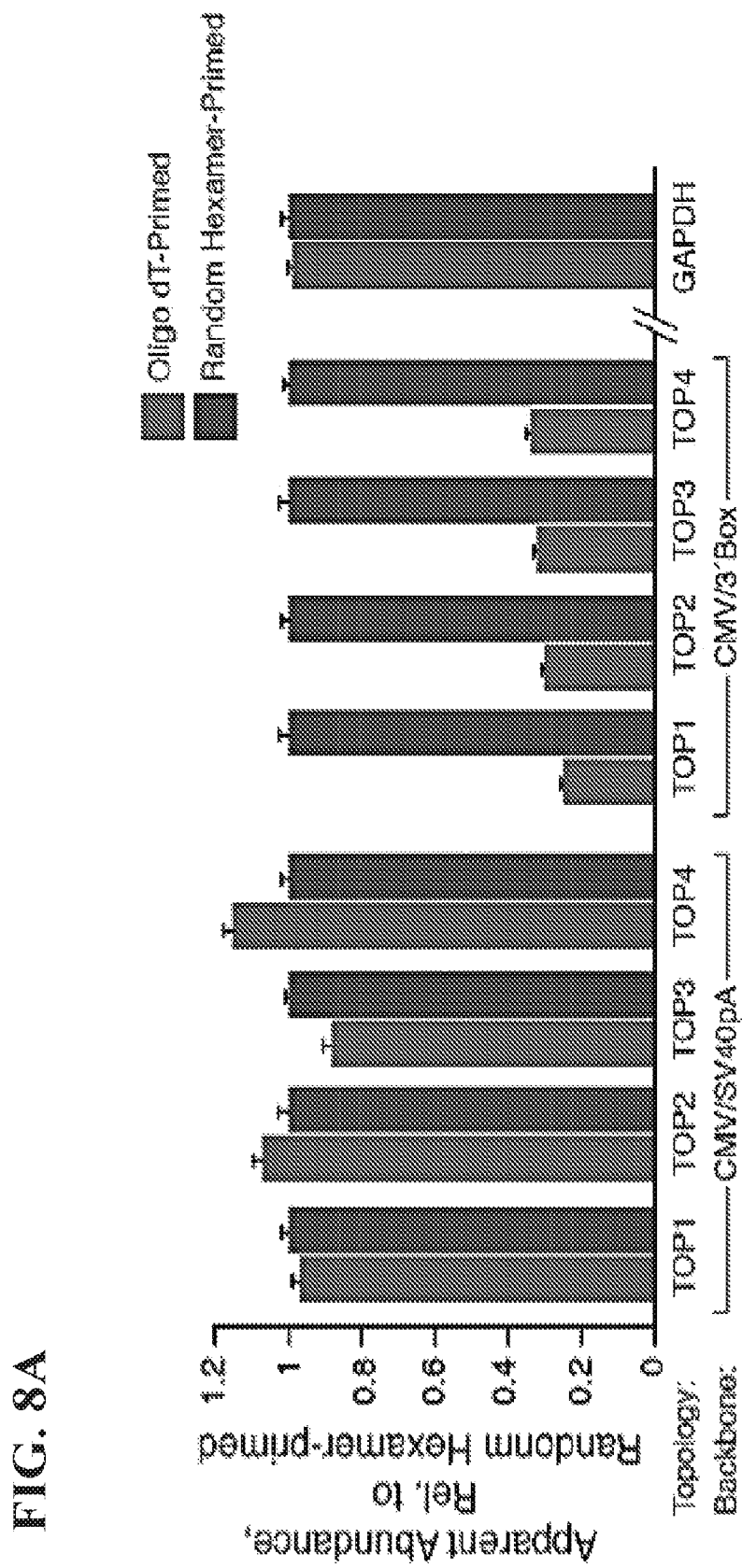
FIG. 8A-FIG. 8D are directed to the CMV/3'Box system generating non-polyadenylated, nuclear-localized transcripts.
Figure 8B:
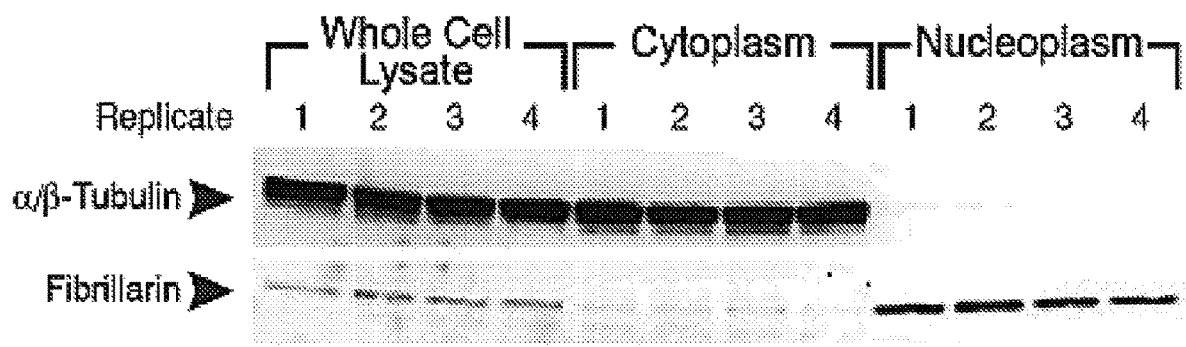
Figure 8C:
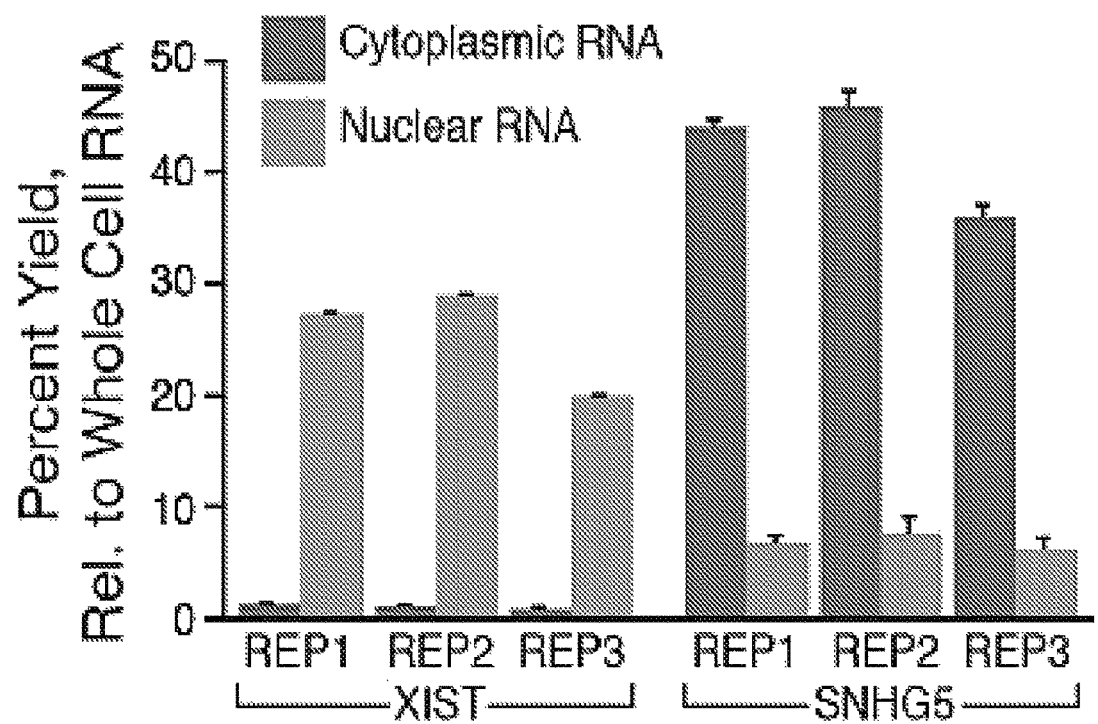
Figure 8D:
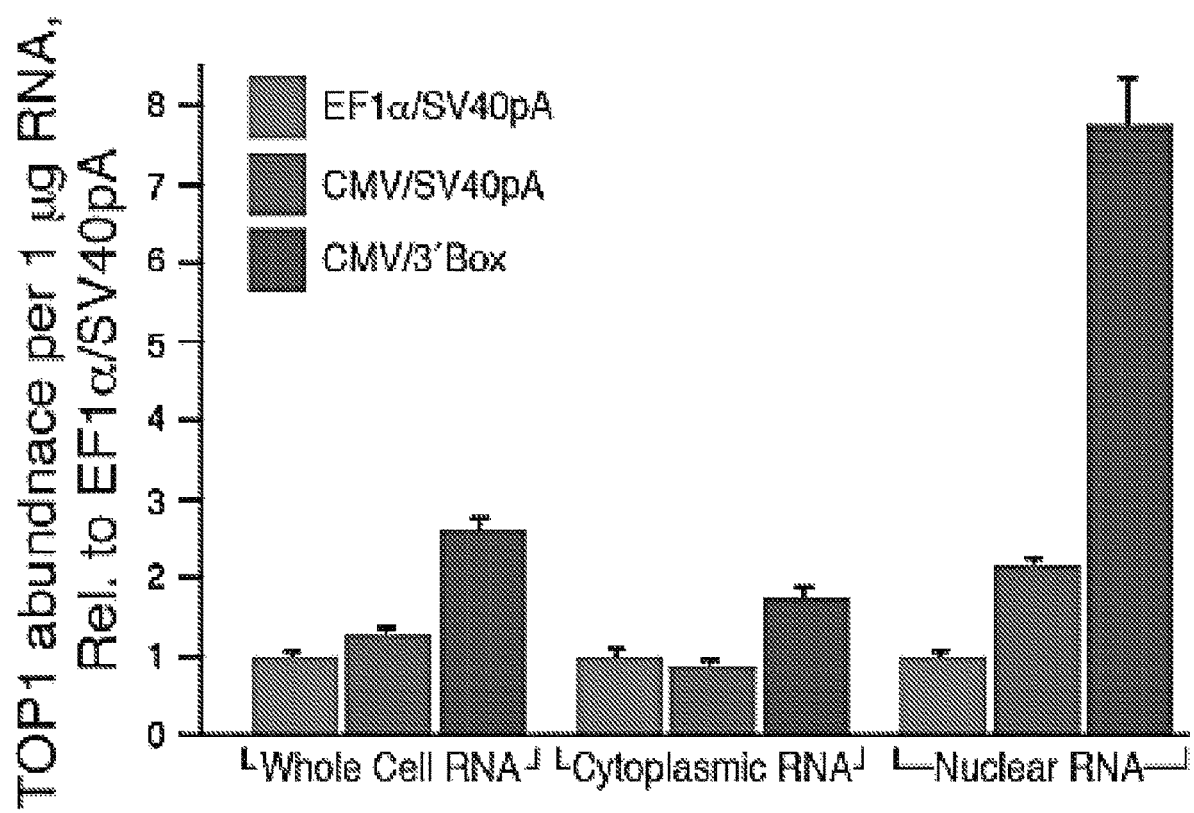

Cytoplasmic and nuclear fractions data for which are shown in FIG. 8B, FIG. 8C, and FIG. 8D were isolated as described in Rosner, M. & Hengstschlager, M. Detection of cytoplasmic and nuclear functions of mTOR by fractionation. *Methods in molecular biology* 821, 105-124 (2012); and Bhatt, D. M. et al. Transcript dynamics of proinflammatory genes revealed by sequence analysis of subcellular RNA fractions. *Cell* 150, 279-290 (2012) each of which is hereby incorporated by reference in its entirety. Briefly, cells were grown and transfected in gelatinized 10-cm dishes, as described for RIP experiments, above. Three days after transfection, cells were harvested by trypsinization, quenched with growth media, pelleted and washed thrice with ice-cold PBS. Cells were gently resuspended in five packed cell pellet volumes ("cv's") of ice-cold Cyto Extract Buffer(+) (20 mM Tris, pH 7.6, 0.1 mM EDTA, 2 mM MgCl$_2$, supplemented with 0.5 U/μL RNAseOUT and 1×EDTA-free Proteinase Inhibitor Cocktail), and swollen by incubation at room temperature for two minutes, and on ice for ten minutes more. Cells were then lysed by addition of CHAPS to 0.6% final, gentle pipetting, and two passages through a syringe equipped with a 20G needle. Lysate was clarified by centrifugation at 500 g in a tabletop microcentrifuge at 4° C.; 70% of the resulting supernatant was retrieved as the cytoplasmic fraction. The pellet, corresponding to nuclei and cell debris, was washed twice by gentle resuspension into five cv's of Nuclear Wash Buffer(+) (Cyto Extract Buffer, supplemented to 0.6% CHAPS and with inhibitors, as above), followed by centrifugation at 500 g. Washed nuclei were gently resuspended into two cv's of Nuclei Resuspension Buffer(+) (10 mM Tris, pH 7.5, 150 mM NaCl, 0.15% (v/v) NP-40, supplemented with inhibitors, as above) layered onto a cushion of five cv's Sucrose Buffer(+) (10 mM Tris, pH 7.5, 150 mM NaCl, 24% (w/v) Sucrose, plus inhibitors), and pelleted at 14,000 rpm in a tabletop microcentrifuge at 4° C. The resulting pelleted nuclei were resuspended into two cv's of ice-cold PBS and pelleted at 500 g. Fractionation success was confirmed by two methods: western blotting and qRT-PCR. In western blots, aliquots of whole cell lysate, the cytoplasmic fraction and PBS-suspended nuclei were probed using antibodies against (α/β)-Tubulin and Fibrillarin (Cell Signaling Technology). For qPCR, extracted RNA (see above) was quantified using primers against the cytoplasmic ncRNA SNHG5 and the nuclear ncRNA Xist.

Example IX

N$_{25}$ RNA Library Preparation, Sequencing and Analysis

Figure 5A:
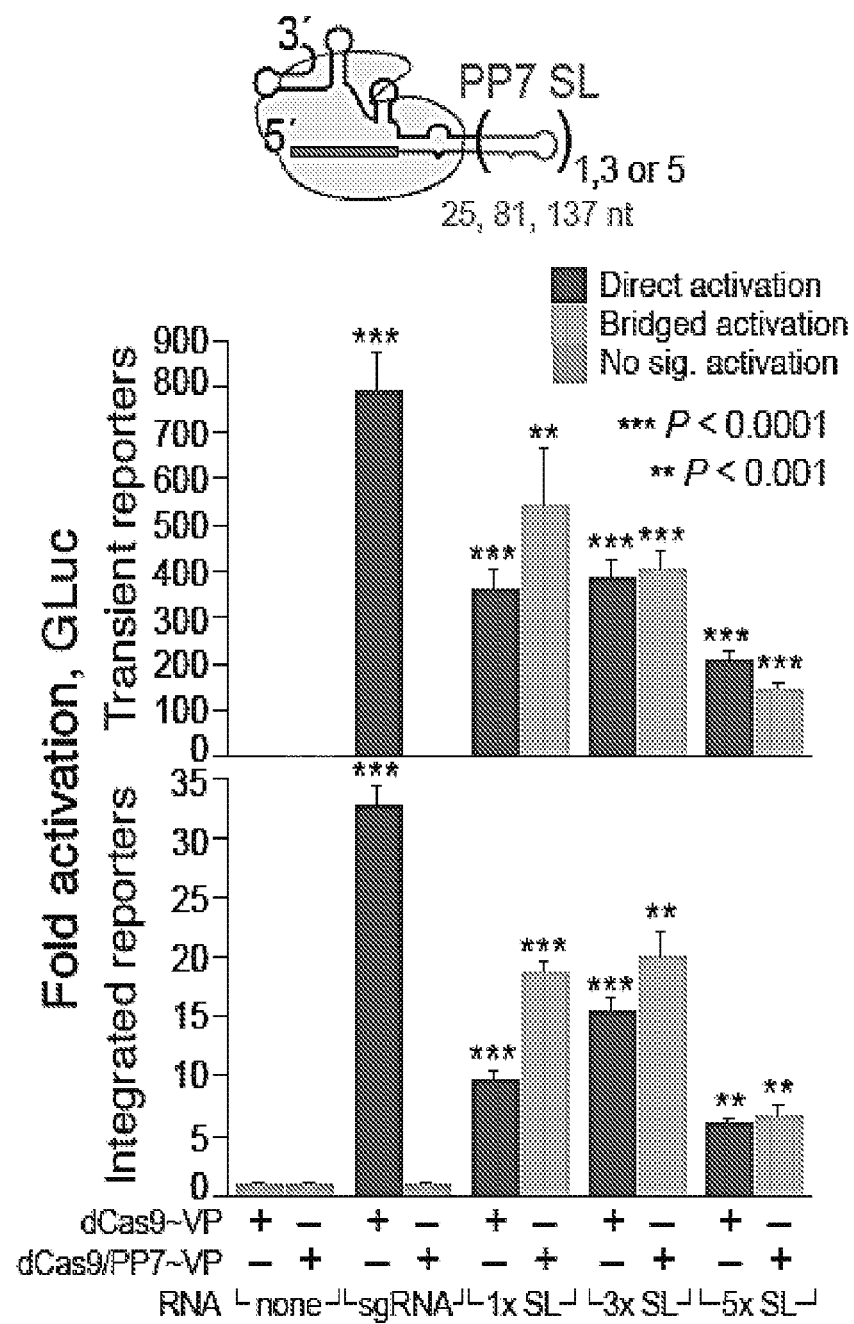
FIG. 5A-FIG. 5E are directed to guide RNA with a compendium of structurally diverse RNA domains.
Figure 5B:
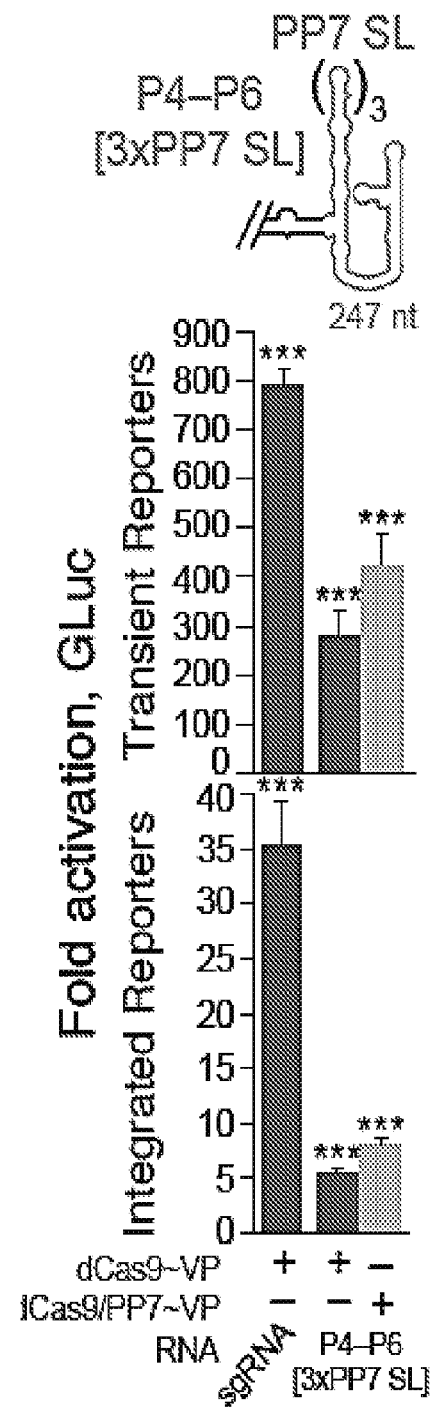
Figure 5C:
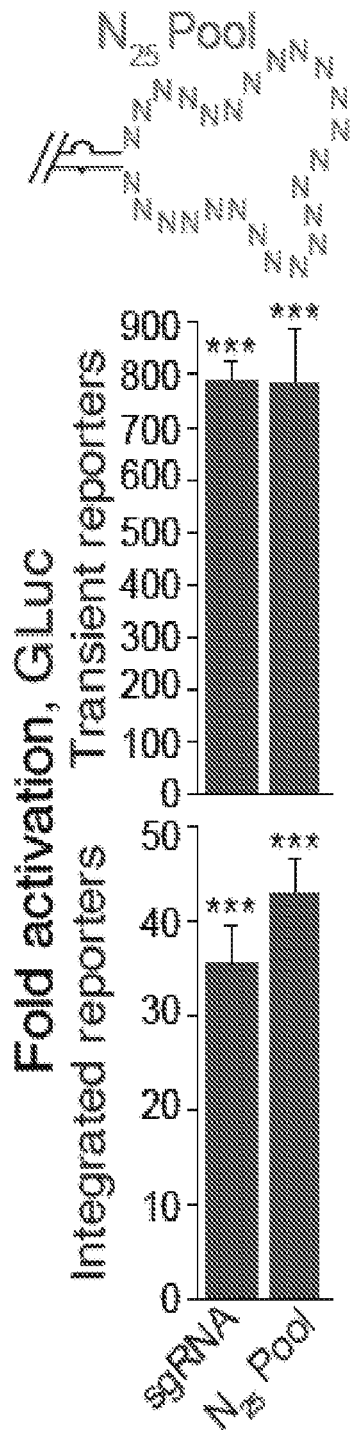
Figure 5D:
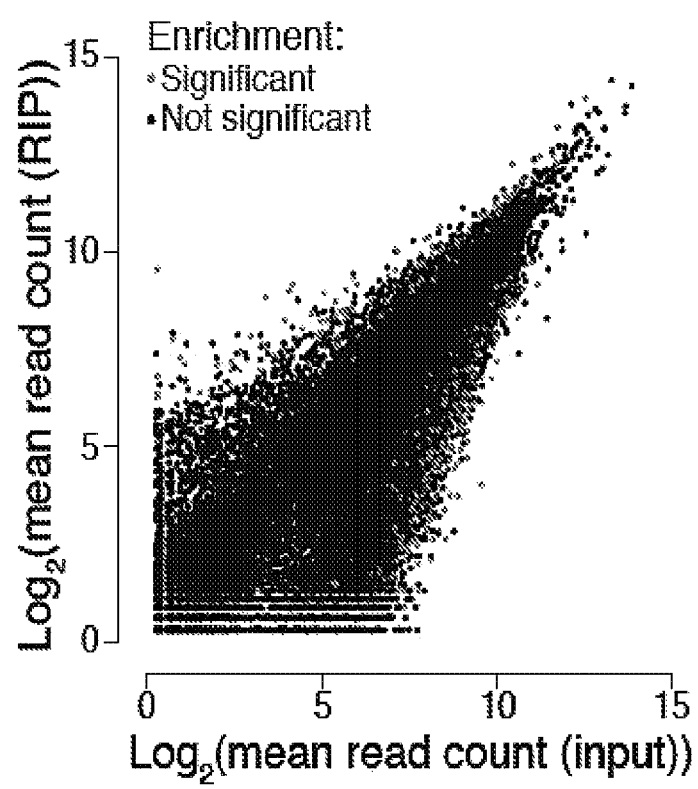
Figure 9C:
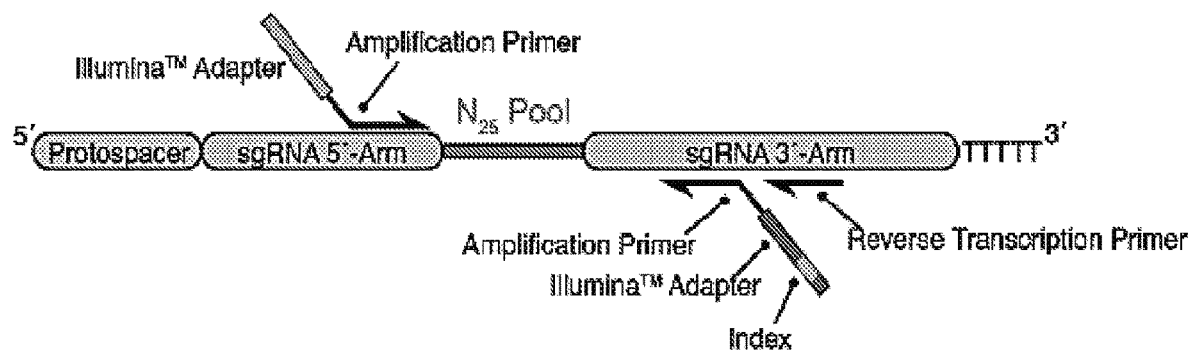
Figure 9D:
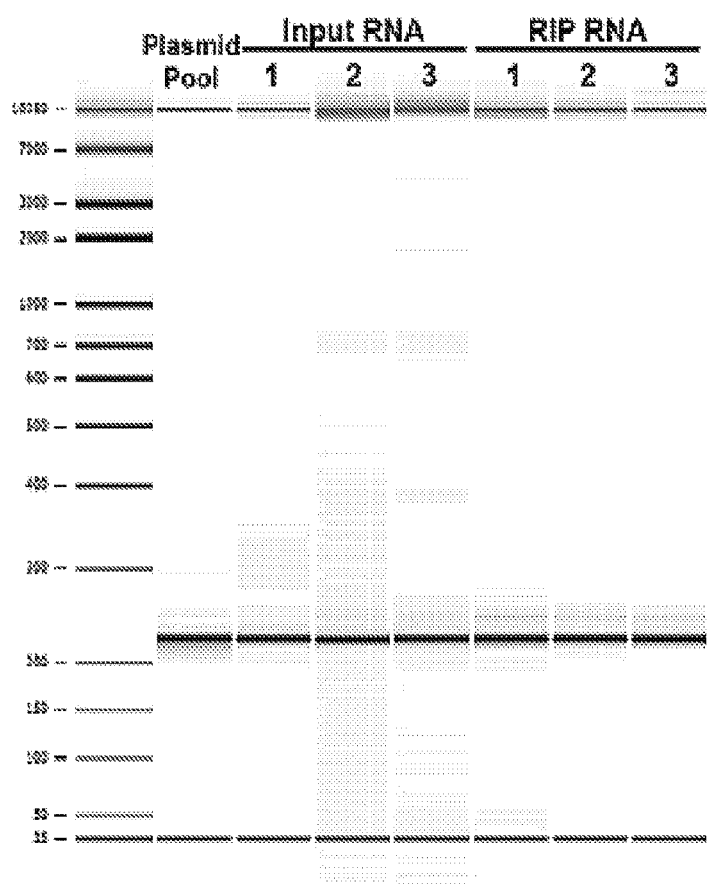
Figure 10A:
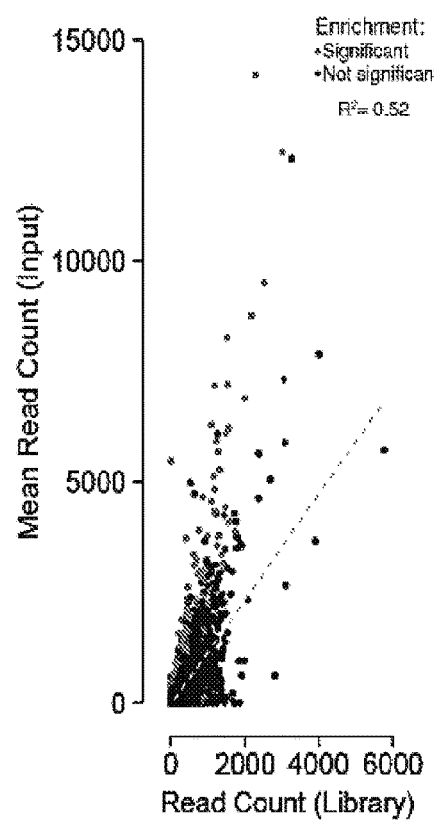
FIG. 10A-FIG. 10C are directed to deep sequencing data.
Figure 10B:
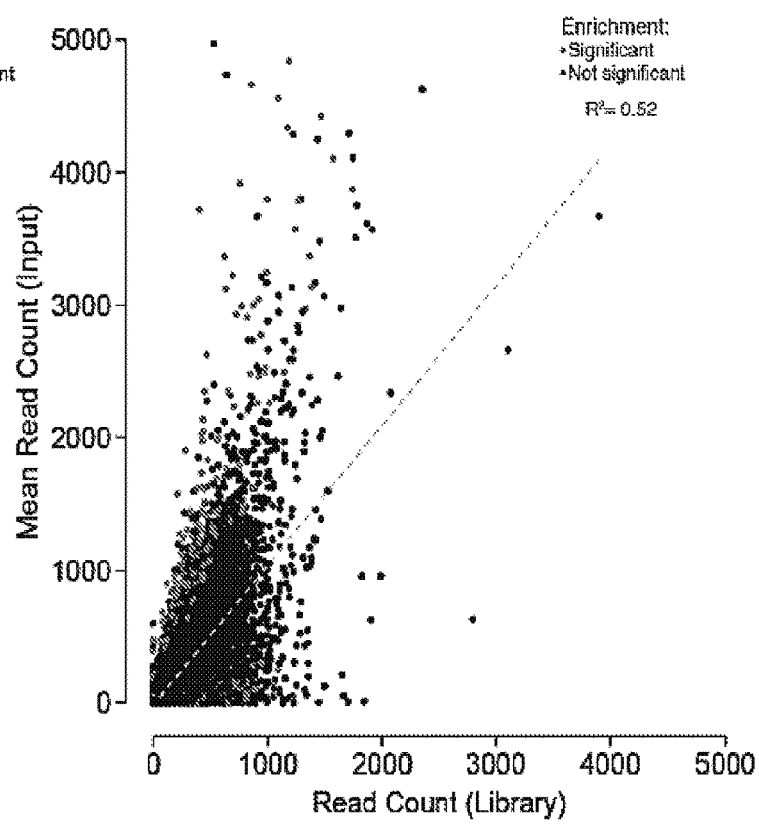
Figure 10C:
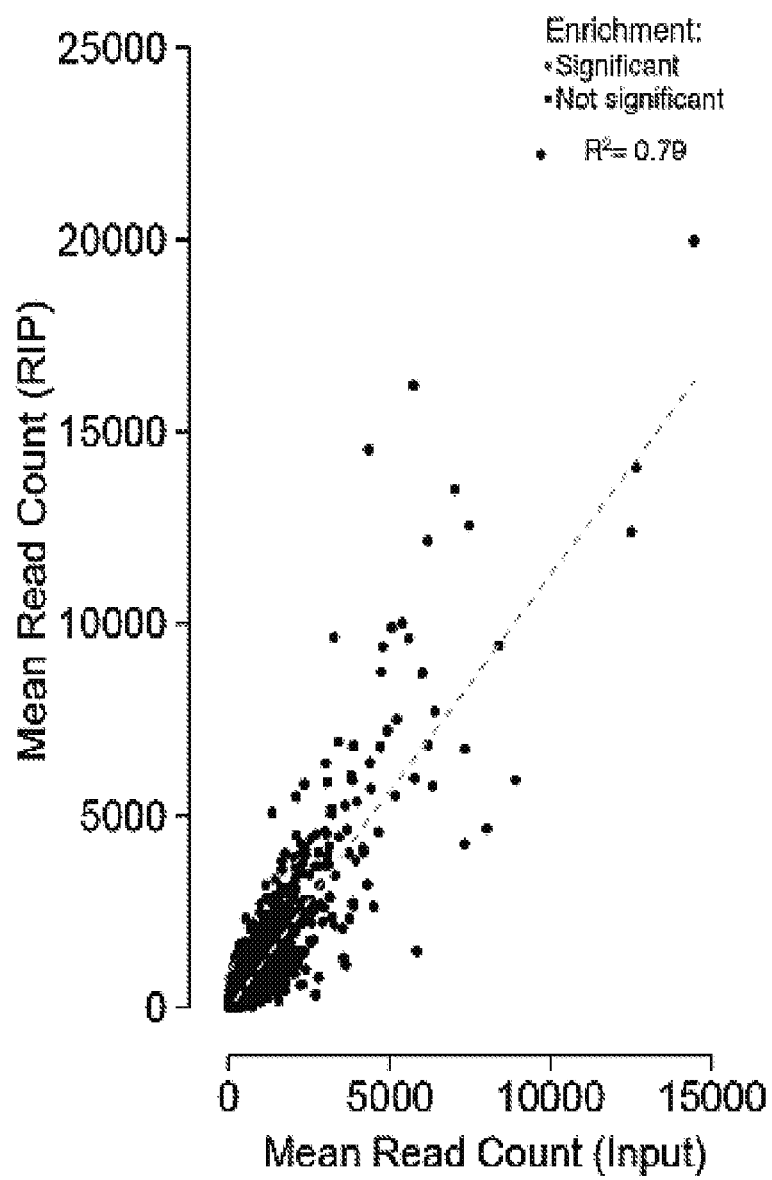

For the N$_{25}$ RIP-Seq experiment data for which is shown in FIG. 5D, cell growth, transfection, RIP and RNA preparation were performed as described above, in triplicate. Seven deep sequencing libraries were prepared: one from the starting plasmid pool, three from replicates of the input RNA, and three from replicates of the immunoprecipitated RNA. The plasmid pool library was generated directly via PCR, using 5 ng of plasmid template in a 50 μL reaction, amplified through 19 cycles of PCR with Pfu Ultra II HS polymerase (Agilent), according to the manufacturer's protocol. Gene-specific PCR primers that bracketed the N$_{25}$ insertion site, appended with standard Illumina adapters and indexes, were used as shown in Table 4 and FIG. 9C. For each input and RIP library, 10 ng RNA was reverse-transcribed in 20 μL as described above, using a gene specific primer. Each cDNA reaction was used in its entirety as PCR template, using the same primer design as was used for the plasmid pool, but with different Illumina indexes. The pools were amplified in 200 μL, through 26 cycles of PCR with Pfu Ultra II HS polymerase (Agilent), according to the manufacturer's protocol. The resulting deep sequencing libraries were purified twice with 1.0 volume of Agencourt AMPure XP Beads (Beckman Coulter), according to the manufacturer's protocol, and eluted in EB Buffer (QIAgen). The plasmid pool library contained traces of high molecular weight contaminants (not shown) that were removed by "reverse selection:" the sample was treated with 0.65 volumes of AMPure XP Beads, and the unbound fraction was retained. The integrity and concentration of each final library was measured using a "DNA High Sensitivity" assay on an Agilent 2100 model Bioanalyzer, gel images of which are shown in FIG. 9D.

Libraries were denatured in 50 mM NaOH, diluted in buffer HT1 (Illumina) and combined to yield a 20 pM pool, according to standard protocols. This pool was doped with TailorMix Indexed PhiX Control Library (SeqMatic), at a ratio of 7:3 $N_{25}$:PhiX, and sequenced on two lanes of an Illumina HiSeq 2500 (FAS Center for Systems Biology, Harvard) for 150 cycles, followed by 25 cycles of indexing.

Random insert sequences were extracted from raw sequencing reads by removing the constant sequences abutting each side of the insertion point. The number of occurrences of each random sequence within each individual sample was then tabulated. Sequence counts were used to calculate enrichment using DESeq2 (see Anders, S. & Huber, W. Differential expression analysis for sequence count data. *Genome Biol* 11, R106 (2010) hereby incorporated by reference in its entirety).

Example X

Live Cell Imaging

Figure 1C:
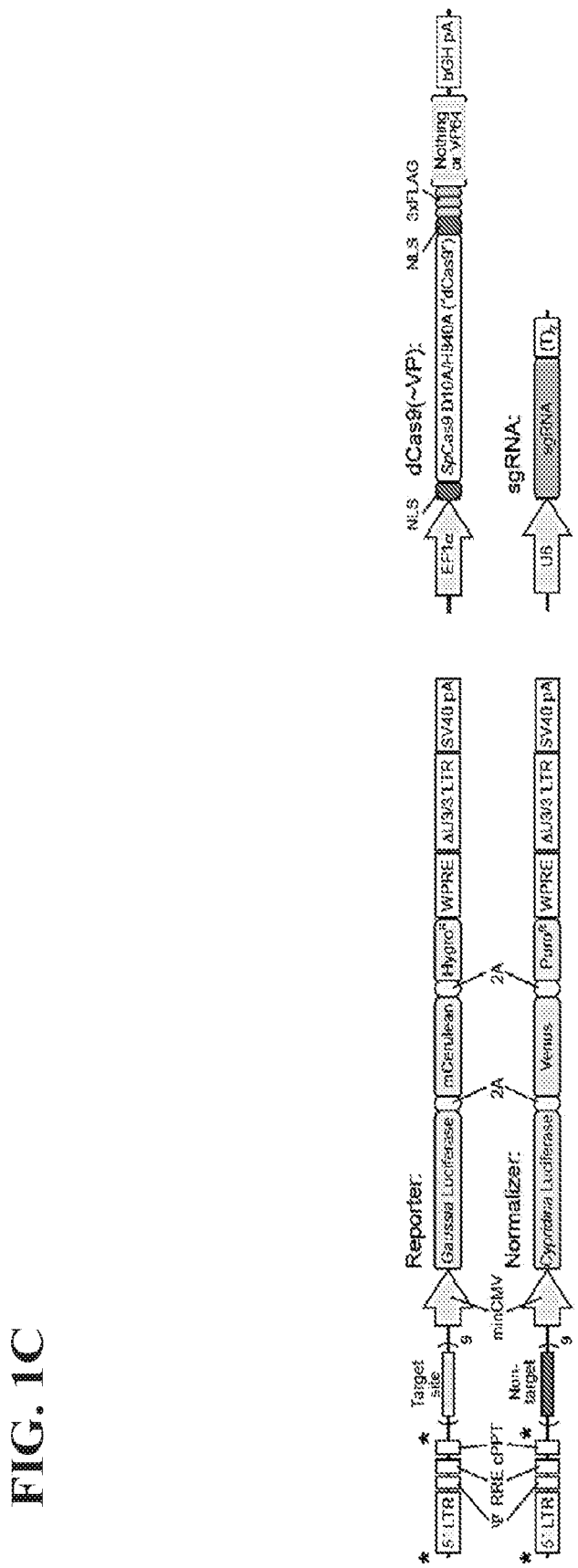
Figure 1D:
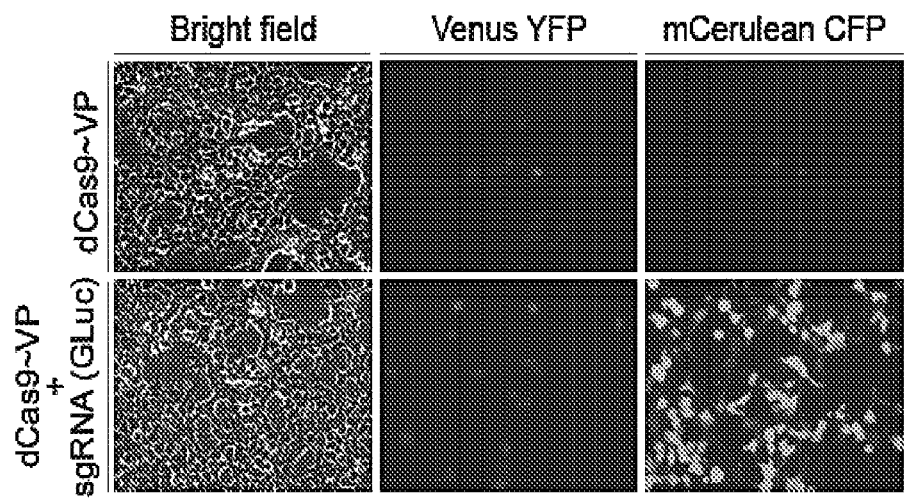

Images such as those shown in FIG. 1D were collected on an Axio Observer D1 system (Zeiss), equipped with eYFP and eCFP filters.

In bridged imaging experiments, images were taken with an LSM 700 Inverted Confocal Microscope (Harvard Center for Biological Imaging), with an aperture setting of 1 A.U., using the DAPI filter for Hoechst 33342, the CFP filter for mCerulean and the mCherry filter for mCherry. Cells were imaged two days post-transfection, in their growth media. Images are max-merges of 37-47 Z-stacks, taken with a step size of 0.33 μm, at 63× magnification. See FIG. 15.

For aptamer-based imaging, such as that shown in FIG. 6C, growth media was replaced with imaging media (Fluorobrite DMEM (Life Technologies), 25 mM HEPES, 5 mM MgSO4, 1 μg/ml Hoechst 33342 (Life Technologies), and 20 μM DFHBI-1T (Lucerna)) for 30 minutes at 37° C. Live fluorescence imaging were taken with an LSM 700 Inverted Confocal Microscope (Harvard Center for Biological Imaging), with an aperture setting of 1 A.U., using the FITC filter for DFHBI-1T and DAPI filter for Hoechst 33342. Images in are max-merges of 20-30 Z-stacks, taken with a step size 0.35 μm, at 63× magnification.

Example XI

CRISPR Transcription Activator Reporter Assay

According to one aspect, a reporter assay in HEK293FT cells, modeled after established transcription activator reporter systems (see Gilbert, L. A. et al. CRISPR-mediated modular RNA-guided regulation of transcription in eukaryotes. *Cell* 154, 442-451 (2013) and Zhang, F. et al. Efficient construction of sequence-specific TAL effectors for modulating mammalian transcription. *Nature biotechnology* 29, 149-153 (2011) each of which are hereby incorporated by reference in its entirety) was used and is shown in FIG. 1C. The reporter assay includes two mammalian expression constructs—reporter and normalizer—that encode mutually orthogonal pairs of fluorescent proteins and secreted luciferases, preceded by arrays of short "target" and "non-target" motifs as illustrated in FIG. 1B and with sequences provided in Table 1. If binding an artificial transcription activator (protein, RNA or RNP) to the target motifs induces reporter expression, the effect can be monitored via FACS as an increase in the population of mCerulean+ cells, or via luminometry as in increase in the bulk luciferase activity. The system can be transiently transfected, wherein it exhibits extremely high sensitivity, or stably integrated into the host chromatin through lentiviral transduction, wherein it better approximates the behavior of endogenous genes.

Figure 1E:
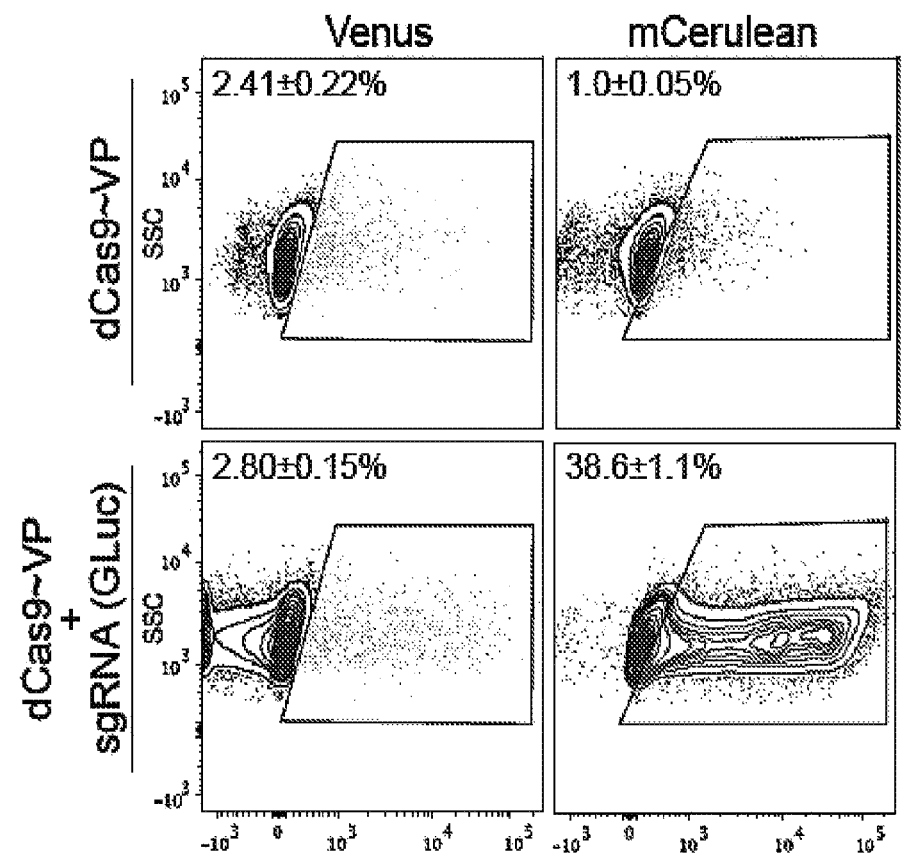
Figure 1F:
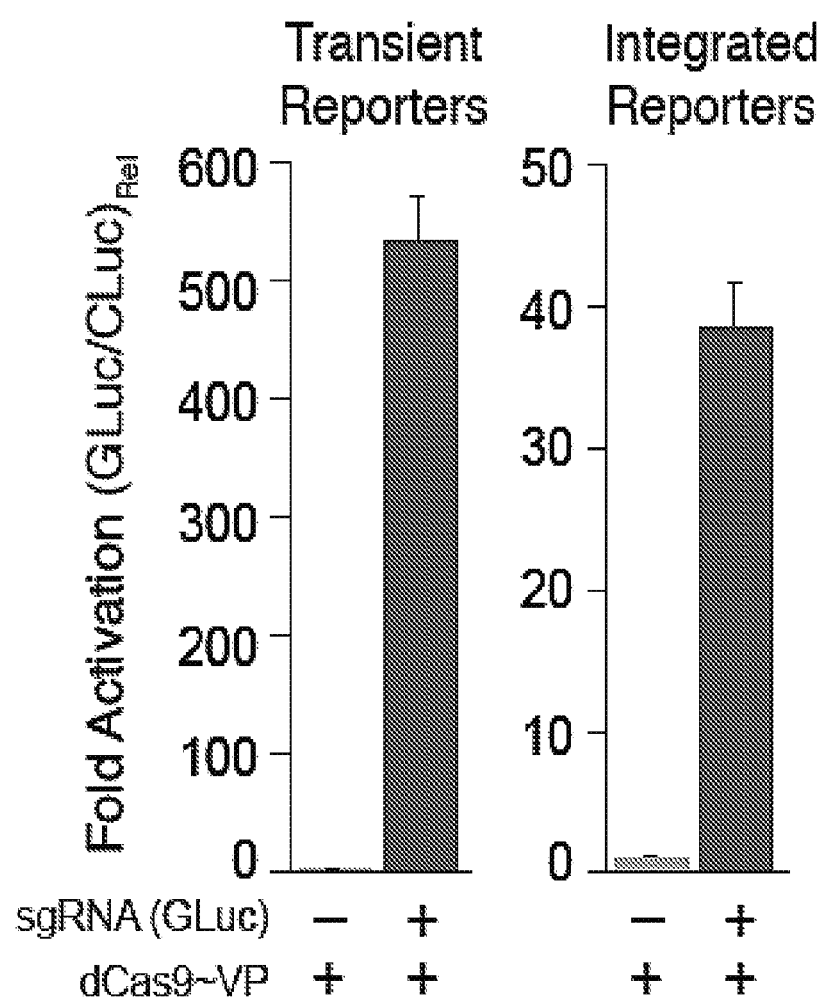

According to one aspect, the *S. pyogenes* CRISPR-Cas9 system is used, which intrinsically couples its DNA- and RNA-binding activities. Indeed, a nuclease-deficient Cas9 mutant (dCas9), fused to the VP64 transcription activator (dCas~VP) robustly activated the reporter system in an RNA-dependent manner. In transient reporter assays, coexpression dCas9~VP with a standard GLuc-targeting sgRNA (sgRNA-GLuc), increased the population of mCerulean+ cells ~40-fold, relative to dCas9~VP alone, data for which is shown in FIG. 1D and FIG. 1E. This concomitantly induced >500-fold activation in normalized luciferase signal, data for which is shown in FIG. 1F, left. Critically, parallel results were obtained with stably integrated reporters, which exhibited ~39-fold sgRNA-dependent GLuc activation, data for which is shown in FIG. 1F, right.

Example XII

Adapting CRISPR-Cas9 as an RNA Display Device

Figure 7C:
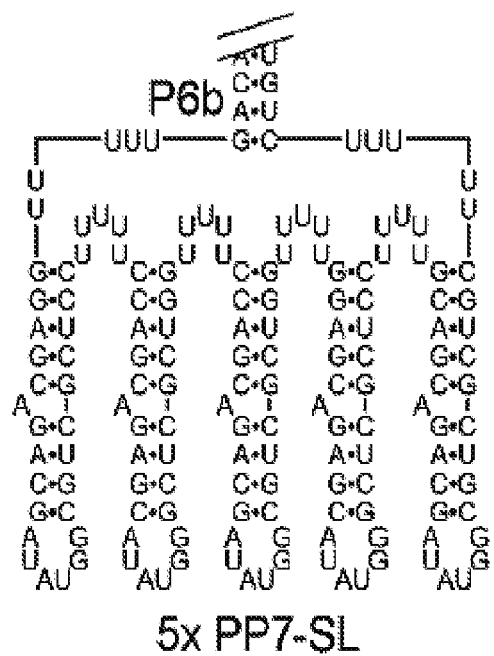
Figure 7D:
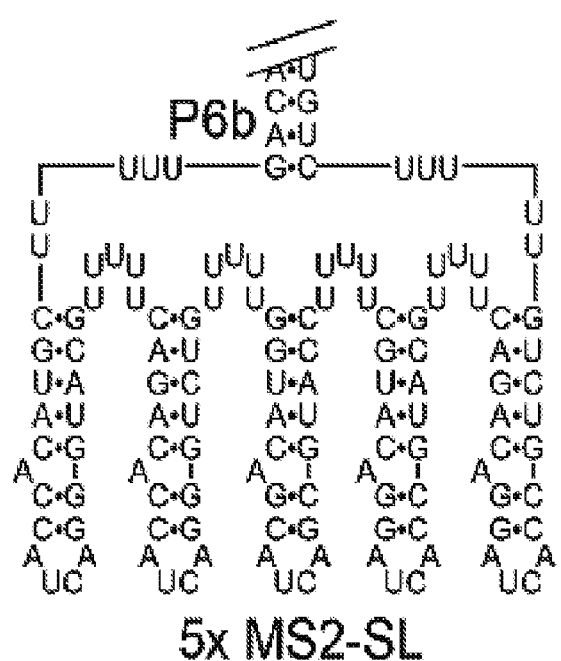

According to certain aspects, dCas9 was used to deploy a larger RNA cargo to a target DNA locus. Five topologies (TOP1-4; INT) in which the sgRNA was appended with structured, 81-250 nt "accessory domains" ("selected RNA sequences") that serve as proxies for larger RNAs in general were devised as shown in FIG. 2A and FIG. 7A, FIG. 7B. FIG. 7C, and FIG. 7D. Each domain furthermore contained a cassette of high-affinity cognate stem-loops for the PP7 phage coat protein (see Chao, J. A., Patskovsky, Y., Almo, S. C. & Singer, R. H. Structural basis for the coevolution of a viral RNA-protein complex. *Nature structural & molecular biology* 15, 103-105 (2008) hereby incorporated by reference in its entirety). In TOP1 and TOP2, the sgRNA was placed at the 5'- and 3'-end of the accessory domain, respectively as shown in FIG. 2A. In TOP3 and TOP4, the tracrRNA component of a natural crRNA•tracrRNA complex was likewise appended, respectively as shown in FIG. 2A. In the internal embodiment INT shown in FIG. 2A, an accessory domain was grafted into the internal sgRNA engineered loop which makes no direct contacts with the dCas9 protein (see Jinek, M. et al. Structures of Cas9 endonucleases reveal RNA-mediated conformational activation. *Science* 343, 1247997 (2014) hereby incorporated by reference in its entirety). At 357 nt, the largest of these constructs is more than three times the length of a minimal sgRNA and adds nearly five-fold more sequence than does the modified sgRNA previously reported (see Mali, P. et al. CAS9 transcriptional activators for target specificity screening and paired nickases for cooperative genome engineering. *Nature biotechnology* 31, 833-838 (2013) hereby incorporated by reference in its entirety).

With reference to FIG. 1C and FIG. 2D, the sgRNA chimeras were subjected to two variations of the CRISPR transcription activator assay. In "direct activation" assays, the sgRNA chimeras were coexpressed with dCas9~VP. Reporter gene activation indicates that the sgRNA variant forms a competent targeting complex with dCas9. In "bridged activation" assays, constructs were coexpressed with dCas9 and PP7~VP, a chimera of PP7 and VP64. Bridged activation should only occur if the accessory domain remains functional in the mature dCas9 complex.

The results of these assays are summarized in FIG. 2C. Using transient reporters (FIG. 2C, top), measurable direct activation was observed with all five topologies. However, while the activities of TOP1, TOP2 and INT rivaled that of the minimal sgRNA, TOP3 and TOP4 were less robust, exhibiting 2.7-10.8% of the efficacies of their unimolecular counterparts. Bridged activation was only observed with TOP1, TOP3 and INT, indicating that these constructs alone retained functional accessory domains in mature dCas9 complexes. FACS analysis data shown in FIG. 2D corroborated these results: for TOP1 and INT the populations of mCerulean+ cells appeared nearly equivalent under direct and bridged conditions. Results using integrated reporters (FIG. 2C, bottom) were qualitatively similar, although the low activities of TOP3 and TOP4 could not be significantly measured.

Without being bound by scientific theory, the inability of TOP2 to induce bridged activation may be due to degradation of its accessory domain, as has been observed with shorter sgRNA 5'-extensions (see Ran, F. A. et al. Double nicking by RNA-guided CRISPR Cas9 for enhanced genome editing specificity. *Cell* 154, 1380-1389 (2013) hereby incorporated by reference in its entirety). This hypothesis was supported by RNA immunoprecipitation (RIP) qRT-PCR: while recovery of the sgRNA core and accessory domains from dCas9•TOP1 complexes was quantitative, from dCas9•TOP2 complexes the yield of accessory domain was nearly half that of the sgRNA core as shown in FIG. 2E.

Together, these results demonstrate that dCas9 forms productive targeting complexes with relatively long guide RNAs, and can present an RNA cargo ("selected RNA sequence") to a DNA locus in at least two different topologies: on the sgRNA 3' terminus (TOP1), or within the sgRNA engineered loop (INT).

Example XIII

Targeting Long RNAs to an Endogenous Locus

Figure 4A:
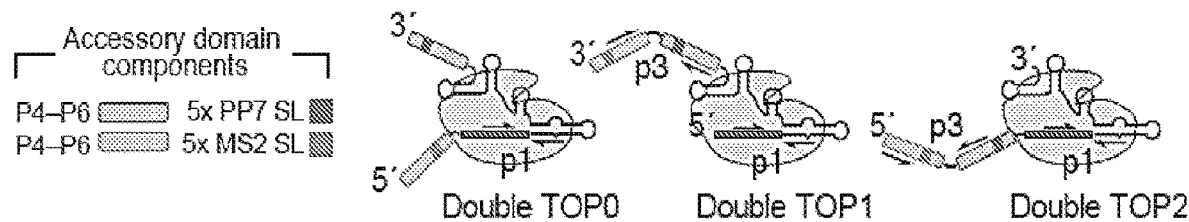
FIG. 4A-FIG. 4C are directed to CRISP/Cas complexes including guide RNA with artificial and natural lncRNAs.
Figure 4B:
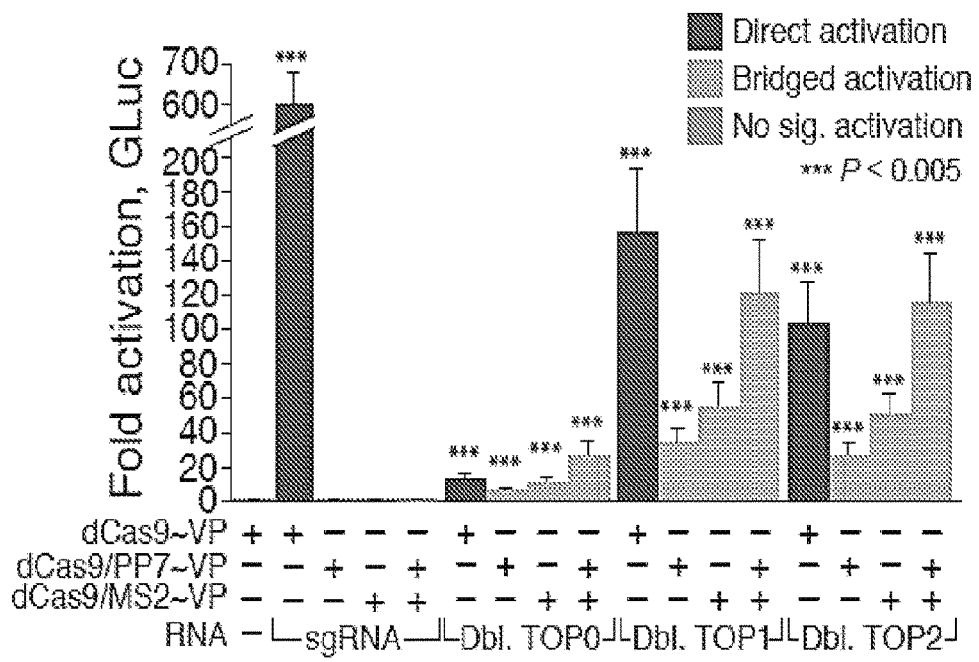
Figure 4C:
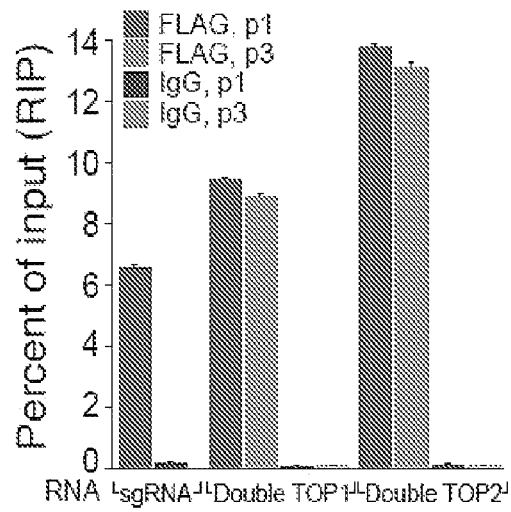
Figure 4D:
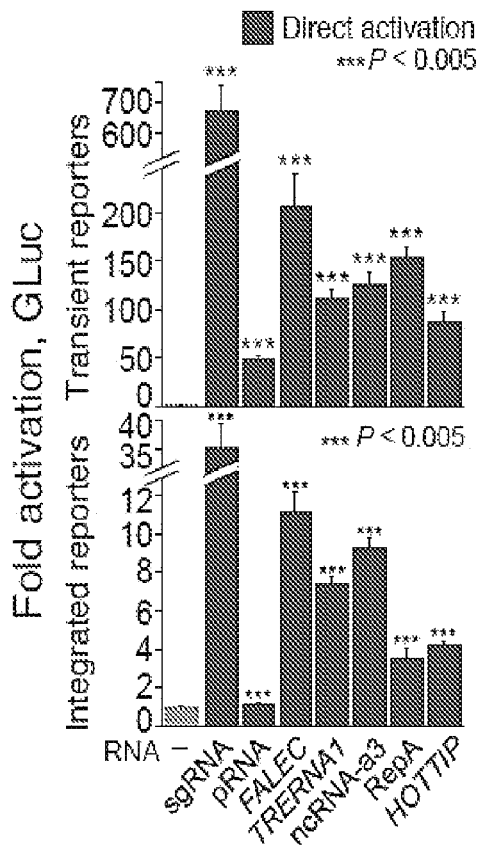
FIGS. 4D-4F are directed to a guide RNA with natural lncRNAs incorporated into the guide RNA or attached thereto.
Figure 4E:
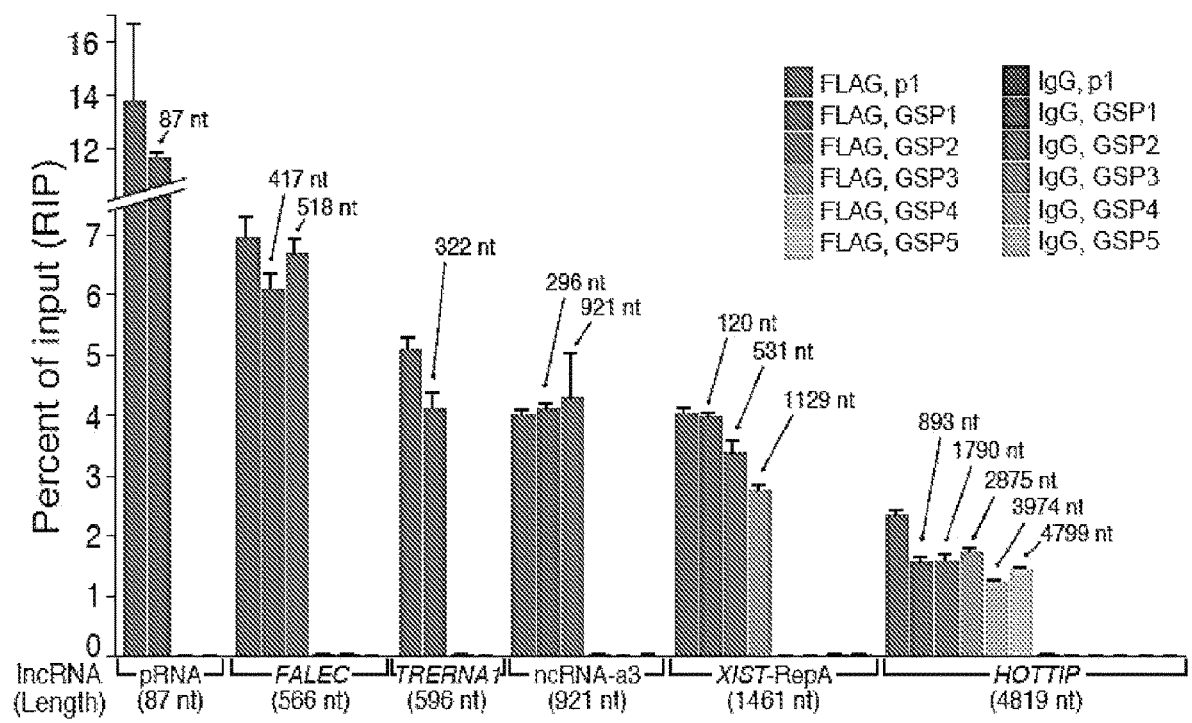
Figure 4F:
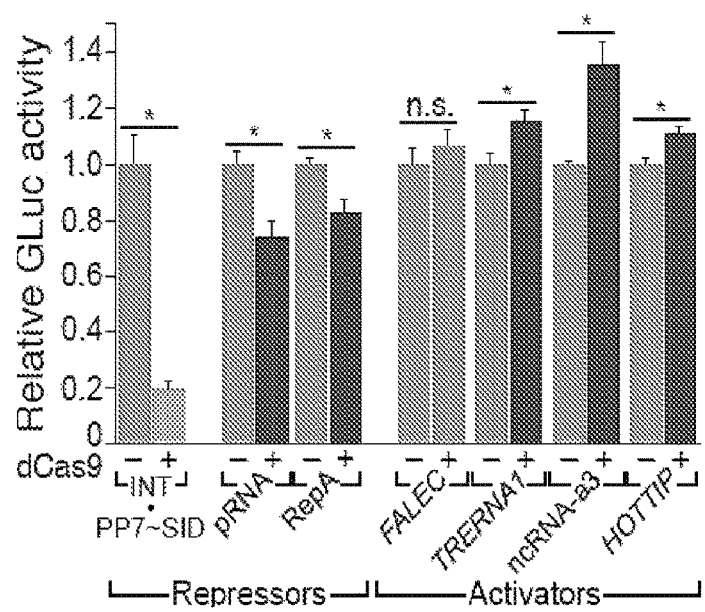
Figure 13A:
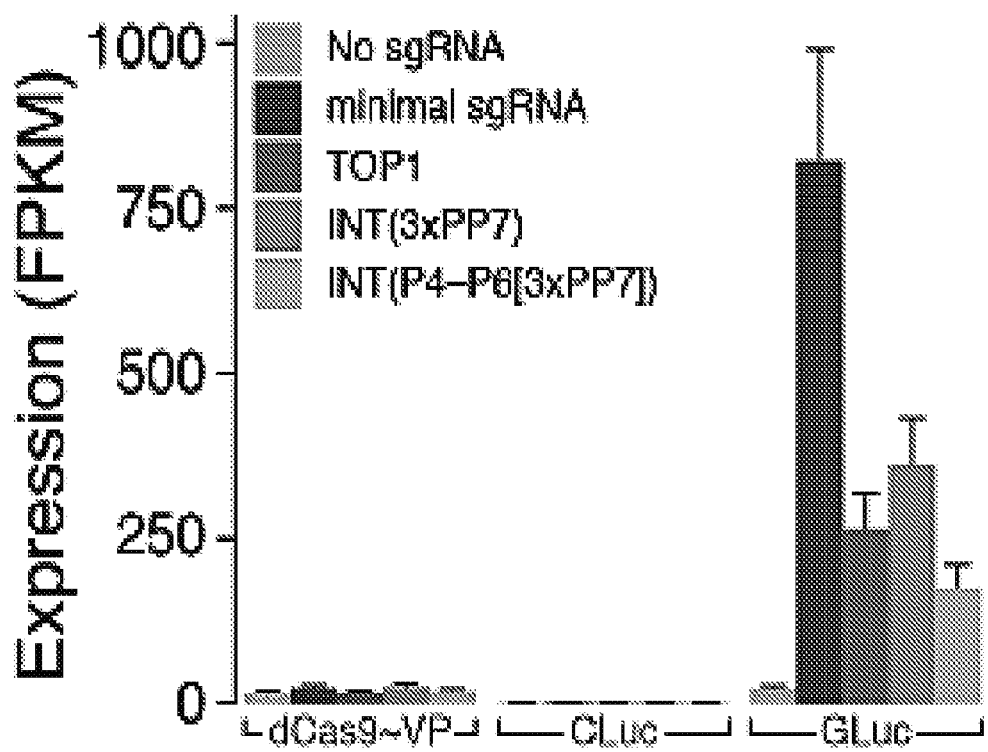
FIG. 13A-FIG. 13C are directed to data obtained from mRNA seq performed from reporter cells expressing dCas9~VP and GLuc-targeting sgRNA, TOP1 and INT(3× PP7), INT(S1) and INT(P4-P6[3×PP7]) constructs.
Figure 13B:
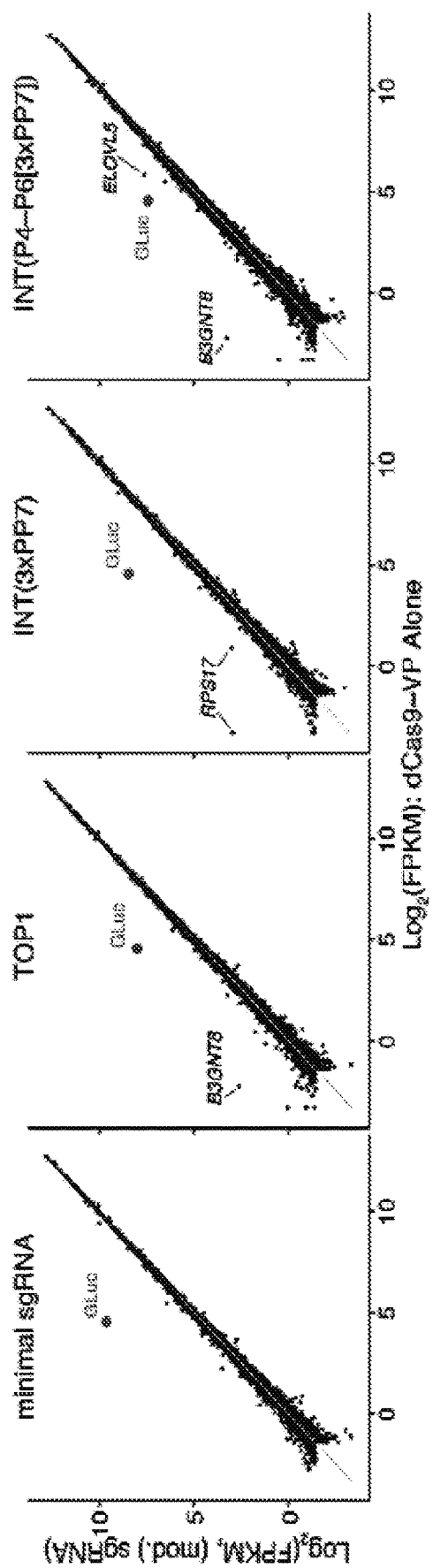
Figure 13C:
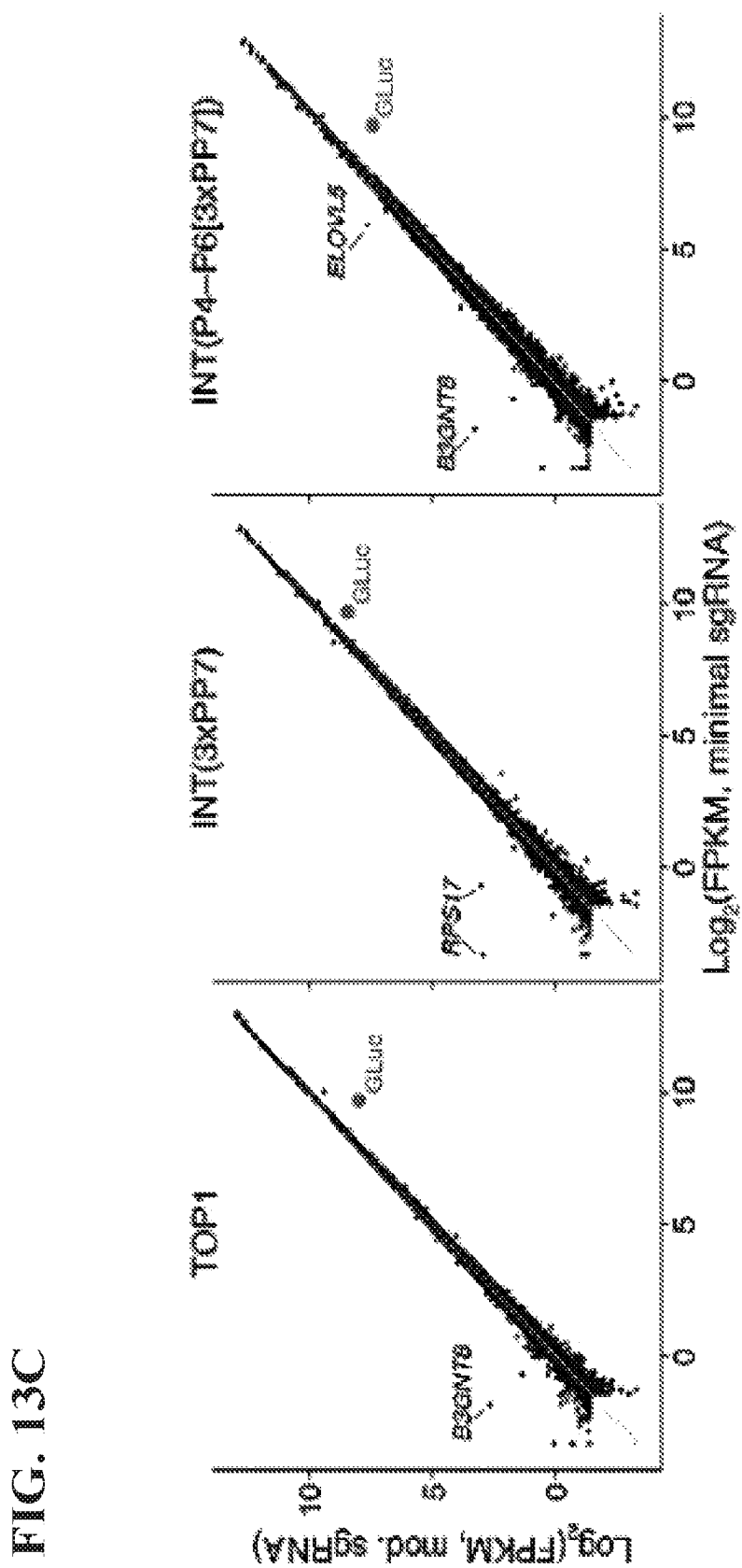

Pools of sgRNA, TOP1, INT(3×PP7), INT(S1) and INT (P4-P6[3×PP7]) constructs targeting the human ASCL1, IL1RN, NTF3 and TTN promoters were generated as shown in Table 2. Direct and bridged ASCL1, IL1RN, NTF3 and TTN activation was surveyed using qRT-PCR. These assays were performed in integrated GLuc reporter cells so as to simultaneously monitor construct efficacy and target specificity. As shown in FIGS. 2F and 4F, activation of the all endogenous loci by large CRISP-Disp complexes paralleled the results obtained using the GLuc reporter. Moreover, activation of each locus was specific to the gRNA sequences used. CRISP-Disp using TOP1- and INT-like constructs may be generally functional at endogenous loci. To examine this in broader scope, mRNA seq was performed from reporter cells expressing dCas9~VP and GLuc-targeting sgRNA, TOP1 and INT(3×PP7), INT(S1) and INT(P4-P6[3×PP7]) constructs (see FIG. 13A-FIG. 13C). All three RNA constructs induced measurable and specific activation of the GLuc reporter locus (see FIG. 13A-FIG. 13B). However, changes in global gene expression induced by each RNA construct—a proxy for dCas9 off-targeting—were essentially indistinguishable (see FIG. 13C). Collectively these results establish that CRISP-Disp with TOP1- and INT-like constructs should be generally functional at endogenous loci, and that addition of accessory RNA domains ("selected RNA sequences") to the sgRNA scaffold did not significantly alter dCas9 fidelity.

Example XIV

CRISP-Disp with RNA Polymerase II Transcripts

To evaluate CRISPR/Cas9 activity, a guide RNA including long ncRNAs, an RNA Polymerase III (Pol III) expression system (U6, FIG. 1C, bottom), which is limited in transcript length and sequence composition, was adapted with a Pol II promoter and terminator (see Nissim, L., Perli, S. D., Fridkin, A., Perez-Pinera, P. & Lu, T. K. Multiplexed and Programmable Regulation of Gene Networks with an Integrated RNA and CRISPR/Cas Toolkit in Human Cells. *Molecular cell* 54, 698-710 (2014) and Gao, Y. & Zhao, Y. Self-processing of ribozyme-flanked RNAs into guide RNAs in vitro and in vivo for CRISPR-mediated genome editing. *Journal of integrative plant biology* 56, 343-349 (2014) each of which are hereby incorporated by reference in its entirety). Several Pol II expression systems (see FIG. 3A) were surveyed for the ability to generate nuclear-localized CRISP-Disp RNAs de novo. Two systems ("EF1α/SV40 pA" and "CMV/SV40 pA") paired conventional mammalian promoters with a canonical polyadenylation signal. A third system ("CMV/3'Box") exploited the U1 snRNA 3'-Box, a modular element that directs transcription termination without polyadenylation (see Cuello, P., Boyd, D. C., Dye, M. J., Proudfoot, N. J. & Murphy, S. Transcription of the human U2 snRNA genes continues beyond the 3' box in vivo. *The EMBO journal* 18, 2867-2877 (1999) hereby incorporated by reference in its entirety). CMV/3'Box transcripts are not processed via a canonical snRNA pathway (see de Vegvar, H. E., Lund, E. & Dahlberg, J. E. 3' end formation of U1 snRNA precursors is coupled to transcription from snRNA promoters. *Cell* 47, 259-266 (1986) hereby incorporated by reference in its entirety), but have been shown to be nuclear-retained nonetheless. This effect is enhanced with longer transcripts (see Fuke, H. & Ohno, M. Role of poly (A) tail as an identity element for mRNA nuclear export. *Nucleic acids research* 36, 1037-1049 (2008) hereby incorporated by reference in its entirety). Two addition systems ("CMV/PAN" and "CMV/MASC") paired the CMV promoter with 3' triplex-forming "expression and nuclear retention elements" (ENEs), non-canonical RNA elements that protect nuclear-retained transcripts from degradation (see Wilusz, J. E. et al. A triple helix stabilizes the 3' ends of long noncoding RNAs that lack poly(A) tails. *Genes & development* 26, 2392-2407 (2012) hereby incorporated by reference in its entirety.) The PAN element is derived from the Kaposi's sarcoma-associated herpesvirus (KSHV) Polyadenylated Nuclear transcript (see PAN, Conrad, N. K., Mili, S., Marshall, E. L., Shu, M. D. & Steitz, J. A. Identification of a rapid mammalian deadenylation-dependent decay pathway and its inhibition by a viral RNA element. *Molecular cell* 24, 943-953 (2006) hereby incorporated by reference in its entirety). The MASC element is derived from the MALAT1 locus, and comprises the MALAT1 ENE, an encoded poly(A) tail and a tRNA-like domain (MALAT1-associated small cytoplasmic RNA, mascRNA), that is removed by RNase P. A final system (U1/sm/3'Box) was designed with the goal of mimicking the biogenesis of small nuclear RNAs (snRNPs), which transcribed in the nucleus, exported into the cytoplasm for assembly, and thereafter reimported into the nucleus (see Battle, D. J. et al. The SMN complex: an assembly machine for RNPs. *Cold Spring Harbor symposia on quantitative biology* 71, 313-320 (2006) hereby incorporated by reference in its entirety.) This system paired the U1 snRNA promoter (U1 Pro), the U2 snRNA "sm domain" which is required for nuclear import, and the U1 3'Box, as described above.

Figure 3B:
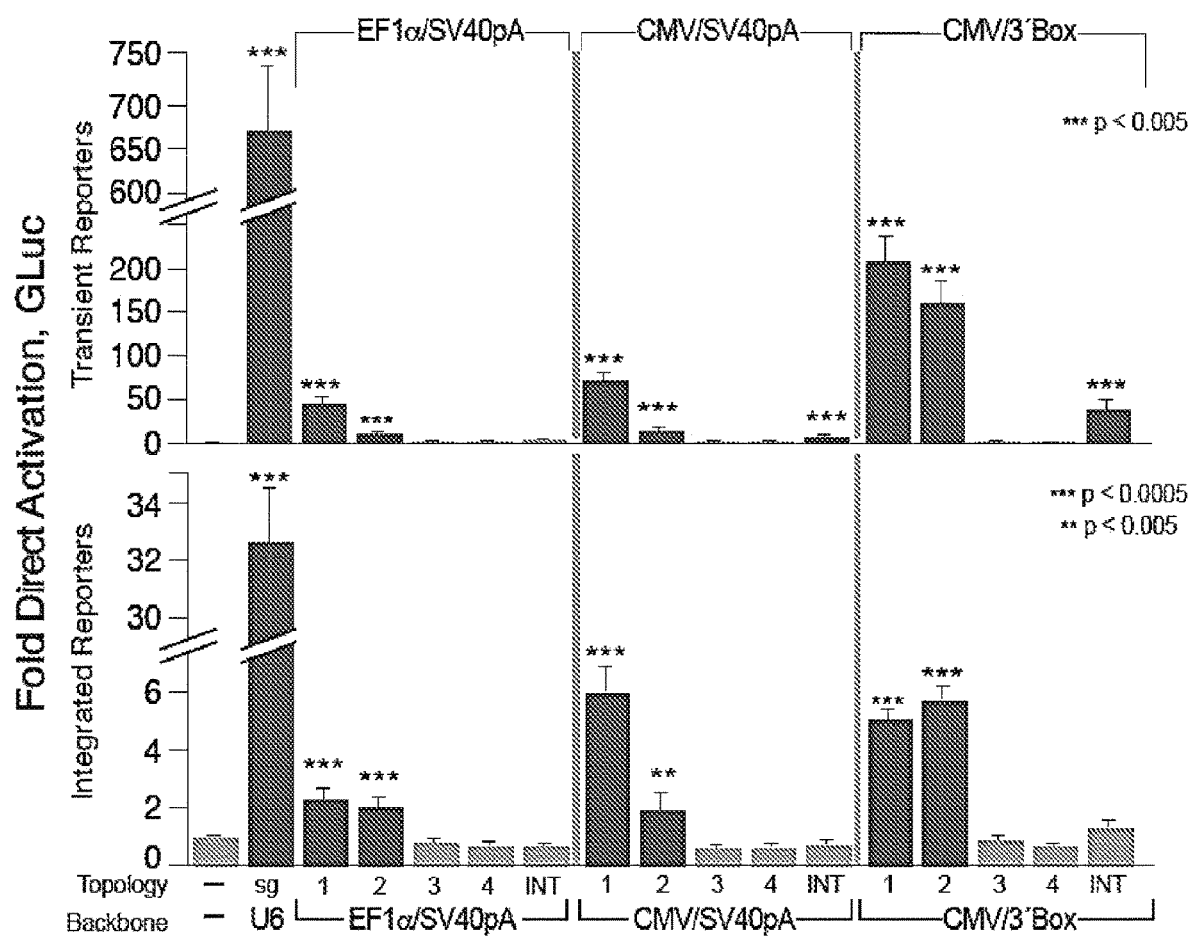
Figure 14A:
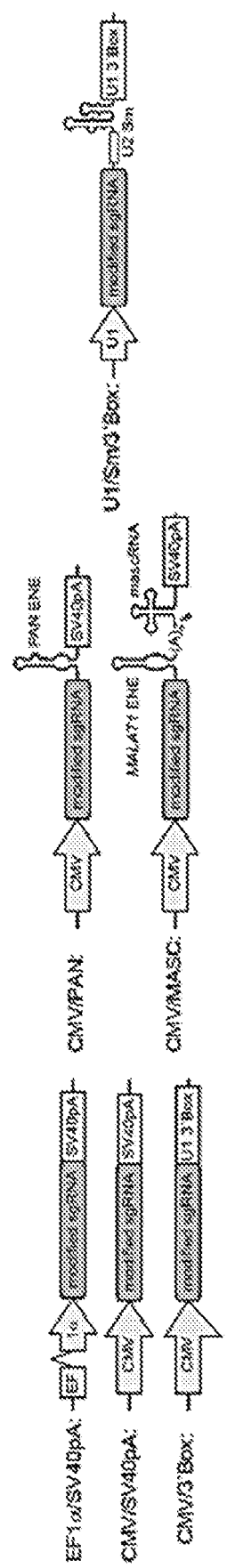
FIG. 14A depicts exemplary embodiment of various constructs.
Figure 14B:
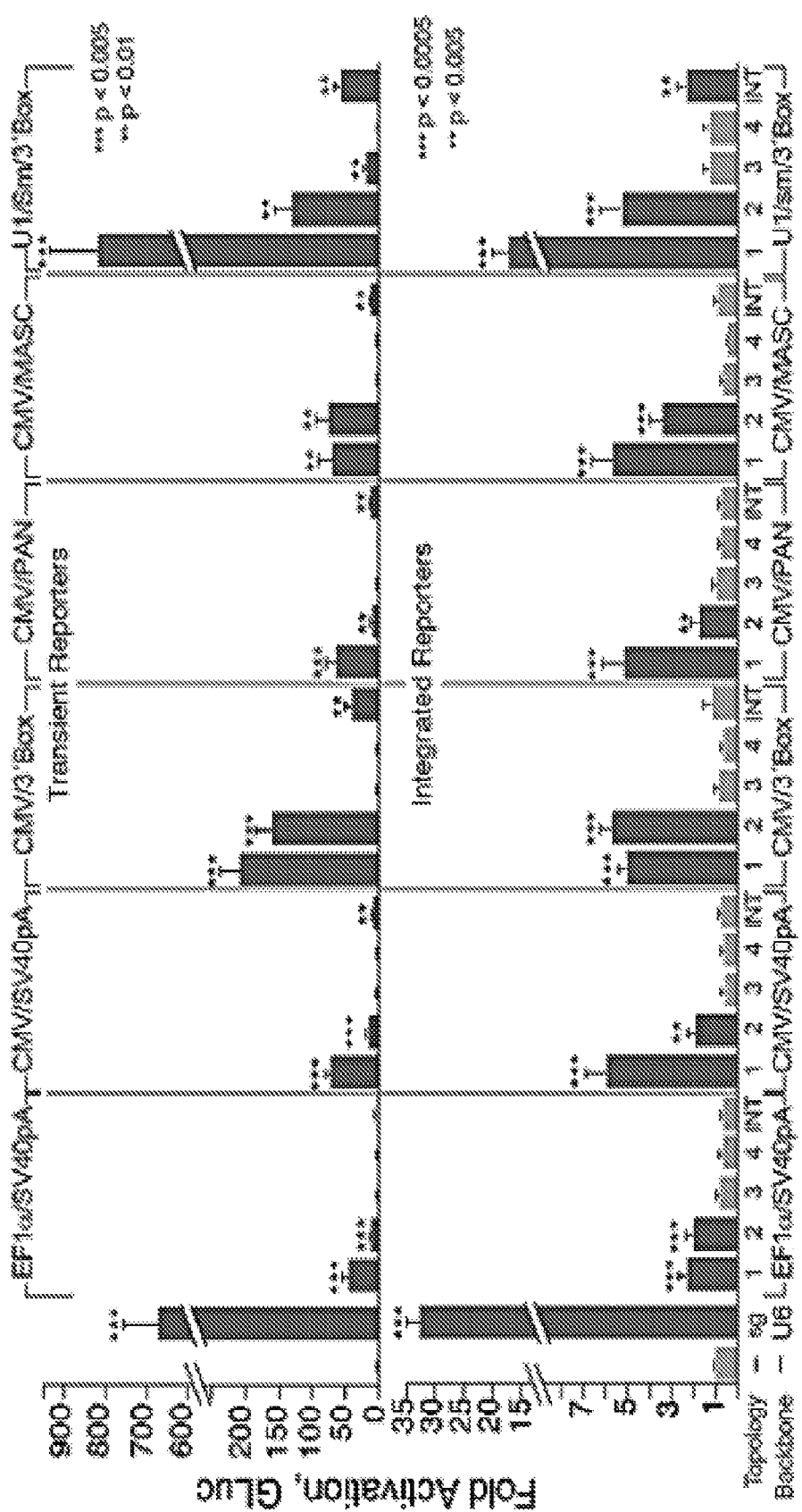
FIG. 14B depicts data from direct activation assays on transient reporters.

Five chimeric sgRNA constructs shown in FIG. 2A, expressed from each Pol II backbone, were subjected to direct activation assays on transient reporters, data for which is shown in FIG. 3B, top and FIG. 14B). In general, Pol II transcripts were markedly less effective and topologically more limited than their Pol III-expressed counterparts, with EF1α/SV40 pA and CMV/SV40 pA being the least effective. In contrast, CMV/3'Box transcripts were more proficient: TOP1 was restored to ~35% of its U6-driven counterpart's activity, while TOP2 was restored to nearly 30%. These results were largely paralleled in integrated reporter assays (FIG. 3B, bottom). This rise in activity correlated with a lack of transcript polyadenylation and a concomitant increase in nuclear transcript abundance, data for which is shown in FIG. 8A, FIG. 8B, FIG. 8C and FIG. 8D.

Figure 3C:
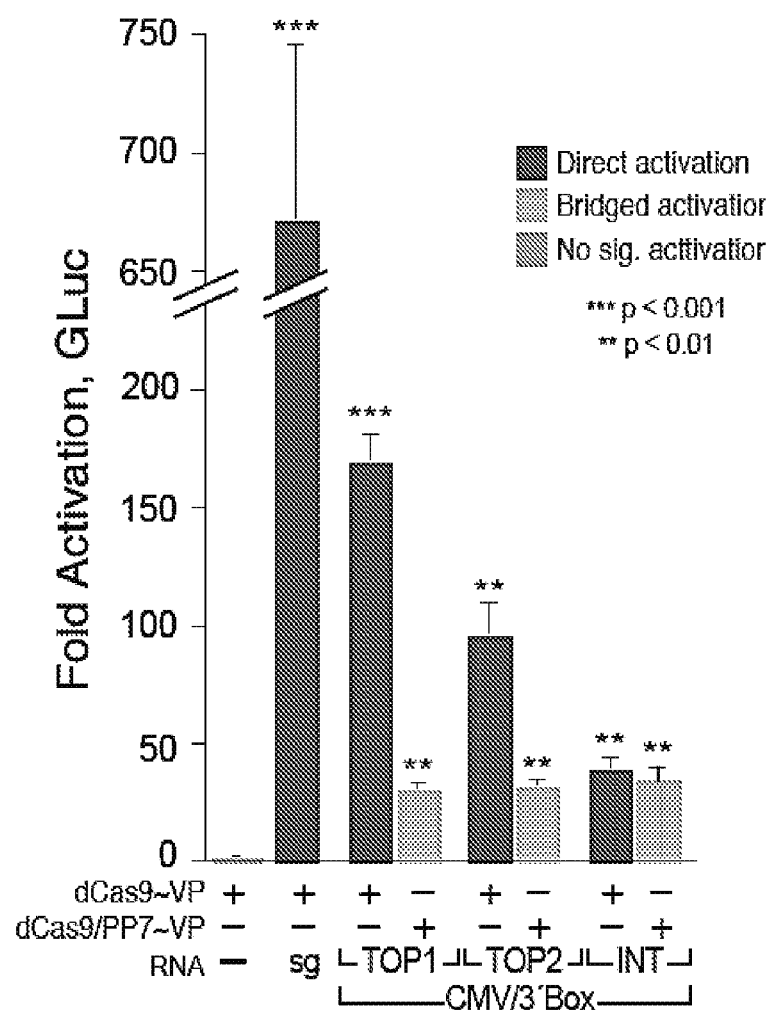
Figure 3D:
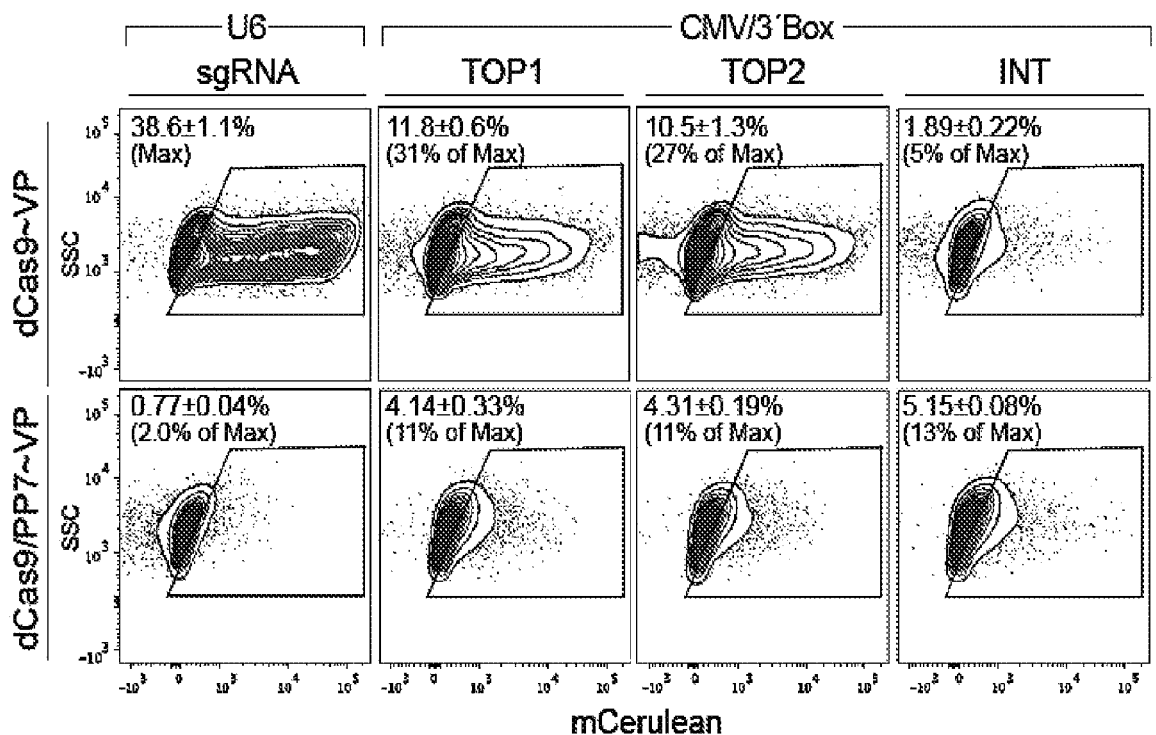
Figure 3E:
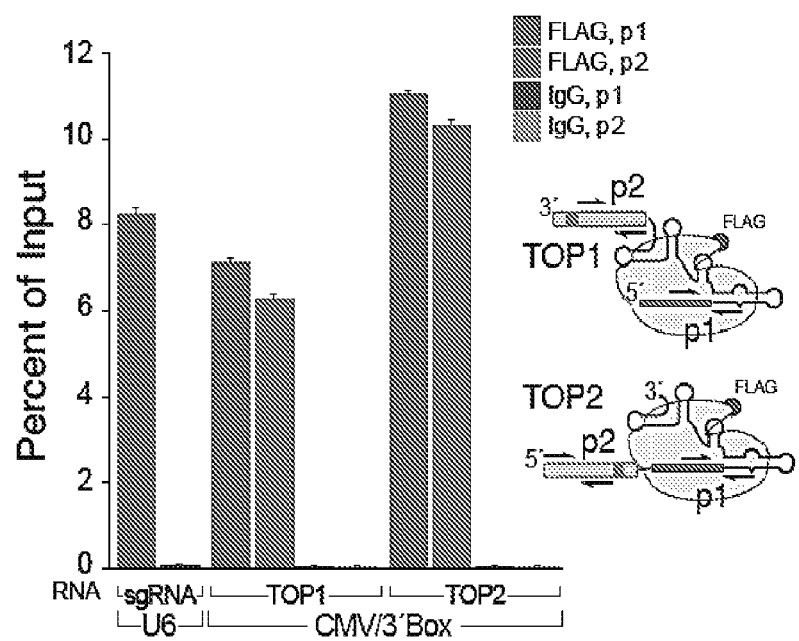
Figure 14C:
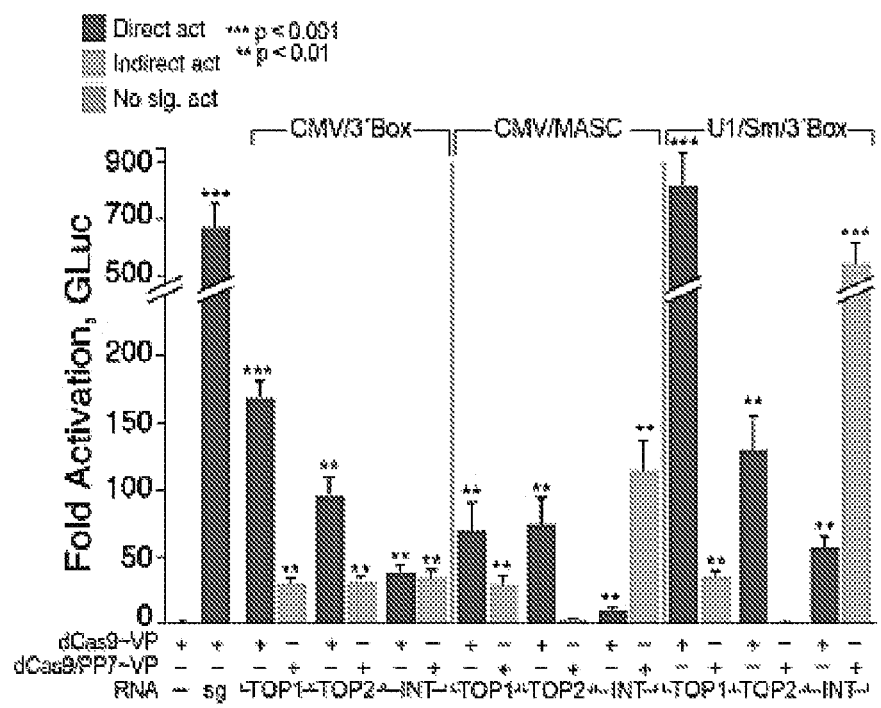
FIG. 14C depicts data from bridged activation assays of CMV/3'Box constructs.
Figure 14D:
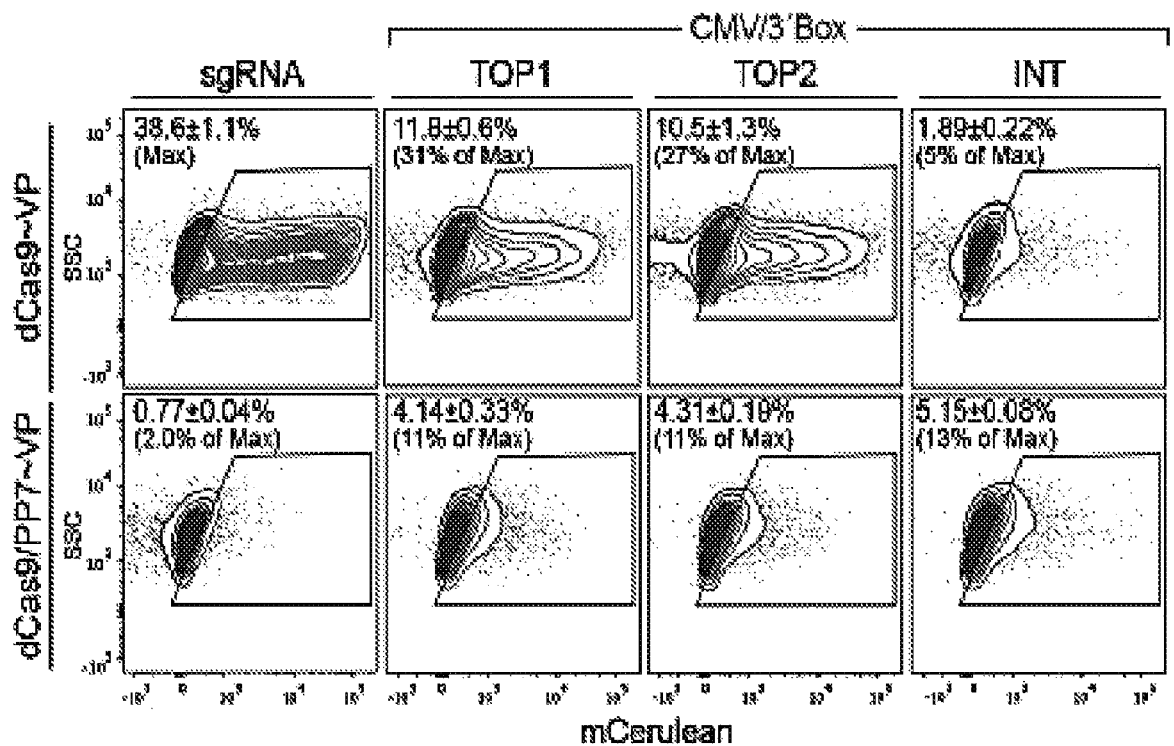
FIG. 14 D depicts data from bridged activation assays of CMV/3'Box constructs.

The three most proficient CMV/3'Box constructs were tested using bridged activation assays. As observed with U6-driven RNAs, both TOP1 and INT exhibited robust bridged activation—to ~20% and ~75% of the corresponding direct activation levels—indicating that each retained an intact accessory domain in its mature CRISP-Disp complex, data for which is shown in FIG. 3C and FIG. 14C-14D. CMV/3'Box TOP2 also exhibited bridged activation at a comparable level, in contrast with its U6-driven counterpart. FACS analysis corroborated these results, as shown in FIG. 3D. Furthermore, immunoprecipitation of dCas9•TOP2 isolated the sgRNA core and accessory domains in nearly stoichiometry yields, indicating that the TOP2 chimera remained intact in complex with dCas9, data for which is shown in FIG. 3E.

These results demonstrate a method for assembling CRISP-Disp complexes with Pol II-expressed RNAs, a necessary reagent for the display of lncRNAs. Moreover, this method permits the expansion of the sgRNA scaffold in a third topology: the 5'-terminus (TOP2).

Example XV

CRISP/Cas Systems with Artificial Long Noncoding RNAs

To examine the length limitations on an RNA attached to a guide RNA, dCas9 complexes were prepared with transcripts approaching the size of natural long noncoding RNAs ("lncRNAs"). CMV/3'-Box TOP1 and TOP2 constructs were expanded by adding a second complete P4-P6 domain bearing a cassette of MS2 stem-loops as shown in FIG. 4A left, and FIG. 7A, FIG. 7B, FIG. 7C and FIG. 7D. The two P4-P6 domains in these "artificial lncRNA" constructs were positioned so as to bracket the sgRNA core ("Double TOP0,"), or contiguously on the sgRNA 3'- and 5'-terminus ("Double TOP1" and "Double TOP2," respectively). At 650 nucleotides ("nt"), these accessory domains are themselves nearly seven times longer than a minimal sgRNA.

All three constructs induced measurable direct activation of both transient and integrated GLuc reporters, data for which is shown in FIG. 4A, right). Of these, Double TOP1-2 were more proficient, in transient assays exhibiting ~23% and ~15%, respectively, of the activity of the minimal sgRNA, and nearly rivaling the activity of their single-domain counterparts. Moreover, all three constructs exhibited significant bridged activation. In transient reporter assays, luciferase activity monotonically increased upon coexpression with PP7~VP, MS2~VP or both, indicating that each construct retained both P4-P6 domains in mature dCas9 complexes, data for which is shown in FIG. 4B. For Double TOP1-2 this was corroborated by RIP qRT-PCR, using a primer pair that spans the two P4-P6 domains: immunoprecipitated yields of the sgRNA and double P4-P6 domains were essentially quantitative, data for which is shown in FIG. 4C.

The construction of functional CRISP-Disp complexes is not limited by RNA length. Furthermore, constructs like Double TOP0-2, which specifically bind two different cognate proteins, are useful in the design of chromatin-targeting lncRNA-like "scaffolds." (See Delebecque, C. J., Lindner, A. B., Silver, P. A. & Aldaye, F. A. Organization of intracellular reactions with rationally designed RNA assemblies. *Science* 333, 470-474 (2011) hereby incorporated by reference in its entirety.)

Example XVI

CRISP/Cas Systems with Natural Long Noncoding RNAs

To investigate if CRISPR-Display would be compatible with natural long noncoding RNAs, Pol II-driven TOP1- and INT-like constructs appended with human lncRNA domains, spanning lengths of 87-4799 nt were generated (see Table 4). These domains included the repressive NoRC-binding pRNA stem-loop (Mayer, C., Neubert, M. & Grummt, I. The structure of NoRC-associated RNA is crucial for targeting the chromatin remodelling complex NoRC to the nucleolus. *EMBO reports* 9, 774-780 (2008) hereby incorporated by reference in its entirety), three enhancer-transcribed (eRNAs, Orom, U. A. et al. Long noncoding RNAs with enhancer-like function in human cells. *Cell* 143, 46-58 (2010) hereby incorporated by reference in its entirety), the repressive A-repeat domain ("RepA") of Xist (Minks, J., Baldry, S. E., Yang, C., Cotton, A. M. & Brown, C. J. XIST-induced silencing of flanking genes is achieved by additive action of repeat a monomers in human somatic cells. *Epigenetics & chromatin* 6, 23 (2013) hereby incorporated by reference in its entirety) and putative transcription activator HOTTIP (Wang, K. C. et al. A long noncoding RNA maintains active chromatin to coordinate homeotic gene expression. *Nature* 472, 120-124 (2011) hereby incorporated by reference in its entirety). As demonstrated by RIP-qPCR (targeting the sgRNA core, (see Table 3), each construct was efficiently incorporated into dCas9 complexes, although this efficiency declined monotonically with increasing lncRNA length (see FIG. 4D). Furthermore, by surveying various intervals spanning the lncRNA domain (see Table 3), it was observed that, relative to the sgRNA core, nearly stoichiometric yields of intact lncRNA domains were recovered for all constructs, indicating that each remained intact in the majority of CRISP-Disp complexes (see FIG. 4D). CRISPR methods described herein can accommodate ncRNA domains of up to several kilobases in length, including naturally-occurring lncRNAs, attached to, appended to, or included within guide RNA.

Having established that lncRNAs can be incorporated into gRNA for use with a CRISP system, it was next examined if these complexes could regulate a reporter. Most of the lncRNA constructs repressed or activated GLuc expression as predicted, albeit quite modestly: pRNA and RepA diminished normalized GLuc expression, while TRERNA1, ncRNA-a3 and HOTTIP induced moderate activation (see FIG. 4E).

Example XVII

CRISP-Disp with a Diverse Array of RNA Species

The sgRNA "engineered loop" was tested as an insertion point for exogenous RNA domains of different sequences and structures. To examine the influence of internal insert size on guide RNA for use with a CRISPR system (CRISPR-Disp), a series of INT-like constructs bearing one, three or five internal PP7 stem-loops, spanning 25-137 nt was generated (see FIG. 5A and Table 5). Each construct induced robust Gluc activation in all assay formats, data for which is shown in FIG. 5A, indicating that each formed a productive CRISP-Disp complex with an intact accessory domain. Notably, this fivefold expansion of insert size reduced activity only twofold, implying that yet larger internal insertions may be tolerated. A ~250 nt domain ("selected RNA sequence"), equivalent to the accessory domains of TOP1-4, was appended via a flexible three-way junction at the internal insertion point (See FIG. 5B and Table 5). This construct also induced robust GLuc activation in all assay formats, indicating that even an insert 2.5-fold larger than—and structurally discontinuous with—the core sgRNA can be easily accommodated. Larger and more structurally diverse selected RNA sequence species could be grafted internally.

A pool of $\sim 1.2 \times 10^6$ unique sgRNA variants displaying internal cassettes of 25 random nucleotides ("selected RNA sequence") were synthesized to determine whether a potentially vast portion of sequence space could be displayed (see FIG. 5C, FIG. 9A and FIG. 9B). In aggregate, this INT-$N_{25}$Pool activated GLuc expression at or beyond the level induced by the minimal sgRNA, data for which is shown in FIG. 5C, indicating that many of the variants formed productive CRISPR/Cas complexes. To confirm this, dCas9•INT-$N_{25}$Pool complexes were immunoprecipitated and the copurified sgRNA sequences were analyzed by deep sequencing (RIP-Seq), data for which is shown in FIG. 5D, FIG. 10A, FIG. 10B and FIG. 10C. Fewer than 0.01% and 0.02% of the observed 1.2 million sequence variants were significantly enriched or de-enriched, respectively; motif analysis of these variants revealed no clear sequence constraints influencing sgRNA•dCas9 complexation. Although a pool of this diversity represents a small ($\sim 1.1 \times 10^{-9}$), biased sampling of the total 25-nucleotide sequence space, functionality of guide RNA in a CRISPR complex is not intrinsically limited by the sequence of an internal insert.

Figure 5E:
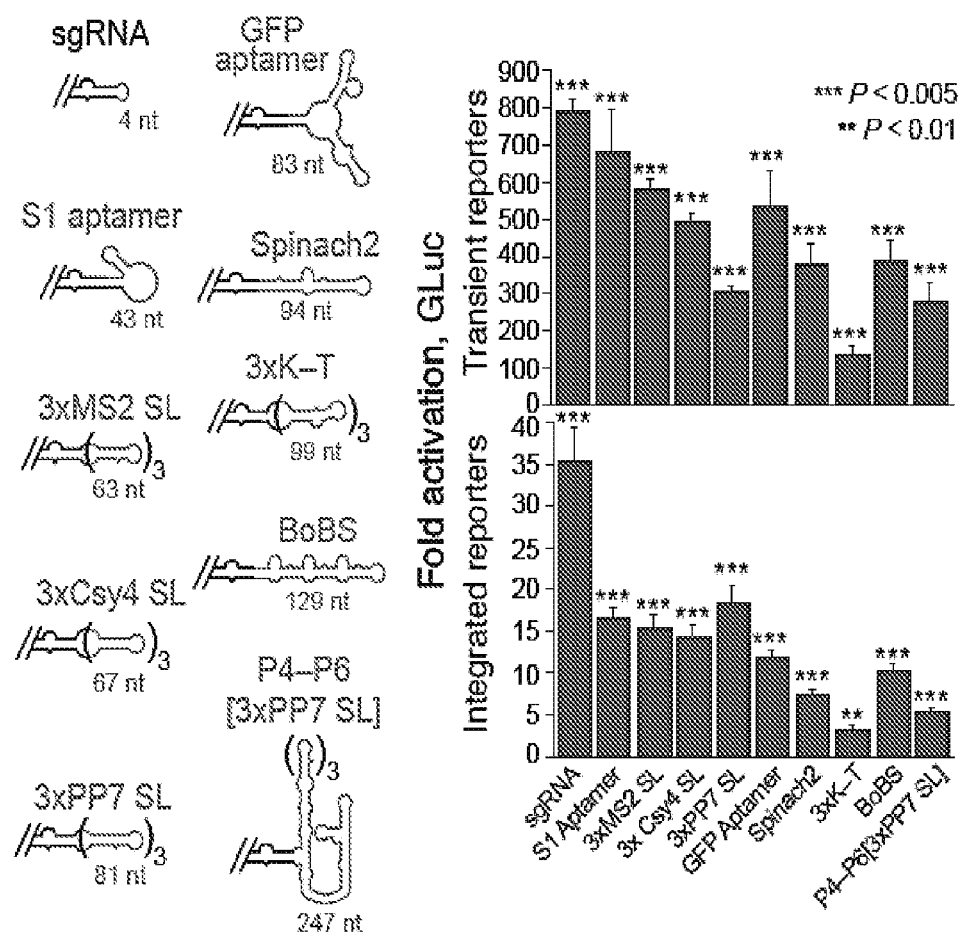
Figure 5F:
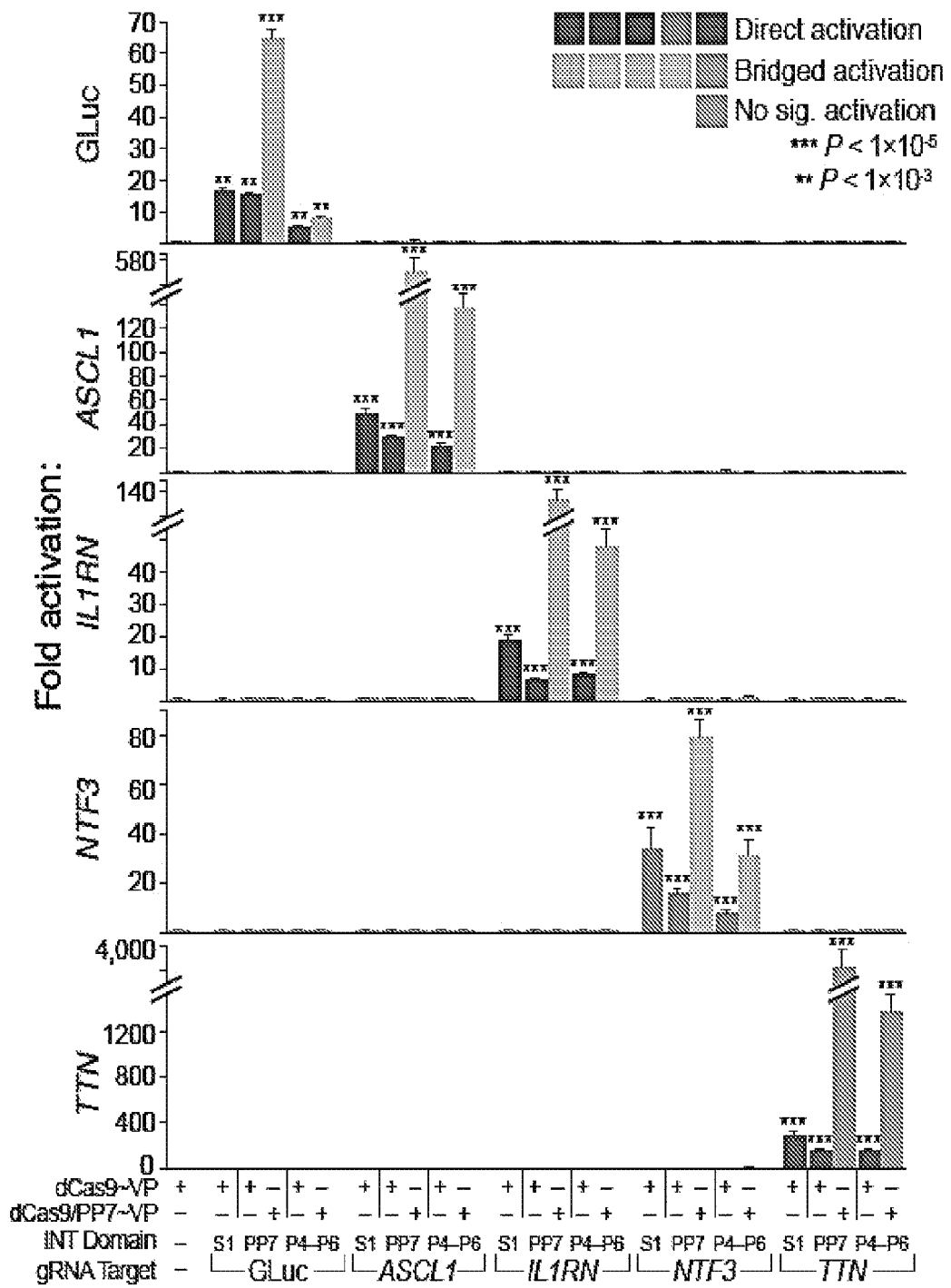
FIG. 5F depicts targeting INT-like constructs bearing RNA devices or large domains to endogenous loci. The INT-S1 aptamer ("S1") and INT-P4-P6[3×PP7] ("P4-P6") constructs were targeted to ASCL1, IL1RN, NTF3 and TTN. Data were generated and analyzed and data is shown in FIG. 2F; those from the original INT-3×PP7 SL construct ("PP7") are included for comparison.

A series of INT-like constructs displaying an array of functional RNA domains were generated as shown in FIG. 5E, left and Table 5). This compendium included motifs recognized by natural RNA-binding proteins (see Delebecque, C. J., Lindner, A. B., Silver, P. A. & Aldaye, F. A. Organization of intracellular reactions with rationally designed RNA assemblies. Science 333, 470-474 (2011); Saito, H. et al. Synthetic translational regulation by an L7Ae-kink-turn RNP switch. Nature chemical biology 6, 71-78 (2010); and Sternberg, S. H., Haurwitz, R. E. & Doudna, J. A. Mechanism of substrate selection by a highly specific CRISPR endoribonuclease. Rna 18, 661-672 (2012) each of which are hereby incorporated by reference in its entirety, and artificial aptamers that bind proteins (see Walker, S. C., Good, P. D., Gipson, T. A. & Engelke, D. R. The dual use of RNA aptamer sequences for affinity purification and localization studies of RNAs and RNA-protein complexes. Methods in molecular biology 714, 423-444 (2011); and Tome, J. M. et al. Comprehensive analysis of RNA-protein interactions by high-throughput sequencing-RNA affinity profiling. Nature methods 11, 683-688 (2014) each of which are hereby incorporated by reference in its entirety) and small molecules (see Song, W., Strack, R. L., Svensen, N. & Jaffrey, S. R. Plug-and-play fluorophores extend the spectral properties of Spinach. Journal of the American Chemical Society 136, 1198-1201 (2014) hereby incorporated by reference in its entirety). Although their activities spanned a tenfold range, all constructs exhibited significant direct activation as shown in FIG. 5E, right), indicating that all were viable in a CRISPR/Cas system.

Example XVIII

Concomitant Deployment of Multiple Functionalities

Aspects of the present disclosure are directed to the use of an orthogonal set of high-affinity RNA•protein pairs. Each protein would be appended with a different functional group, and targeted to distinct loci by sgRNAs that bear its cognate RNA motif. Orthogonal RNA-binding proteins were displayed on dCas9, as confirmed by bridged activation assays with the well-established A. fulgidus L7Ae ribosomal protein and bacteriophage coat proteins MS2 and PP7, each fused to VP64 (see Chao, J. A., Patskovsky, Y., Almo, S. C. & Singer, R. H. Structural basis for the coevolution of a viral RNA-protein complex. Nature structural & molecular biology 15, 103-105 (2008) and Saito, H. et al. Synthetic translational regulation by an L7Ae-kink-turn RNP switch. Nature chemical biology 6, 71-78 (2010) each of which are hereby incorporated by reference in its entirety). Bridged activation was only observed when cognate sgRNA•protein pairs were coexpressed. As shown in FIG. 6A, no activation was observed with non-cognate complexes or with a minimal sgRNA.

The modularity of guide RNA as described herein was demonstrated by simultaneously performing distinct functions at different loci. dCas9 was bound to multiple genomic targets but only one was selectively activated as shown in FIG. 6B. GLuc- and NTF3-targeting sgRNA variants bearing internal cassettes of PP7 and MS2 stem-loops were generated. Orthogonally modified pairs of each targeting construct (i.e., GLuc-PP7 with NTF3-M52, or vice versa) were co-expressed in integrated GLuc reporter cells. When also coexpressed with dCas9~VP, a robust activation of both target genes was observed, regardless of the sgRNA pair used (see FIG. 6B, left), indicating that dCas9 had bound both loci under all conditions. However, when each sgRNA pair was coexpressed with dCas9 and PP7~VP, only the gene targeted by sgRNAs bearing PP7 stem-loops was activated (see FIG. 6B, middle). The converse results were observed upon coexpression with dCas9 and MS2~VP (see FIG. 6B, right).

Collectively, these data demonstrate that guide RNA as described herein as part of a CRISPR/Cas system allow multiple manipulations to be performed simultaneously at discrete loci (see FIG. 6B, bottom).

It was investigate whether the methods described herein can simultaneously perform two unrelated functions—transcription activation and live-cell imaging of genomic loci (Chen, B. et al. Dynamic imaging of genomic loci in living human cells by an optimized CRISPR/Cas system. Cell 155, 1479-1491 (2013) hereby incorporated by reference in its entirety)—at different sites within the genome. A "bridged CRISPR-imaging" approach was developed in which the dCas9~eGFP fusion used in conventional CRISPR-imaging was replaced by a ternary complex comprising dCas9, an MS2~mCherry fusion, and an INT-like sgRNA construct bearing a cassette of MS2 stem-loops (FIG. 4e).

As an exemplary method, dCas9 was targeted to telomeres, as performed previously. When dCas9, MS2~mCherry and the modified sgRNA were coexpressed in HEK293FT cells, numerous (8-55; average of 26.6, in ~97 mCherry+ cells) fluorescent nuclear foci were observed. This signal was ablated by omission of dCas9, of the modified sgRNA, or by replacement of the MS2 stem-loop cassette with noncognate kink-turns.

Figure 15:
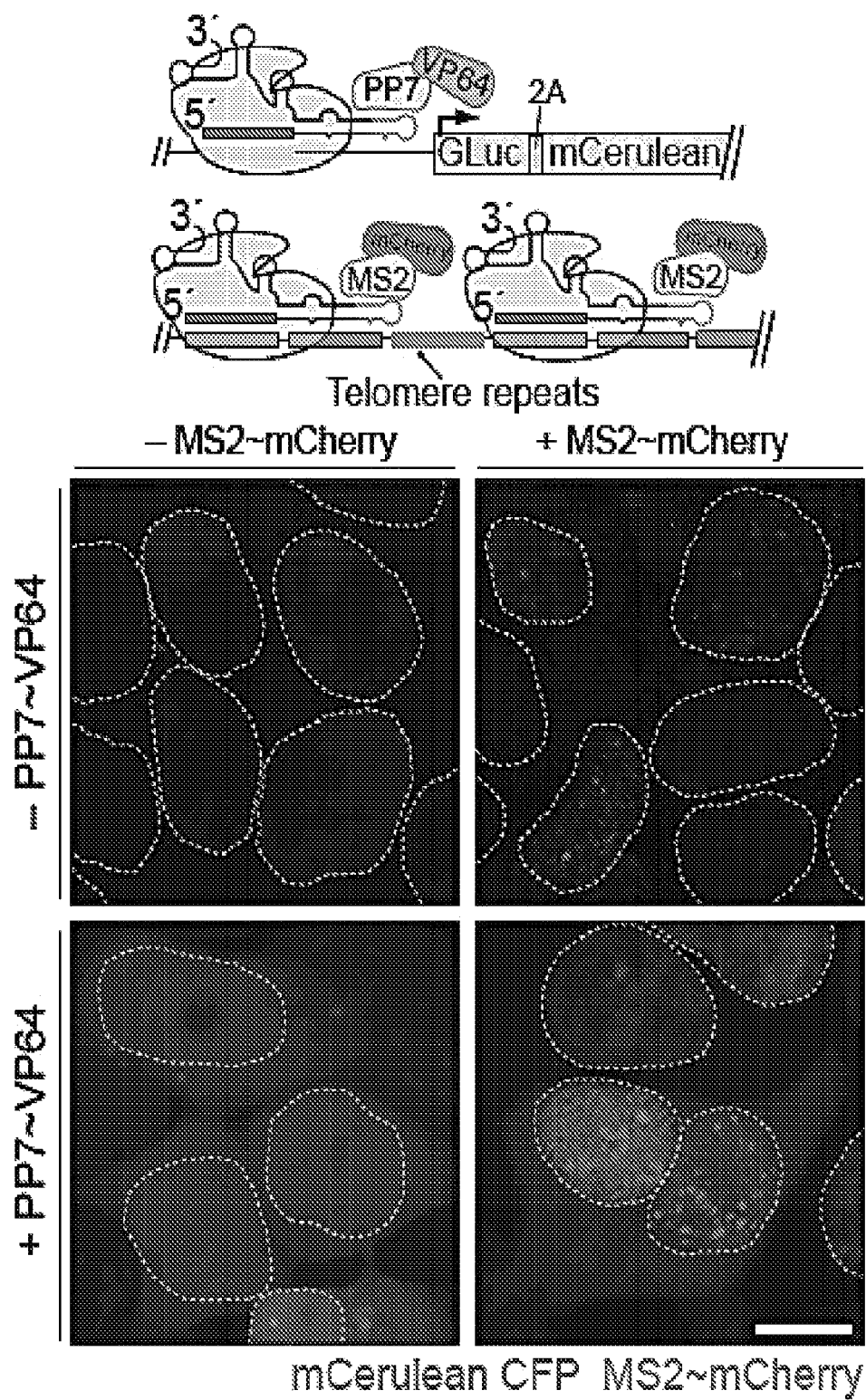
FIG. 15 depicts simultaneous activation and imaging of distinct loci in integrated GLuc reporter cells, using a shared pool of dCas9. Top: schematic of the experimental design. INT derivatives bearing cassettes of PP7 and MS2 stem-loops targeting GLuc and telomeres, respectively, were simultaneously coexpressed with dCas9, PP7~VP64 and MS2~mCherry. 2A: a 2A "self-cleaving" peptide. Middle and Bottom: Integrated GLuc reporter cells, activated and imaged using the indicated constructs. GLuc- and telomere-targeting INT derivatives were coexpressed in all experiments. Confocal fluorescence images, at 63× magnification. All cells transiently expressed dCas9 and each INT-like sgRNA derivative. Additional fusion proteins (PP7~VP64 and MS2~mCherry) were transiently expressed as indicated. Dotted lines denote nuclear membranes.
Figure 16A:
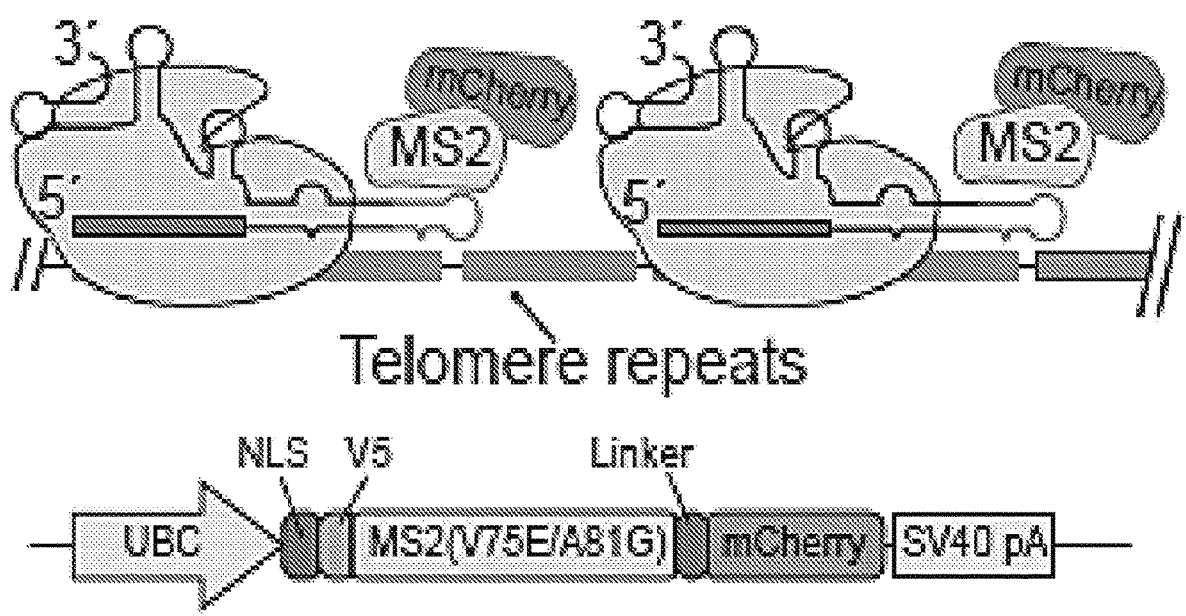
FIG. 16A depicts (Top) Experimental design. A telomere-targeting sgRNA internally appended with three MS2 stem-loops ("Telo-INT(3×MS2)") binds an MS2~mCherry fusion, and is localized to the telomeric repeats by dCas9. (Bottom) Schematic of the MS2~mCherry expression construct. UBC: the human Ubiquitin Chain C promoter; MS2 (V75E/A81G) is a non-aggregating variant; V5, a V5 epitope tag.
Figure 16B:
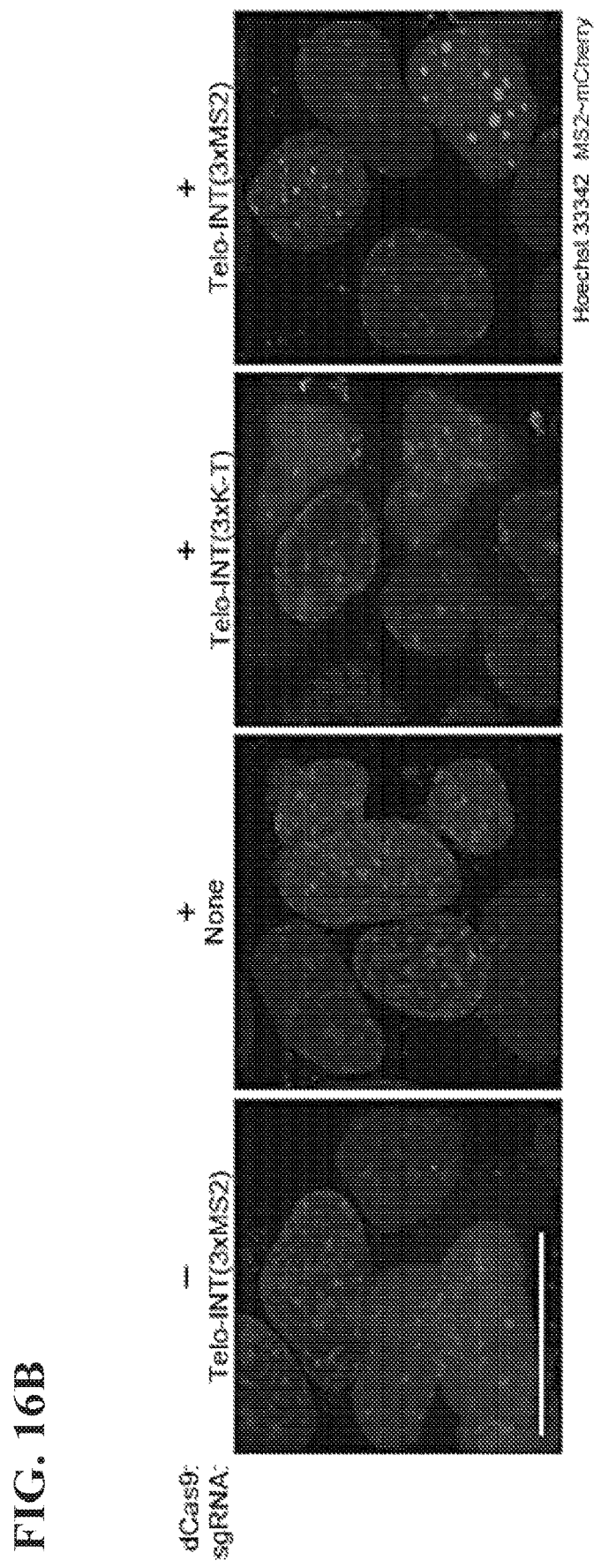
FIG. 16B depicts that bridged telomere imaging requires a cognate sgRNA and dCas9. All cells express MS2~mCherry, in addition to the indicated constructs. "Telo-INT(3×K-T)," a telomere-targeting INT-like sgRNA appended with a cassette of three kink-turns. Images are merged z-stacks at 63× magnification.
Figure 16C:
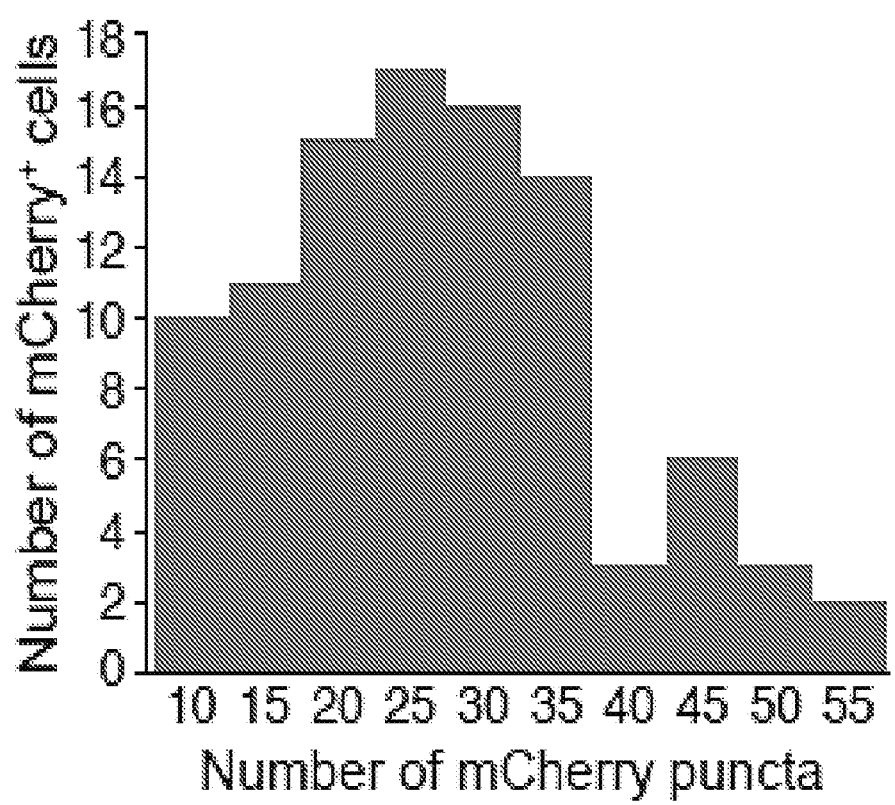
FIG. 16C depicts a histogram of observed fluorescent puncta in 97 mCherry+ cells. Scale bar, 15 um.

To simultaneously activate one locus and image another, integrated GLuc reporter cells were used for performing bridged activation (using PP7~VP64, targeted by INT) at the reporter locus, and bridged imaging (using MS2~mCherry, as above) of telomeres (FIG. 15, top). Upon coexpression of dCas9, PP7~VP64, MS2~mCherry and both modified sgRNAs, both the induction of mCerulean CFP and the presence of mCherry nuclear foci (FIG. 15, lower right) were observed. Omission of either PP7~VP64 or MS2~mCherry was sufficient to ablate the corresponding function, without perturbing the orthogonal function (FIG. 15, upper right and lower left, respectively).

Example XIX

Autonomous RNA Domains

Figure 12:
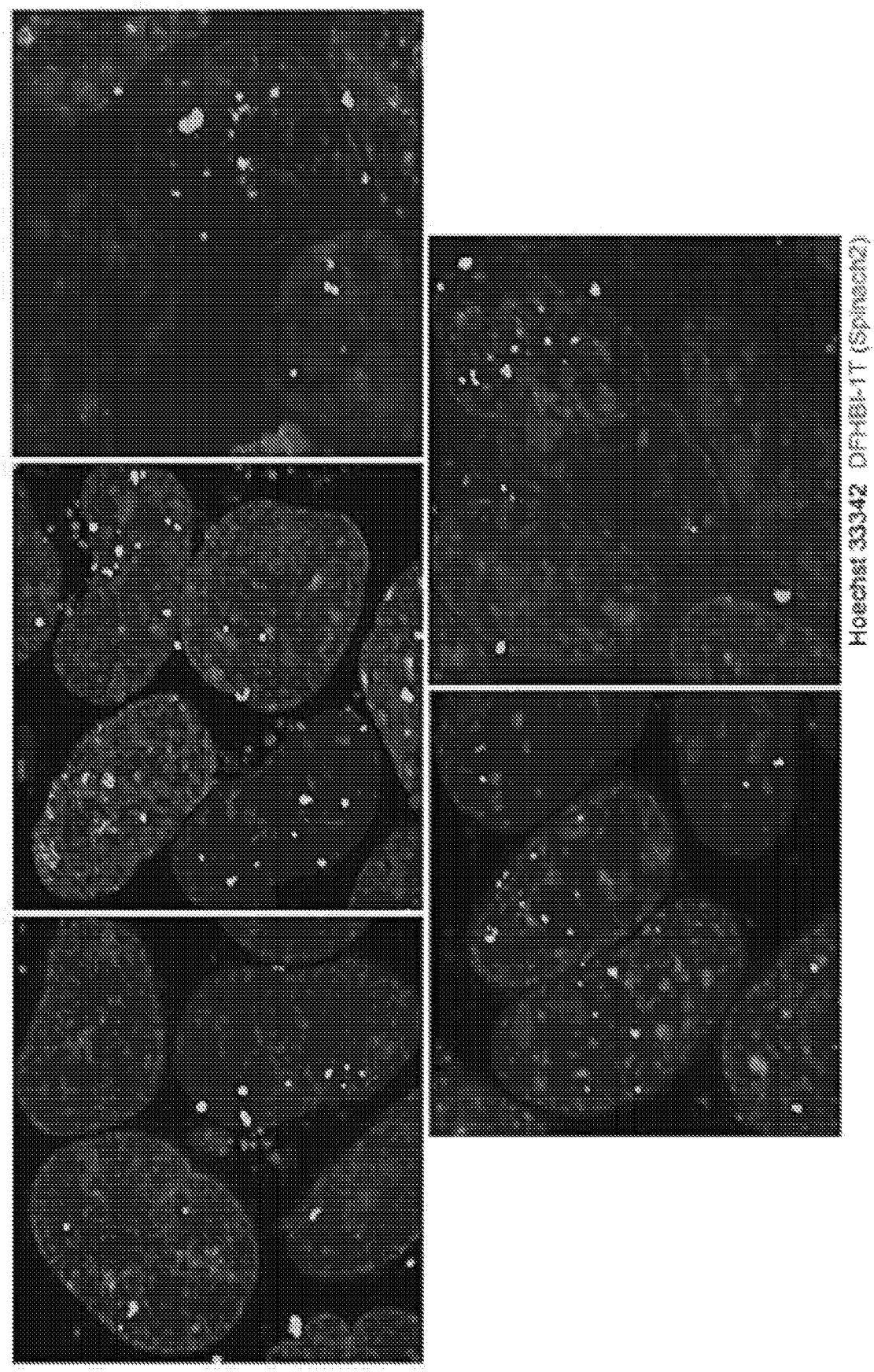
FIG. 12 is directed to additional representative aptamer-based live cell images. All cells are dCas9+, and express a telomere-targeting sgRNA internally appended with Spinach2 (see Table 5), akin to the lower-right field in FIG. 6C. Images are 63× magnification.

According to certain aspects, methods are provided for targeting autonomously functional RNA domains, such as ribozymes, aptamers and artificial regulatory devices to individual loci. With respect to all of the methods described herein, it is to be understood that a target DNA sequence can be any sequence in genomic DNA or chromosomal DNA to which one can design a guide RNA for forming a colocalization complex with an RNA guided DNA binding protein such as that in a CRISPR system, including genes, telomeres, introns, extrons, repetitive sequences, conserved sequences, nonconserved sequences, and the like. "Spinach2" is an artificial aptamer that binds to and induces fluorescence in a cell-permeable dye to telomeres. When a Spinach2-appended sgRNA targeting the TTAGGG telomere repeat was coexpressed with dCas9 and cells were treated with the Spinach2 ligand DFHBI-1T, numerous (10-20; average of 12, in ~20% of cells) nuclear fluorescent foci were observed (see FIG. 6C, bottom right, and FIG. 12). No fluorescent foci were observed in control experiments targeting the Spinach2 aptamer to the Gluc reporter (see FIG. 6C, bottom left), or with either Spinach2 construct in the absence of dCas9 (see FIG. 6C, top).

Figure 6D:
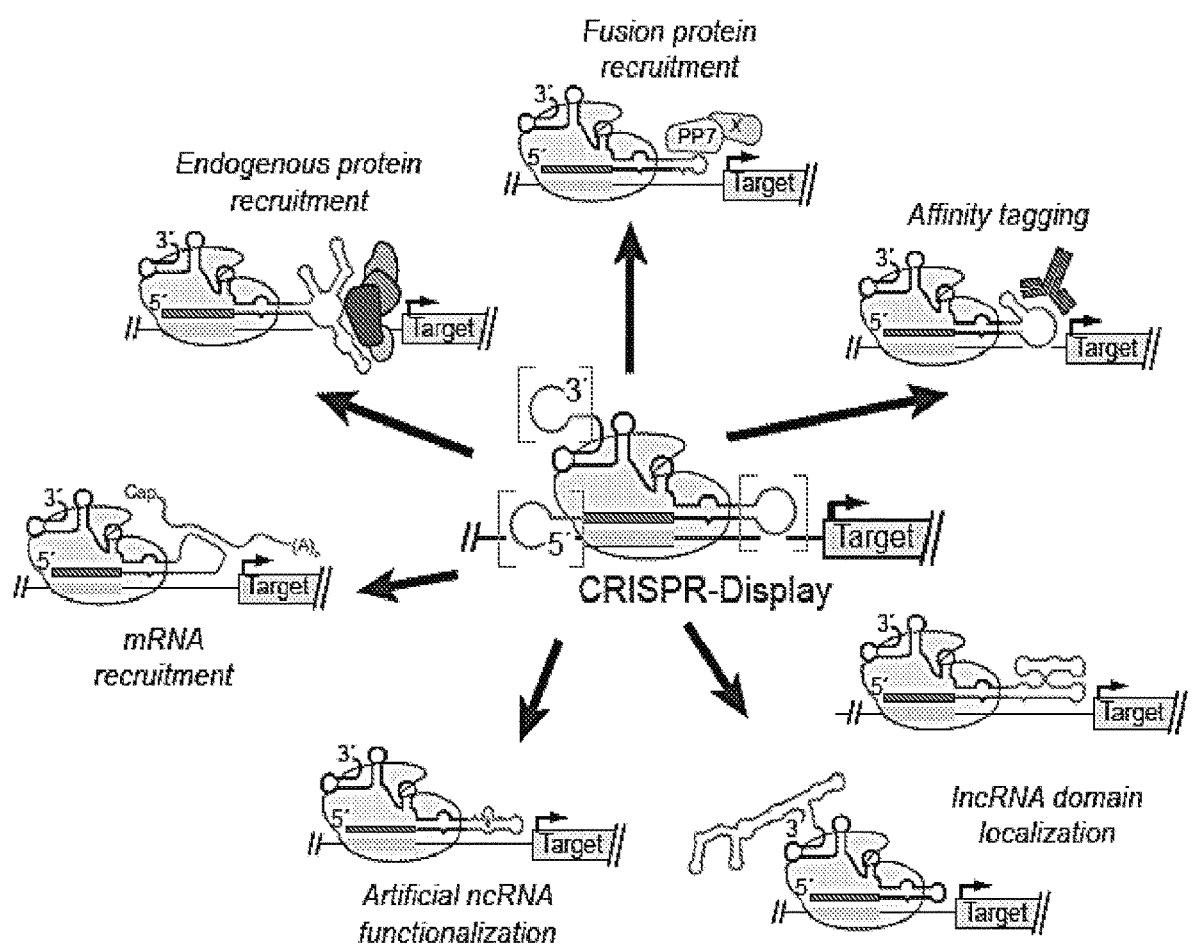

Additional aspects of attaching functional groups to guide RNA are shown in FIG. 6D. One such aspect comprises functional RNA groups that can be used to recruit one or more fusion proteins that have been co-expressed with dCas9 and the modified sgRNA. For example, PP7-fused to a FokI nuclease domain, to a histone methyltransferase, or to a fluorescent protein—can be recruited to a genomic locus via a modified sgRNA that is appended with cognate PP7 stem-loops. Another aspect comprises functional RNA groups that can be used as scaffolds to assemble proteins or their complexes. Examples would include RNA-templated protein fragment complementation, wherein a functional protein (i.e., an enzyme or fluorophore) is expressed as two non-self-assembling domains, each of which is fused to a different RNA-binding protein (i.e., MS2 and PP7). The fully functional protein (or complex) is thereafter assembled and targeted to genomic loci on a modified sgRNA bearing cassettes of each cognate protein-binding motif (i.e., MS2 and PP7 stem-loops). Another aspect comprises functional RNA groups that recruit one or more unmodified, endogenous proteins. Examples would include natural RNA domains that recruit the endogenous proteins with which they normally bind, or artificial aptamers that have been developed for this purpose. Another aspect comprises RNA groups that are autonomously functional, without the recruitment of additional proteins. Examples would include ribozymes, small-molecule-binding domains (including fluorophore and dye-binding domains), sensors and allosteric regulators that modulate the activity of Cas9. Another aspect comprises functional RNA groups that can be used as affinity tags. This would include protein-binding RNA modules (as described above), wherein the recruited protein can be affinity-purified through antibody or biochemical tagging method (i.e., FLAG-Tagged PP7), or RNA modules that can themselves be directly affinity-purified (i.e., the S1 streptavidin aptamer). Another aspect includes long noncoding RNAs (lncRNAs) and lncRNA domains. LncRNA function might be in part or fully reconstituted and re-targeted to specific loci.

TABLE 1

Sequences of the Target and Non-target cassettes in the "Reporter" and "Normalizer" constructs, respectively. Target/Non-Target motifs are in bold; PAM sequence are underlined; the minimal CMV Promoter is italicized.

| Construct | Sequence |
|---|---|
| Reporter (GLuc/mCerulean/ Hygro$^R$) | 5'-ATCTAGATACGACTCACTAT <u>AGG</u> CAAAGCTCTA-<br>ATCTAGATACGACTCACTAT <u>AGG</u> AAAGGAAGCAGCCAC-<br>ATCTAGATACGACTCACTAT <u>AGG</u> ATAACGTTAG-<br>ATCTAGATACGACTCACTAT <u>AGG</u> GTGAAGTAGTCTTTGCGGTA-<br>ATCTAGATACGACTCACTAT <u>AGG</u> CAAAGCTCTA-<br>ATCTAGATACGACTCACTAT <u>AGG</u> AAAGGAAGCAGCCAC-<br>ATCTAGATACGACTCACTAT <u>AGG</u> ATAACGTTAG-<br>ATCTAGATACGACTCACTAT <u>AGG</u> GTGAAGTAGT-<br>ATCTAGATACGACTCACTAT <u>AGG</u> ATCCACGTATGTCGAGG-<br>*TAGGCGTGTACGGTGGGAGGCCTATATAAGCAGAGCTCGTTTAGTGAACC*<br>*GTCAGATCGC*-3' (SEQ ID NO: 33) |
| Normalizer (CLuc/Venus/ Puro$^R$) | 5'-ATCTAGATCGCCCGTCCCCT <u>AGG</u> CAAAGCTCTA-<br>ATCTAGATCGCCCGTCCCCT <u>AGG</u> AAAGGAAGCAGCCAC-<br>ATCTAGATCGCCCGTCCCCT <u>AGG</u> ATAACGTTAG-<br>ATCTAGATCGCCCGTCCCCT <u>AGG</u> GTGAAGTAGTCTTTGCGGTA- |

TABLE 1-continued

Sequences of the Target and Non-target cassettes in the "Reporter" and "Normalizer" constructs, respectively. Target/Non-Target motifs are in bold; PAM sequence are underlined; the minimal CMV Promoter is italicized.

| Construct | Sequence |
|---|---|
| | ATCTAGATCGCCCGTCCCCT <u>AGG</u> CAAAGCTCTA-ATCTAGATCGCCCGTCCCCT <u>AGG</u> AAAGGAAGCAGCCAC-ATCTAGATCGCCCGTCCCCT <u>AGG</u> ATAACGTTAG-ATCTAGATCGCCCGTCCCCT <u>AGG</u> GTGAAGTAGT-ATCTAGATCGCCCGTCCCCT <u>AGG</u>CCGGATCCACGTATGTCGAGG-*TAGGCGTGTACGGTGGGAGGCCTATATAAGCAGAGCTCGTTTAGTGAACCGTCAGATCGC*-3' (SEQ ID NO: 34) |

TABLE 2

Guide RNA (gRNA) sequences used herein

| Target | Sequence |
|---|---|
| GLuc | GAUCUAGAUACGACUCACUAU (SEQ ID NO: 35) |
| ASCL1-1 | GCUGGGUGUCCCAUUGAAA (SEQ ID NO: 36) |
| ASCL1-2 | GCAGCCGCUCGCUGCAGCAG (SEQ ID NO: 37) |
| ASCL1-3 | GUGGAGAGUUUGCAAGGAGC (SEQ ID NO: 38) |
| ASCL1-4 | GUUUAUUCAGCCGGGAGUC (SEQ ID NO: 39) |
| IL1RN-1 | GUGUACUCUCUGAGGUGCUC (SEQ ID NO: 40) |
| IL1RN-2 | GACGCAGAUAAGAACCAGUU (SEQ ID NO: 41) |
| IL1RN-3 | GCAUCAAGUCAGCCAUCAGC (SEQ ID NO: 42) |
| IL1RN-4 | GAGUCACCCUCCUGGAAAC (SEQ ID NO: 43) |
| NTF3-1 | GAGCGCGGAGCCAUCUGGCC (SEQ ID NO: 44) |
| NTF3-2 | GCGCGGCGCGGAAGGGGUUA (SEQ ID NO: 45) |
| NTF3-3 | GCGGCGCGGCGCGGGCCGGC (SEQ ID NO: 46) |
| NTF3-5 | GCGGUUAUAACCAGCCAACC (SEQ ID NO: 47) |
| TTN-1 | GCCUUGGUGAAGUCUCCUUUG (SEQ ID NO: 48) |
| TTN-2 | GAUGUUAAAAUCCGAAAAUGC (SEQ ID NO: 49) |
| TTN-3 | GGGCACAGUCCUCAGGUUUG (SEQ ID NO: 50) |
| TTN-4 | GAUGAGCUCUCUUCAACGUUA (SEQ ID NO: 51) |
| Telomere | GUUAGGGUUAGGGUUAGGGUUA (SEQ ID NO: 52) |

TABLE 3 qPCR primers used in representative Examples, in the order cited

| Target | Forward Primer | Reverse Primer | Name[a] | Efficiency[b] |
|---|---|---|---|---|
| sgRNA (GLuc) | AGATACGACTCACTATGTTTAAGAGC (SEQ ID NO: 53) | TCAAGTTGATAACGGACTAGCCT (SEQ ID NO: 54) | p1 | 0.848 |
| P4-P6 | CAGCCGTTCAGTACCAAGTCT (SEQ ID NO: 55) | GGACCATGTCCGTCAGCTT (SEQ ID NO: 56) | p2 | 0.858 |
| GAPDH | TTCGACAGTCAGCCGCATCTTCTT (SEQ ID NO: 57) | GCCCAATACGACCAAATCCGTTGA (SEQ ID NO: 58) | | 0.847 |
| ASCL1 | GGAGCTTCTCGACTTCACCA (SEQ ID NO: 59) | AACGCCACTGACAAGAAAGC (SEQ ID NO: 60) | | 0.848 |
| IL1RN | GGAATCCATGGAGGGAAGAT (SEQ ID NO: 61) | TGTTCTCGCTCAGGTCAGTG (SEQ ID NO: 62) | | 0.827 |
| NTF3 | GATAAACACTGGAACTCTCAGTGCAA (SEQ ID NO: 63) | GCCAGCCCACGAGTTTATTGT (SEQ ID NO: 64) | | 0.851 |
| TTN | TGTTGCCACTGGTGCTAAAG (SEQ ID NO: 65) | ACAGCAGTCTTCTCCGCTTC (SEQ ID NO: 66) | | 0.851 |
| Double P4-P6 | GGATGCAGTTCACACCTCCA (SEQ ID NO: 67) | CCTTTCCCGCAATTCCGAAG (SEQ ID NO: 68) | p3 | 0.840 |
| pRNA_GSP1[c] | GTCGGTGACGCGACCT (SEQ ID NO: 69) | *TAACTTGCTACGAATACGAGTCC* (SEQ ID NO: 70) | | 0.892 |
| FALEC_GSP1 | GCAGGTTTCACAGAGGGAAGA (SEQ ID NO: 71) | CCACTGAGGACACCGACTAC (SEQ ID NO: 72) | | 0.852 |

TABLE 3-continued qPCR primers used in representative Examples, in the order cited

| Target | Forward Primer | Reverse Primer | Name[a] | Efficiency[b] |
|---|---|---|---|---|
| FALEC_GSP2 | AGTCGGTGTCCTCAGTGGTA (SEQ ID NO: 73) | AAGAGCAGGCTACAAGTGC T (SEQ ID NO: 74) | | 0.859 |
| TRERNA1_GSP1 | GTGGTTTTACGTGGCCGATT (SEQ ID NO: 75) | GCCTGACGTGAAGTAGCTTT (SEQ ID NO: 76) | | 0.873 |
| ncRNA-a3_GSP1 | AGTACCCGACGAGCGTTATG (SEQ ID NO: 77) | AGGCTGGTACAGATGGGTCT (SEQ ID NO: 78) | | 0.814 |
| ncRNA-a3_GSP2 | GGAGTTTGCAGTGAGCCAAG (SEQ ID NO: 79) | ACGAATCGAGAAAGAGCCT CA (SEQ ID NO: 80) | | 0.852 |
| RepA_GSP1[c] | *AGTCGGTGCTTCATTCACTCT* (SEQ ID NO: 81) | GCCCCGATGGGCGAATAA (SEQ ID NO: 82) | | 0.815 |
| RepA_GSP2 | GGGTTGTTGCACTCTCTGGA (SEQ ID NO: 83) | TCATTCTCTGCCAAAGCGGT (SEQ ID NO: 84) | | 0.884 |
| RepA_GSP3 | AAGGTCTTGCCGCAGTGTAA (SEQ ID NO: 85) | CAACGCCTGCCATATTGTCC (SEQ ID NO: 86) | | 0.845 |
| HOTTIP_GSP1 | ATGGTAGGGTGTTGGTGCTG (SEQ ID NO: 87) | CCCAGAACCCCTCGACAAA A (SEQ ID NO: 88) | | 0.861 |
| HOTTIP_GSP2 | TCTCGCCTCTGACTCTGTTC (SEQ ID NO: 89) | GAAGAGTCGGTAAACACCG C (SEQ ID NO: 90) | | 0.888 |
| HOTTIP_GSP3 | TTACGCCCGCAACAAAACAG (SEQ ID NO: 91) | CCCTCCTTCCTTCAAACGCT (SEQ ID NO: 92) | | 0.886 |
| HOTTIP_GSP4 | TTCCACCTTTGCCCGATACA (SEQ ID NO: 93) | GGAGATGGGTACCTAGGGG T (SEQ ID NO: 94) | | 0.871 |
| HOTTIP_GSP5 | GCTTGGCAACTTCAGAAAGC A (SEQ ID NO: 95) | AGCAGCCGGGTAGTGTAAA A (SEQ ID NO: 96) | | 0.871 |
| XIST | CCCTACTAGCTCCTCGGACA (SEQ ID NO: 97) | ACACATGCAGCGTGGTATCT (SEQ ID NO: 98) | | 0.850 |
| SNHG5 | GTGGACGAGTAGCCAGTGA A (SEQ ID NO: 99) | GCCTCTATCAATGGGCAGAC A (SEQ ID NO: 100) | | 0.844 |
| INT (GLuc) | CTCGTATTCGCAGCATAGCA A (SEQ ID NO: 101) | TTCAAGTTGATAACGGACTA GCCT (SEQ ID NO: 102) | pINT | 0.891 |

[a] As referred to herein
[b] As calculated using Realtime qPCR Miner
[c] Italicized nucleotides correspond to linker regions joining the lncRNA core to the sgRNA backbone

TABLE 4

Sequences of natural lncRNA constructs used herein pRNA
CGAUGGUGGCGUUUUUGGGGACAGGUGUCCGUGUCGCGUGUCGCGUCGCCUGGGCCGGCGGCGUGGUCGGUGA
CGCGACCUCCCGGCCCCGGGGA (SEQ ID NO: 103)

FALEC (ncRNA-a1)
GCGCAUCUCCUACGGCCUCCAGGACAGAGGAACCGGGGGAGGCAGGGGGAAAAGGCCGGCCCAGCAAUUCCCCUA
CCCCCCGGUCCCACGUGUACCCUCCUGGCCUGGGUCGCCCCAGCCCACGGGGAGCGGGCGGAGUCCUGGCCCACG
AAGCCUUGUCACCUGGCGGGCGAAUCCGCAAGCGGAGACUUGUCUUUAAAGGGCUUUGGGCCGGGCGCGGUGGCU
CAUGCCUGGAAUCCCAGCACUUUGGGAGGCCGAGGCGGUGGAUCACGAGGUCAGGAGUUCAAGACCAGCCUGGCC
AAGAAGCUCAUACUGACUAAGGCAGCAGAACAUACAGGAGGAAGAGGAGCAGGUUUCACAGAGGGAAGACAUGAG
UUCAAUUUUGGACUUCUCAGUAGUCGUGUGUCCUCAGUGGUAGCAACUUCAAACGGAAGGUGUCAAAAGUCAAAUU
CUGGAGAGUUGAGUAUGAAUGGGAGAUGAAGAAAAGGAGGCAGCACUUGUAGCCUGCUCUUAAUGUAUUUCUGCA
CUCUACACUAGCAGCCUAUUACACAGGACACUUGGAUGUCU (SEQ ID NO: 104)

TRERNA1 (ncRNA-a7)
CCGUUCCUGCCUCCCACAGACACCUAUUAAGUGCCUCCAGUUUUAGGAACUGGGUAUAGAUAUGGCUGGGAACAA
AAUGGAAGAAACAAAAACAAAAAUCCCUGCCCUCAUGGUGCUGACUCUCCUGUGGCAGAGACGGAGAAGAUGAA
CAGGGAUUUUAUACCAGGCGUCAGAAGGGAACCAGUGCUAAAGAAAAAUGAAAACACCAGGCCGGGAGAGGCAGCU
GGCAUGCGGGCCGUGGUGGUUUUACGUGGCCGAUUUGAGAGAGUGAGACCCCUGGGGUCUUUGGAGCCAGGCCUGG
GAAAAGCUACUUCACGUCAGGCCAGGGGCUGUAGCCCUGGCAACCUCCACUCCGCCUGGAAAUCCUCCACCUCGG

TABLE 4-continued

Sequences of natural lncRNA constructs used herein

GGCCUCUCUUUGCCCAGACCUGGCCCAGGAGGAGCACAUGGGAGCCGGGACCUUCCCAACAAUCCUUGCCGUUGG
CUCCACAAACCUCAGCCAGUCCUGCAACCUGGGAUGCCUUUUCCACCAGGAUGCCUGCUACUGUCACUGUUGUCA
UUAGAUAAUUAAUGAACUAUAAUUAGAAAUCAUAUCAAUAAAAUUUCACAGUCUAAGGCUGUUGAAAUAGG
(SEQ ID NO: 105)

ncRNA-a3
GAAGUUGAGCUUCAGGCGCGGCUCUUCCCCGUCACACUGGGACCGGACGCAUUUCCAUGGCGUGGUCCCAGGAAC
CUCUCAGAGUGAACUGAAUUGGAUGCAAGAUCACGGUGCGUCAGAGCUAGCAAGAUCCUUAGGAUCAUUUAGCCU
GGUUUACUAAUAUUACACUAUGGAAUUUAAGCCCAAGGAAUUGGAGAGUACCCGACGAGCGUUAUGUAAGGAGUCG
AGUGAGAAGUAAGCUGGAUGCUCUGCUUGGCUGGCAGGUACAGAAUGUGCCAGACCCAUCUGUACCAGCCUGGAU
CUCUUGAGGCAUCAGCACAAUGGACCUGGCCCACACCAGUUUAUUCCACACCGCUGAGGCUGGUCUUUGAGGAAUC
ACCACACUGUCUUCCACAAUGCACCAUGGAAUACUAUGCAGACAUAAAAAGGAAUGAGAUCAUGUCGUUUGCAGG
GACAUGGAUGGAGCUAGAAGCCAUUAUCCUCAGAAAACUAACACAGGAACAGAAAACCAAAUACCACAUGUUCUC
ACUUAUAAGUGGGAGCUGAAUGAUGAGAACACAUGGACACGUGGUGCGGGAACAAUACACCUGGGGCCUGUUGGA
GGGUGGGGGCUGGGAGGAGGGAGAGCAUCAAGAAUAGCUAAUGAGGCCAGGCACAGUGGCUCACGCCUGUAAUCC
UAGCAUUUUGGGAGGCUGAGGCGGGCAGAUCAUUUGAGGUCAGGAGUUUGAGACCAGCCUGGCCAAUAUGGUGAA
ACCCCGUCUCUAUUAAAAAUACAAAAAUAUUAGCCAGGCAUGGUGGCAAUGCCCGUAGUCCCUGCAACUUGGGAG
GCUGAGGCAGGAGAAUCGUUUGAACCUGGGAGGUGGAGUUUGCAGUGAGCCAAGAUCGCGCCACUGCACUCCAGC
CUGGGCGACAGAGUGAGGCUC (SEQ ID NO: 106)

RepA
CACUCUCUUUUCUAUAUUUUGCCCAUCGGGGCUGCGGAUACCUGGUUUUAUUAUUUUUCUUUGCCCAACGGGGC
CGUGGAUACCUGCCUUUUAAUUCUUUUUAUUCGCCCAUCGGGGCCGCGGAUACCUGCUUUUUAUUUUUUUUUCC
UUAGCCCAUCGGGGUAUCGGAUACCUGCUGAUUCCCUUCCCCUCUGAACCCCCAACACUCUGGCCCAUCGGGGUG
ACGGAUAUCUGCUUUUUAAAAAUUUUCUUUUUUUGGCCCAUCGGGGCUUCGGAUACCUGCUUUUUUUUUUUUUUAU
UUUUCCUUGCCCAUCGGGGCCUCGGAUACCUGCUUUAAUUUUUGUUUUUCUGGCCCAUCGGGGCCGCGGAUACCU
GCUUUGAUUUUUUUUUUUUCAUCGCCCAUCGGUGCUUUUUAUGGAUGAAAAAAAAUGUUGGUUUUGUGGGUUGUUUCA
CUCUCUGGAAUAUCUACACUUUUUUUUGCUGCUGAUCAUUUGGUGGUGUGUGAGUGUACCUACCGCUUUGGCAGA
GAAUGACUCUGCAGUUAAGCUAAGGGCGUGUUCAGAUUGUGGAGGAAAAGUGGCCGCCAUUUUAGACUUGCCGCA
UAACUCGGCUUAGGGCUAGUCGUUUGUGCUAAGUUAAACUAGGGAGGCAAGAUGGAUGAUAGCAGGUCAGGCAGA
GGAAGUCAUGUGCAUUGCAUGAGCUAAACCUAUCUGAAUGAAUUUGAUUUGGGGCUUGUUAGGAGCGUUUGCUGGAU
UGUUGUAUCGGGAGGCAGUAAGAAUCAUCUUUUUAUCAGUACAAGGGACUAGUUAAAAAUGGAAGGUUAGGAAAGA
CUAAGGUGCAGGGCUUAAAAAUGGCGAUUUUGACAUUGCGGCAUUGCUCAGCAUGGCGGGCUGUGCUUUGUUAGGU
UGUCCAAAAUGGCGGAUCCAGUUCUGUCGCAGUGUUCAAGUGGCGGGAAGGCCACAUCAUGAUGGGCGAGGCUUU
GUUAAGUGGUUAGCAUGGUGGUGGACAUGUGCCGGUCACACAGGAAAAGAUGGCGGCUGAAGGUCUUGCCGCAGUG
UAAAACAUGGCGGGCCUCUUUGUCUUUGCUGUGUGCUUUUCGUGUUUGGUUUUGCCGCAGGGACAAUAUGGCAGG
CGUUGUCAUAUGGUAUAUCAUGCUUUUGUCACGUGGACAUCAUGGCGGGCUUGCCGCAUUGUUAAAGAUGGCGGG
UUUUGCCGCCUAGUGCCACGCAGAGCGGGAGAAAAGGUGGGAUGGACAGUGCUGGAUUGCUGCAUAACCCAACCA
AUUAGAAAUGGGGUGGAAUUGAUCACAGCCAAUUAGAGCAGAAGAUGGAAUUAGACUGAUGACACACUGUCCAG
CUACUCAGCGAAGACCUGGGUGAAUUAGCAUGGCACUUCGCAGCUGUCUUUAGCCAGUCAGGAGAAAGAAGUGGA
GGGGCCACGUGUAUGUCUCCCAGUGGGCGGUACACC (SEQ ID NO: 107)

HOTTIP
GUGGGGCCCAGACCCGCGCAACCAGGCGGGGAGGGGAGGUGGGCGCGCGAUUGGGUUGCGAUCUGGAGCAGUGGG
GACAGGUCAGGAACCGGCGCGUAUUUCUGCAGUGAGACCACAGGACGGACAUCGGCGCCUUCGGCUUCGAUGGAG
UUGCGAUUUUGCUCUUUCCAGGGAAACAGUGGCAGGGUGUUUGCUGCUUAUCGGUUCCUGCGGAUAUGCCUGGGU
CCCAGGACAUUCCACUGGAGGCUUGGACUGCAUUUAGGAGCCCCUAUCCCUUCCCUGUCCACACUGUUAGUGAGC
AAUUUCAUAUGUUUGCAUUUAGACCCAUAGACUCAGAACGACUCACACACACACAGUGUACACUGACACA
CUCACAUUCGCACACUUAGGUAUACAGCCUGAUCCUUGCUCUGACCUGGUAACAACGCUUCCUCCUCCAGAGACU
UUGAGAUAGAGCGAGCGAUCCCUGUGCACCAUUCAUCCAUGCUCCCACCUCGCCAGUAUGGCUGGCUUAGUUCUG
GAAGGGGCUUAAGAGGAACAAGCCCCAGCUGUGCUUCGGCUGGGACUUAAACCCCCUUCUGGGCCCUAAAGCC
ACGCUUCUUUGUGGACCGGACCUGACUCUCCAGGAAUCUGGGAACCCGCUAUUUCACUCUAUUUUGGGACAAGAA
AAAGGGGCUCUUUGGGGCCACUUCCUGCCUUCCCCUCAAGUAGGAUCUCCAGCCUGCAGAGGGUGCCUAGUCCUU
CUUUGCCCAAGAACCAGUCCAAGAAGCCUUUCCUCUGUGCCUGGGAAAUGCAACCUUUUCUUGGGAGCAUGGUAG
GGUGUUGGUGCUGAAGAACCAAGCAGCGACCCGUCUUGUAGCUGCCAUGUUUUGUCGAGGGGUUCUGGGGGUCCU
GCUGCUUUAGAGCCACAUACUUCCACUUCCUGAUUCACUACUGGGCACUGUGAGCGUUGGCAGAUGCCUAGAAGAGGAACAAGA
CGUUCAAAGUGAAAGUGGGGCACAUUACCGGAAUAGUGCUGGGGAGAGUGCUGGAUUCUUUUCCACCCCAGGCGGA
CUGGUGAGAAGCCAGGCUUGGACCUGUCCUCUGCUCCUAGCUUGCACACUCAGCCCUAAACUCAGAGCAGCACGC
AUACCACCCCUCACACACACCCCACCAUCUGCUGUCUAAGGCCCCUGGGCUUCCUGCAGGAUCCAGACCAAUGUG
GCUGGGCUUGGGCUUUUAUCUGUCCUGAUCCUGGAUUUGUGCCUGACCAAUGUAAGUGUCGCCCAAUAAAACCUUC
UAUGACCCCCACACCAGCCACCCCCCACCAAGUGUGGCCCUUUCCUUCUUGACUUUUUAGCAGUUCUGGGUAAAU
AUUGAUUUGCCCCAGUUUACCUUCUCCCUGACUGGCAUUUGCAGACUCAGGAACUAGCCUCUGUAGGGACUUG
AUUUUUCUGUUACUUUCUGGCCGUUUCACCACCCCCCUUCCUCCCUCCAAGUGGGCAUUGUAAAACUCACAGUGAC
AAAGAGACAGAGUAGGGUUCUAGGCCCCUGUUCCUGGGGACUUGAAGGCGGUUUUACAUACUGGUCAGACACGGC
UGGAGGCCAAGGUCAAGUUGAAAGUUGCAGUCAGCCAGCAGCAAGGCCAUGCAGCGUGAGAGACACAGGCA
GCAGCAAAAGGCCCAUUGCCCACAUCCCCUCACUCUUUAAUUUUCUCUCUCUUUUUAAAAAUUCUGCCUCUGACUC
UGUUCGGCUGCCCAGAAUUUUUUGGUGCCUUCGUGGGGUUUUUGGGCGGUGUUUACCGACUCUUCUCUGCCUCC
GCCCUGCUCAGCCAGGGCUUUGAGCCUCUUCGGUUUUCCGGCCAGACCCGGAAAAACGAAAACACAGCUUGGGGA
GCCCCCACUAGCCGGCGCCUGUGCCAGCUCACCUCUGGCCAAGGCGCAGCGCUGCUGGUGCACGGCGGCCAAUGCC
CAGCUCCACAUUCUUCCCUCCCCCUCCCACUUCACCGUAGCCCCGAACCCUGCGCGCAGAGAAAGGGUCUCAGCU
CCACAGACGACUGGGUCCCUCCUCACCAAAAAUGGUGAGACAAGAUUUCAUCUGUCGGCCGAGGAGCCACAAGCA
GGUACCACAAAGCCACUAGUGCACAGGGACUCAGAAAAGACGGCAGGAGCCCAAGGAAAAACUCCAAUUUGAGUAC
AGCCCUGCCUUGUUUCCCCAGAGAGUCCUGAGCAAGGAGACCUCCACCCCACACACACCAUUUCAGAACAACC
AGGUUCCAGACUCCCAUGAGGAGCAUCUCCCACUGCAGAGCCUUGCCCAGCCGCCCCGGACUCCUCAGAGCUGG
CGCAAAUCCGUCCUCCAAAACUCGGCUCUGGAGGCCUAAGUGACUCCGAAGCCGGCGGCAGCCGCGGCAGCGG
CCGUGGUGGUGGAAGAGCUCUUUCCCCGACAGUGCCACUGAUCGCUCUUCACUGGAGCUGGAAACAGCCUUCGC
GGAAAGGACCGGAGCAUGCGUUAGAAGCAGAGGGAGCUUGGUGAAGGGCUCGGCUGGAAGGAGGAAACGCCUUCU
CGCAGUGCGCGGCCAGCCCGCGGGGGACACCGGCUUGCUGGACUGCAGGGGCCCGUGCCACCCAGGAAGUGACCU

TABLE 4-continued

Sequences of natural lncRNA constructs used herein

GCGGGUCACUCAGCCGGGGCGCUGGGCGAGCGCGGGACGGCCCGGAGAAUUCCGUGCGGCUGCGACGGGAAAAGG
ACGAGGGGUCUCUGUACCCGACGCUGCCACUGGCCCAAAGGAAUUUUACCCGCGAGCGCCCACCCCACCCUAGCU
UGAUGCUUACGCCCGCAACAAAACAGGAAACCAGGACUGGGCAGUGCAUUCUUUAAGUCAACAAAUACACUGAAG
ACUUCGAGCGUUUGAAGGAAGGAGGGGGUUUGCACGUAAGCCUGGCCCCGCCGGGCUCGGCUUUCUCGCUGAGAA
AGCGGCGCAGGCAGCCAGGCGGCCUGGGCCCGCGGGGGUCCAUCUCGCCCUAGACUCCUAAGAACUCCCACGGCC
CUGUUCCCAGCUGCGAAUUCUUAAUGCACAACGCGACGGAGGGAAGGAAAAUUCACCAGCGCAGCGACGAGGAAGG
GGAACUCAGGACCCCUUCAAGUACACACUGAGGUGUGAUCAGAGUUUUAUGGGCACUUUAUAUGCUGUAAUCAUA
ACGAUGUGUGUGCCUUGAUAUGCACGCAUAUUCACGCAUCAAACGUGCAUACACACACAGAGUGAAUGUGCGCAU
CCAAUGUCAUGUGGGUGAAAUACAAGCAUCAUACCCAGCCCUACGAAAAAAAAAAUUCACCCUGUCGGACCAGGCU
GGUGACAUACUUCGCUGGCGCAUCUCCCUUACUCACUCUUACUUUUCCGACCCCUACCAUUCCCUCUCCUGUGGC
UUGGUAAAUACACCUGCCCUCCGUGGAAGGUGAGUCCUGGACUGGCGUUGCCAGGUUCGCAUGUCCUCCCCAGAA
CCUCCGUCUGGCUCCAGGGACUCUCACUGAGCGGGUCUAGAGCACCCAGCACUUUUCAAGGAACAGCCGCGGUUC
CUUUGUCCCGCGGCUCCAGCCCCGUUCGGCCCAGCUCUCAGGGAAACGAAGCGCUCAGUAAGAACUUUUGAUAUU
AGUUUGUAUGGGUAUUUACACUCUGGUGAGGGGAGCUGAGUACGGAAGUUCCAUUAAUCAUACUCCAACCUUGGG
UUUAGAUAUUCAGUUUAUGGGUUUGGGAGAGGGAGUUUGCCGGAAAGAAAGCAUCAAGGUUGGCCGCUGACUCCAG
AGAAAUGAAAAGGGAGCAAGGUCGUUUUCUGUUUCUGGAAAUCAAGAAUUAGGAAUGGGCAACUACAGGUGCUAA
CCAACAGACCACUUUUUUGUUUUUUUGGUAGCCCUUUGGCAGGGAUAGUUUUUCCACCUUUGCCCGAUACAAUUUA
AAAAAAAAAAAUCCUUUUAUUAUGGAAUUUGUCAAACACACACAAGCAUAACAAACCCCUAGGUACCCAUCUCC
AAGUUUUGACCCCUAUUAUAAUUUCAUCUUCAGUGUUUUAUUAUCCACUUCCUCUCUCUCUAUCUUUAGUAUUUU
AAAGUAAAUCCCAGAUAGCAUCACAUCAUUUCACCCCCACCAUAGGAUUUCAAAGAUCUGUUUAUAUUUCAAGAUU
GAGUAAAAGGGCUUGAAAUUGGGUUAUUGCAAUGAAACUCUAGAAAAAGCUUGAGGGUUCACCCAGGAGUAAGCU
GGACAAAAAGGGGUUUGAGGGGUGGACCCAUCUUGCCUAAAAAUCUUGUCUCAUCUUUCUAAAAAUUACAUAUG
AAAGAGGAAGAUUUAUGUUACUUUUUUAUAUGAGAGAAUCGUCCUUUAAUAGAAAAUUUCUAUUGCUGCAUCAGA
AUUAUGGAGGAACACAAAAAACAUACCUCAGUCCUUAGUGUGUCCUAAAUUAACACAUAUUCACUUAUUAGUGGG
UAAAUGACUAUAUUUCAUUUCAGCACAACUUCUCCCCUGGUAGAAACACAAAAGAAAUUUCUAAUGAUUAAACUA
GGAAAGUUUGCACUGAAUUGAUGGCUUAUCAGAGCAACCGCAGUUUUCAGGAAGAAAUUCAAUGCCAUGCGUUGA
AAAUAUCCCCCUAGCAAUAAGGGAUUAUUUUUAAAAAAGAAUGAA
UAAAGAUGUUCUGGUUUCUUUUGUUUUAAUCUGGUAGUCUCAUUUACAACGAGCAUGAUUCUCCCUGUCGAACUC
UGAAAGUGACUUAACUGAAAGGCUUGGCAACUUCAGAAAGCAAAAAGGUAAAAACAGAAAAUAGCACACGGUUGA
AUUUGACAACUUUUACACUACCCGGCUGCUUAAUAAAUUCUAACCCCACUU (SEQ ID NO: 108)

TABLE 5

Sequences of the internal insertion ("INT-like") constructs. All constructs
including the constant backbone:
GAUCUAGAUACGACUCACUAUGUUUAAGAGCUAUGCUGCGAAUACGAGXXXX
CUCGUAUUCGCAGCAUAGCAAGUUUAAAUAAGGCUAGUCCGUUAUCAACUUG
AAAAAGUGGCACCGAGUCGGUGCUUUUUUU (SEQ ID NO: 109) . . . wherein XXXX is
replaced with the sequence below.

| Construct | Insert Sequence |
|---|---|
| 1xPP7 SL | GGAGCAGACGAUAUGGCGUCGCUCC (SEQ ID NO: 110) |
| S1 Aptamer | CCGACCAGAAUCAUGCAAGUGCGUAAGAUAGUCGCGGGCCGGC (SEQ ID NO: 111) |
| 3xMS2 SL | CGUACACCAUCAGGGUACGUCUCAGACACCAUCAGGGUCUGUCUGGUACAGCA UCAGCGUACC (SEQ ID NO: 112) |
| 3xCsy4 SL | UCUUACUGCUGUAUAAGCAGCUCUUACUGCCGUGUAGGCAGCUUCUACUUCU GUAUAAGAAGCUUUC (SEQ ID NO: 113) |
| 3xPP7 SL ("INT") | GGAGCAGACGAUAUGGCGUCGCUCCUCUCCACGAGAGCAUAUGGGCUCCGUGG UCUCCAGCAGACGAUAUGGCGUCGCUGG (SEQ ID NO: 114) |
| GFP Aptamer | GCUUCUGGACUGCGAUGGGAGCACGAAACGUCGUGGCGCAAUUGGGUGGGGA AAGUCCUUAAAAGAGGGCCACCACAGAAGCC (SEQ ID NO: 115) |
| Spinach2 | GAUGUAACUGAAUGAAAUGGUGAAGGACGGGUCCAGUAGGCUGCUUCGGCAG CCUACUUGUUGAGUAGAGUGUGAGCUCCGUA-ACUAGUUACAUC (SEQ ID NO: 116) |
| 3xK-T | UCUGCUCCCGUGAUGGCGAAAGCCUGAGGAGCUCUCUGGCCGUGAUGGCGAAA GCCUGAGCCAGUCUCUGCCCGUGAUGGCGAA-AGCCUGAGGCAGUCU (SEQ ID NO: 117) |
| Bunch of baby Spinach (BoBS) | AAGGACGGGUCCGGACGCAAGGACGGGUCCGACCGAAAGGACGGGUCCAAUGG UGGAAACACCAUUGUUGAGUAGAGUGUGAG-UCGGUCGUUGAGUAGAGUGUGAGGCGUCCGUUGAGUAGAGUGUGAG (SEQ ID NO: 118) |

TABLE 5-continued

Sequences of the internal insertion ("INT-like") constructs. All constructs including the constant backbone:
GAUCUAGAUACGACUCACUAUGUUUAAGAGCUAUGCUGCGAAUACGAGXXXX
CUCGUAUUCGCAGCAUAGCAAGUUUAAAUAAGGCUAGUCCGUUAUCAACUUG
AAAAAGUGGCACCGAGUCGGUGCUUUUUU (SEQ ID NO: 109) . . . wherein XXXX is replaced with the sequence below.

| Construct | Insert Sequence |
|---|---|
| 5xPP7 SL | GGAGCAGACGAUAUGGCGUCGCUCCUCUCCACGAGAGCAUAUGGGCUCCGUGG UCUGCAGCAGACGAUAUGGCGUCGCUGCUCU-CGUAGAUGCCAUAUGGGGCACUACGUCUCCAGCAGACGAUAUGGCGUCGCUGG (SEQ ID NO: 119) |
| P4-P6[3xPP7SL] | UCUGGAAUUGCGGGAAAGGGGUCAACAGCCGUUCAGUACCAAGUCUCAGGGG AAACUUUGAGAUGGCCUUGCAAAGGGUAUGG-UAAUAAGCUGACGGACAUGGUCCUAACACGCAGCCAAGUCCUAAGUCAACAG UCUGGAGCAGACGAUAUGGCGUCGCUCCUCUC-CACGAGAGCAUAUGGGCUCCGUGGUCUCCAGCAGACGAUAUGGCGUCGCUGGU CUCUGUUGAUAUGGAUGCAGUUCAUCU (SEQ ID NO: 120) |

TABLE 6

Amplification primers used to generate INT-N$_{25}$ sequencing libraries. XXXXXX corresponds to Illumina™ indexes 1-7.

| Primer | Sequence |
|---|---|
| RT Primer | CGACTCGGTGCCACTTTT (SEQ ID NO: 121) |
| Forward Library | CAAGCAGAAGACGGCATACGAGATXXXXXXGTGACT GGAGTTCAGACGTGTGCTCTTCCGATCT-TCAAGTTGATAACGGACTAGC (SEQ ID NO: 122) |
| Reverse Library | AATGATACGGCGACCACCGAGATCTACACTCTTTCCC TACACGACGCTCTTCCGATCTAGCTATG-CTGCGAATACGAG (SEQ ID NO: 123) |

The invention claimed is:

1. A method of delivering a selected RNA sequence to a target nucleic acid in a cell comprising
providing to the cell a Cas9 protein wherein the Cas9 protein is provided to the cell by introducing into the cell a first foreign nucleic acid encoding the Cas9 protein and
providing to the cell a guide RNA wherein the guide RNA is provided to the cell by introducing into the cell a second foreign nucleic acid encoding the guide RNA and a Pol II promoter sequence and a Pol II terminator sequence, wherein the Pol II promoter sequence is CMVPro or U1Pro and the Pol II terminator sequence is U1 3'Box, MASC or U2 smBox/U1 3'Box, wherein the guide RNA includes a spacer sequence and a tracr mate sequence forming a crRNA and a tracr sequence and has a selected RNA domain attached to the guide RNA,
wherein the guide RNA and the Cas9 protein are expressed, and
wherein the guide RNA and the Cas9 protein form a co-localization complex with the target nucleic acid to deliver the selected RNA sequence to the target nucleic acid.

2. The method of claim 1 wherein the guide RNA includes a selected RNA sequence attached to the 3' end of the tracr sequence.

3. The method of claim 1 wherein the guide RNA includes a selected RNA sequence attached to the 3' end of the tracr sequence and wherein the tracr sequence and the crRNA sequence may be separate or connected by the linker.

4. The method of claim 1 wherein the guide RNA includes a selected RNA sequence attached to the 5' end of the spacer sequence.

5. The method of claim 1 wherein the guide RNA includes a selected RNA sequence attached to the 5' end of the spacer sequence and wherein the tracr sequence and the crRNA sequence may be separate or connected by the linker.

6. The method of claim 1 wherein the crRNA and the tracr sequence of the guide RNA are separate sequences, and wherein the selected RNA sequence is attached to the 5' end of the tracr sequence or the 3' end of the crRNA sequence.

7. The method of claim 1 wherein the crRNA and the tracr sequence are connected by a linker sequence and the linker sequence includes the selected RNA sequence.

8. The method of claim 1 wherein the Cas9 protein is an enzymatically active Cas9 protein, a Cas9 protein nickase or a nuclease null or nuclease deficient Cas9 protein.

9. The method of claim 1 wherein the cell is in vitro, in vivo or ex vivo.

10. The method of claim 1 wherein the cell is a eukaryotic cell or prokaryotic cell.

11. The method of claim 1 wherein the cell is a bacteria cell, a yeast cell, a fungal cell, a mammalian cell, a plant cell or an animal cell.

12. The method of claim 1 wherein the selected RNA sequence is between about 10 and about 10,000 nucleotides; between about 20 and about 5,000 nucleotides; between about 30 and about 5,000 nucleotides; between about 40 and about 5,000 nucleotides; between about 50 and about 5,000 nucleotides; between about 60 and about 5,000 nucleotides; between about 70 and about 5,000 nucleotides; between about 80 and about 5,000 nucleotides; between about 90 and about 5,000 nucleotides; between about 100 and about 5,000 nucleotides; between about 110 and about 5,000 nucleotides; between about 120 and about 5,000 nucleotides; between about 130 and about 5,000 nucleotides; between about 140 and about 5,000 nucleotides; between about 150 and about 5,000 nucleotides; between about 175 and about 5,000 nucleotides; between about 200 and about 5,000 nucleotides; between about 250 and about 5,000 nucleotides; between about 300 and about 5,000 nucleotides; between about 400 and about 5,000 nucleotides; or between about 500 and about 5,000 nucleotides.

13. The method of claim 1 wherein the target nucleic acid is genomic DNA, mitochondrial DNA, plastid DNA, viral DNA, or exogenous DNA.

14. The method of claim 1 wherein the selected RNA sequence is an aptamer, a noncoding RNA, a ribozyme, a functional RNA sequence, a pool of random RNA sequences, an RNA scaffold, an RNA-based sensor or signal processor, an RNA-based signaling device, a naturally occurring long noncoding (lnc) RNA or a lnc subdomain, or a synthetic lncRNA, or synthetic lncRNA subdomain.

* * * * *

SEQUENCE LISTING

<160> NUMBER OF SEQ ID NOS: 123

<210> SEQ ID NO 1
<211> LENGTH: 113
<212> TYPE: DNA
<213> ORGANISM: ARTIFICIAL
<220> FEATURE:
<223> OTHER INFORMATION: sgRNA that targets the GLuc reporter

<400> SEQUENCE: 1
gaucuagaua cgacucacua uguuuaagag cuaugcugga aacagcauag caaguuuaaa    60
uaaggcuagu ccguuaucaa cuugaaaaag ugggcaccga gucggugcuu uuu           113

<210> SEQ ID NO 2
<211> LENGTH: 46
<212> TYPE: DNA
<213> ORGANISM: ARTIFICIAL
<220> FEATURE:
<223> OTHER INFORMATION: sgRNA that targets the GLuc reporter complimentary strand
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (26)..(26)
<223> OTHER INFORMATION: n is a, c, g, t or u

<400> SEQUENCE: 2
atctagatac gactcactat nggccnatag tgagtcgtat ctagat    46

<210> SEQ ID NO 3
<211> LENGTH: 25
<212> TYPE: DNA
<213> ORGANISM: ARTIFICIAL
<220> FEATURE:
<223> OTHER INFORMATION: functional guide RNA
<220> FEATURE:
<221> NAME/KEY: misc_feature
<222> LOCATION: (1)..(25)
<223> OTHER INFORMATION: n is a, c, g, t or u

<400> SEQUENCE: 3
nnnnnnnnnn nnnnnnnnnn nnnnn                                    25

<210> SEQ ID NO 4
<211> LENGTH: 160
<212> TYPE: RNA
<213> ORGANISM: ARTIFICIAL
<220> FEATURE:
<223> OTHER INFORMATION: intron P4-P6 domain

<400> SEQUENCE: 4
ggaauugcgg gaaagggguc aacagccguu caguaccaag ucucagggga aacuuugaga    60
uggccuugca aaggguaugg uuaauaagcu gacggacaug guccuaacac gcagucaagu   120
ccuaagucaa cagaucuucu guugauaugg augcaguuca                        160

<210> SEQ ID NO 5
<211> LENGTH: 95
<212> TYPE: RNA
<213> ORGANISM: ARTIFICIAL
<220> FEATURE:
<223> OTHER INFORMATION: 3xPP7 cassette

<400> SEQUENCE: 5
acagucugga gcagacgaua uggcgucgcu ccucuccacg agagcauaug ggcuccgugg    60
ucuccagcag acgauauggc gucgcugguc ucugu                              95

<210> SEQ ID NO 6
<211> LENGTH: 163
<212> TYPE: RNA
<213> ORGANISM: ARTIFICIAL
<220> FEATURE:
<223> OTHER INFORMATION: 5xPP7 cassette

<400> SEQUENCE: 6
acaguuuuug gagcagacga uauggcgucg cuccuuuuuc cagcagagca uaugggcucg    60
cugguuuuuc cagcagacga uauggcgucg cugguuuuug gagcagagca uaugggcucg   120
cuccuuuuug cagcagacga uauggcgucg cugcuuuuuc ugu                    163

<210> SEQ ID NO 7
<211> LENGTH: 133
<212> TYPE: RNA
<213> ORGANISM: ARTIFICIAL
<220> FEATURE:
<223> OTHER INFORMATION: 5xMS2 cassette

<400> SEQUENCE: 7
acaguuuuuc guacaccauc agggacguu uuucagacac caucaggguc uguuuuuggu    60
acagcaucag cguaccuuuu ucguacagga ucaccguacg uuuuucagac aggaucaccg   120
ucuguuuuuc ugu                                                    133

```
<210> SEQ ID NO 8
<211> LENGTH: 74
<212> TYPE: DNA
<213> ORGANISM: ARTIFICIAL
<220> FEATURE:
<223> OTHER INFORMATION: N25 pool
<220> FEATURE:
<221> NAME/KEY: misc_feature
<222> LOCATION: (26)..(50)
<223> OTHER INFORMATION: n is a, c, g, t or u

<400> SEQUENCE: 8
ttaagagcta tgctgcgaat acgagnnnnn nnnnnnnnnn nnnnnnnnnn ctcgtattcg      60
cagcatagca agtt                                                       74

<210> SEQ ID NO 9
<211> LENGTH: 26
<212> TYPE: DNA
<213> ORGANISM: ARTIFICIAL
<220> FEATURE:
<223> OTHER INFORMATION: N25 pool colony 1

<400> SEQUENCE: 9
atttgccttc cctggtagtt gcccat                                          26

<210> SEQ ID NO 10
<211> LENGTH: 24
<212> TYPE: DNA
<213> ORGANISM: ARTIFICIAL
<220> FEATURE:
<223> OTHER INFORMATION: N25 pool colony 2

<400> SEQUENCE: 10
acgacgtcaa cgtggtatga caga                                            24

<210> SEQ ID NO 11
<211> LENGTH: 25
<212> TYPE: DNA
<213> ORGANISM: ARTIFICIAL
<220> FEATURE:
<223> OTHER INFORMATION: N25 pool colony 3

<400> SEQUENCE: 11
aaggtatcaa accttccggc aagca                                           25

<210> SEQ ID NO 12
<211> LENGTH: 28
<212> TYPE: DNA
<213> ORGANISM: ARTIFICIAL
<220> FEATURE:
<223> OTHER INFORMATION: N25 pool colony 4

<400> SEQUENCE: 12
gttgatgtgg tggttcatgt tcgtaatc                                        28

<210> SEQ ID NO 13
<211> LENGTH: 33
<212> TYPE: DNA
<213> ORGANISM: ARTIFICIAL
<220> FEATURE:
<223> OTHER INFORMATION: N25 pool colony 5

<400> SEQUENCE: 13
ttatggggga tacggtggca ctagcggcaa aac                                  33

<210> SEQ ID NO 14
```

```
<211> LENGTH: 25
<212> TYPE: DNA
<213> ORGANISM: ARTIFICIAL
<220> FEATURE:
<223> OTHER INFORMATION: N25 pool colony 6

<400> SEQUENCE: 14
tttgaggcgt agagactagt ggggg                                            25

<210> SEQ ID NO 15
<211> LENGTH: 27
<212> TYPE: DNA
<213> ORGANISM: ARTIFICIAL
<220> FEATURE:
<223> OTHER INFORMATION: N25 pool colony 7

<400> SEQUENCE: 15
tgtaatgcga tttcaagatt catccgt                                          27

<210> SEQ ID NO 16
<211> LENGTH: 73
<212> TYPE: DNA
<213> ORGANISM: ARTIFICIAL
<220> FEATURE:
<223> OTHER INFORMATION: N25 pool primer design
<220> FEATURE:
<221> NAME/KEY: misc_feature
<222> LOCATION: (2)..(29)
<223> OTHER INFORMATION: n is a, c, g, t or u

<400> SEQUENCE: 16
gnnnnnnnnn nnnnnnnnnn nnnnnnnnnc tcgtattcgc agcatagcaa gtttaaataa     60
ggctagtccg tta                                                        73

<210> SEQ ID NO 17
<211> LENGTH: 94
<212> TYPE: RNA
<213> ORGANISM: ARTIFICIAL
<220> FEATURE:
<223> OTHER INFORMATION: secondary structure of the Spinach2 aptamer

<400> SEQUENCE: 17
gauguaacug aaugaaaugg ugaaggacgg guccagaggc ugcuucggca gccuacuugu     60
ugaguagagu gugagcuccg uaacuaguua cauc                                 94

<210> SEQ ID NO 18
<211> LENGTH: 149
<212> TYPE: RNA
<213> ORGANISM: ARTIFICIAL
<220> FEATURE:
<223> OTHER INFORMATION: minimal Spinach aptamer

<400> SEQUENCE: 18
cgaauacgag aaggacgggu ccggacgcaa ggacggaucc gaccgaaagg acggguccaa     60
ugguggaaac accauuguug aguagagugu gagucggucg uugaguagag ugugaggcgu    120
ccguugagua gagugugagc ucguauucg                                      149

<210> SEQ ID NO 19

<400> SEQUENCE: 19

000

<210> SEQ ID NO 20
```

<211> LENGTH: 1368
<212> TYPE: PRT
<213> ORGANISM: Streptococcus pyogenes

<400> SEQUENCE: 20

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
```

-continued

```
            385                 390                 395                 400
Lys Gln Arg Thr Phe Asp Asn Gly Ser Ile Pro His Gln Ile His Leu
                    405                 410                 415

Gly Glu Leu His Ala Ile Leu Arg Arg Gln Glu Asp Phe Tyr Pro Phe
                    420                 425                 430

Leu Lys Asp Asn Arg Glu Lys Ile Glu Lys Ile Leu Thr Phe Arg Ile
                    435                 440                 445

Pro Tyr Tyr Val Gly Pro Leu Ala Arg Gly Asn Ser Arg Phe Ala Trp
                    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                    485                 490                 495

Asn Phe Asp Lys Asn Leu Pro Asn Glu Lys Val Leu Pro Lys His Ser
                    500                 505                 510

Leu Leu Tyr Glu Tyr Phe Thr Val Tyr Asn Glu Leu Thr Lys Val Lys
                    515                 520                 525

Tyr Val Thr Glu Gly Met Arg Lys Pro Ala Phe Leu Ser Gly Glu Gln
                    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                    565                 570                 575

Ser Val Glu Ile Ser Gly Val Glu Asp Arg Phe Asn Ala Ser Leu Gly
                    580                 585                 590

Thr Tyr His Asp Leu Leu Lys Ile Ile Lys Asp Lys Asp Phe Leu Asp
                    595                 600                 605

Asn Glu Glu Asn Glu Asp Ile Leu Glu Asp Ile Val Leu Thr Leu Thr
                    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                    645                 650                 655

Thr Gly Trp Gly Arg Leu Ser Arg Lys Leu Ile Asn Gly Ile Arg Asp
                    660                 665                 670

Lys Gln Ser Gly Lys Thr Ile Leu Asp Phe Leu Lys Ser Asp Gly Phe
                    675                 680                 685

Ala Asn Arg Asn Phe Met Gln Leu Ile His Asp Asp Ser Leu Thr Phe
                    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                    725                 730                 735

Ile Leu Gln Thr Val Lys Val Val Asp Glu Leu Val Lys Val Met Gly
                    740                 745                 750

Arg His Lys Pro Glu Asn Ile Val Ile Glu Met Ala Arg Glu Asn Gln
                    755                 760                 765

Thr Thr Gln Lys Gly Gln Lys Asn Ser Arg Glu Arg Met Lys Arg Ile
                    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                    805                 810                 815
```

```
Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215
```

```
                                -continued

Glu Leu Gln Lys Gly Asn Glu Leu Ala Leu Pro Ser Lys Tyr Val
1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
1250                1255                1260

His Tyr Leu Asp Glu Ile Ile Glu Gln Ile Ser Glu Phe Ser Lys
1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
1310                1315                1320

Phe Lys Tyr Phe Asp Thr Thr Ile Asp Arg Lys Arg Tyr Thr Ser
1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
1355                1360                1365

<210> SEQ ID NO 21
<211> LENGTH: 151
<212> TYPE: DNA
<213> ORGANISM: ARTIFICIAL
<220> FEATURE:
<223> OTHER INFORMATION: cloning vector

<400> SEQUENCE: 21
gatctagata cgactcacta tgtttaagag ctatgctgcg aatacgagaa gtcttctttt      60
ttgaagacaa tcgtattcgc agcatagcaa gtttaaataa ggctagtccg ttatcaactt     120
gaaaaagtgg caccgagtcg gtgcttttt t                                     151

<210> SEQ ID NO 22
<211> LENGTH: 51
<212> TYPE: DNA
<213> ORGANISM: ARTIFICIAL
<220> FEATURE:
<223> OTHER INFORMATION: primer
<220> FEATURE:
<221> NAME/KEY: misc_feature
<222> LOCATION: (14)..(26)
<223> OTHER INFORMATION: n denotes nucleotides 9 to 21 of the new
      protospacer sequence

<400> SEQUENCE: 22
tagtagaaga caannnnnnn nnnnngttt aagagctatg ctgcgaatac g                51

<210> SEQ ID NO 23
<211> LENGTH: 44
<212> TYPE: DNA
<213> ORGANISM: ARTIFICIAL
<220> FEATURE:
<223> OTHER INFORMATION: primer
<220> FEATURE:
<221> NAME/KEY: misc_feature
<222> LOCATION: (14)..(25)
<223> OTHER INFORMATION: n denotes reverse compl. of nucleotides 1 to 9
      of new protospacer

<400> SEQUENCE: 23
tagtagaaga caannnnnnn nnnnnggtgt tcgtcctttt ccac                       44
```

```
<210> SEQ ID NO 24
<211> LENGTH: 82
<212> TYPE: DNA
<213> ORGANISM: ARTIFICIAL
<220> FEATURE:
<223> OTHER INFORMATION: constructs employing the U1 3 prime box
      terminator

<400> SEQUENCE: 24
actttctgga gtttcaaaag tagactgtac gctaagggtc atatcttttt ttgtttggtt     60
tgtgtcttgg ttggcgtctt aa                                             82

<210> SEQ ID NO 25
<211> LENGTH: 393
<212> TYPE: DNA
<213> ORGANISM: ARTIFICIAL
<220> FEATURE:
<223> OTHER INFORMATION: promoter

<400> SEQUENCE: 25
ctaaggacca gcttctttgg gagagaacag acgcaggggc gggagggaaa aagggagagg     60
cagacgtcac ttcccttgg cggctctggc agcagattgg tcggttgagt ggcagaaagg    120
cagacgggga ctgggcaagg cactgtcggt gacatcacgg acaggcgac ttctatgtag    180 atgaggcagc gcagaggctg ctgcttcgcc acttgctgct tcaccacgaa ggagttcccg    240
tgccctggga gcgggttcag gaccgctgat cggaagtgag aatcccagct gtgtgtcagg    300
gctggaaagg gctcgggagt gcgcggggca agtgaccgtg tgtgtaaaga gtgaggcgta    360
tgaggctgtg tcggggcaga ggcccaagat ctc                                 393

<210> SEQ ID NO 26
<211> LENGTH: 203
<212> TYPE: DNA
<213> ORGANISM: ARTIFICIAL
<220> FEATURE:
<223> OTHER INFORMATION: promoter

<400> SEQUENCE: 26
cagcaagttc agagaaatct gaacttgctg gattttttgga gcagggagat ggaataggag     60
cttgctccgt ccactccacg catcgacctg gtattgcagt acctccagga acggtgcacc    120
cactttctgg agtttcaaaa gtagactgta cgctaagggt catatctttt tttgtttggt    180
ttgtgtcttg gttggcgtct taa                                            203

<210> SEQ ID NO 27
<211> LENGTH: 174
<212> TYPE: DNA
<213> ORGANISM: ARTIFICIAL
<220> FEATURE:
<223> OTHER INFORMATION: promoter

<400> SEQUENCE: 27
gattcgtcag tagggttgta aaggtttttc ttttcctgag aaaacaacct tttgttttct     60
caggttttgc ttttttggcct ttccctagct ttaaaaaaaa aaaagcaaaa gacgctggtg   120
gctggcactc ctggtttcca ggacggggtt caagtccctg cggtgtcttt gctt          174

<210> SEQ ID NO 28
<211> LENGTH: 82
<212> TYPE: DNA
<213> ORGANISM: ARTIFICIAL
```

-continued

```
<220> FEATURE:
<223> OTHER INFORMATION: promoter

<400> SEQUENCE: 28
actttctgga gtttcaaaag tagactgtac gctaagggtc atatctttt    60 tgtgtcttgg ttggcgtctt aa                                  82

<210> SEQ ID NO 29
<211> LENGTH: 174
<212> TYPE: DNA
<213> ORGANISM: ARTIFICIAL
<220> FEATURE:
<223> OTHER INFORMATION: promoter

<400> SEQUENCE: 29
gattcgtcag tagggttgta aaggttttc ttttcctgag aaaacaacct tttgttttct    60
caggttttgc ttttggcct tccctagct ttaaaaaaa aaaagcaaaa gacgctggtg     120
gctggcactc ctggtttcca ggacggggtt caagtccctg cggtgtcttt gctt         174

<210> SEQ ID NO 30
<211> LENGTH: 596
<212> TYPE: DNA
<213> ORGANISM: ARTIFICIAL
<220> FEATURE:
<223> OTHER INFORMATION: promoter

<400> SEQUENCE: 30
ctaaggacca gcttctttgg gagagaacag acgcaggggc gggagggaaa aagggagagg    60
cagacgtcac ttccccttgg cggctctggc agcagattgg tcggttgagt ggcagaaagg    120
cagacgggga ctgggcaagg cactgtcggt gacatcacgg acagggcgac ttctatgtag    180
atgaggcagc gcagaggctg ctgcttcgcc acttgctgct tcaccacgaa ggagttcccg    240
tgccctggga gcgggttcag gaccgctgat cggaagtgag aatcccagct gtgtgtcagg    300
gctggaaagg gctcggagt gcgcggggca agtgaccgtg tgtgtaaaga gtgaggcgta     360
tgaggctgtg tcggggcaga ggcccaagat ctccagcaag ttcagagaaa tctgaacttg    420
ctggattttt ggagcaggga gatggaatag gagcttgctc cgtccactcc acgcatcgac    480
ctggtattgc agtacctcca ggaacggtgc acccactttc tggagtttca aaagtagact    540
gtacgctaag ggtcatatct tttttgtttt ggtttgtgtc ttggttggcg tcttaa       596

<210> SEQ ID NO 31
<211> LENGTH: 30
<212> TYPE: DNA
<213> ORGANISM: ARTIFICIAL
<220> FEATURE:
<223> OTHER INFORMATION: pool oligo
<220> FEATURE:
<221> NAME/KEY: misc_feature
<222> LOCATION: (5)..(29)
<223> OTHER INFORMATION: n is a, c, g, t or u

<400> SEQUENCE: 31
cgagnnnnnn nnnnnnnnnn nnnnnnnnnc                                    30

<210> SEQ ID NO 32
<211> LENGTH: 30
<212> TYPE: DNA
<213> ORGANISM: ARTIFICIAL
<220> FEATURE:
<223> OTHER INFORMATION: pool oligo
<220> FEATURE:
```

```
<221> NAME/KEY: misc_feature
<222> LOCATION: (6)..(30)
<223> OTHER INFORMATION: n is a, c, g, t or u

<400> SEQUENCE: 32
acgagnnnnn nnnnnnnnnn nnnnnnnnnn                              30

<210> SEQ ID NO 33
<211> LENGTH: 384
<212> TYPE: DNA
<213> ORGANISM: ARTIFICIAL
<220> FEATURE:
<223> OTHER INFORMATION: reporter

<400> SEQUENCE: 33
atctagatac gactcactat aggcaaagct ctaatctaga tacgactcac tataggaaag    60
gaagcagcca catctagata cgactcacta taggataacg ttagatctag atacgactca   120 ctataggtg aagtagtctt tgcggtaatc tagatacgac tcactatagg caaagctcta   180
atctagatac gactcactat aggaaaggaa gcagccacat ctagatacga ctcactatag   240
gataacgtta gatctagata cgactcacta tagggtgaag tagtatctag atacgactca   300
ctataggatc cacgtatgtc gaggtaggcg tgtacggtgg gaggcctata taagcagagc   360
tcgtttagtg aaccgtcaga tcgc                                         384

<210> SEQ ID NO 34
<211> LENGTH: 388
<212> TYPE: DNA
<213> ORGANISM: ARTIFICIAL
<220> FEATURE:
<223> OTHER INFORMATION: normalizer

<400> SEQUENCE: 34
atctagatcg cccgtccct aggcaaagct ctaatctaga tcgcccgtcc cctaggaaag    60
gaagcagcca catctagatc gcccgtccc taggataacg ttagatctag atcgcccgtc   120
ccctagggtg aagtagtctt tgcggtaatc tagatcgccc gtccctagg caaagctcta   180 atctagatcg cccgtccct aggaaaggaa gcagccacat ctagatcgcc cgtccctag   240 gataacgtta gatctagatc gcccgtcccc tagggtgaag tagtatctag atcgcccgtc   300
ccctaggccg gatccacgta tgtcgaggta ggcgtgtacg gtgggaggcc tatataagca   360
gagctcgttt agtgaaccgt cagatcgc                                    388

<210> SEQ ID NO 35
<211> LENGTH: 21
<212> TYPE: RNA
<213> ORGANISM: ARTIFICIAL
<220> FEATURE:
<223> OTHER INFORMATION: gRNA

<400> SEQUENCE: 35
gaucuagaua cgacucacua u                                            21

<210> SEQ ID NO 36
<211> LENGTH: 19
<212> TYPE: RNA
<213> ORGANISM: ARTIFICIAL
<220> FEATURE:
<223> OTHER INFORMATION: gRNA

<400> SEQUENCE: 36
gcuggguguc ccauugaaa                                               19
```

```
<210> SEQ ID NO 37
<211> LENGTH: 20
<212> TYPE: RNA
<213> ORGANISM: ARTIFICIAL
<220> FEATURE:
<223> OTHER INFORMATION: gRNA

<400> SEQUENCE: 37
gcagccgcuc gcugcagcag                                              20

<210> SEQ ID NO 38
<211> LENGTH: 20
<212> TYPE: RNA
<213> ORGANISM: ARTIFICIAL
<220> FEATURE:
<223> OTHER INFORMATION: gRNA

<400> SEQUENCE: 38
guggagaguu ugcaaggagc                                              20

<210> SEQ ID NO 39
<211> LENGTH: 19
<212> TYPE: RNA
<213> ORGANISM: ARTIFICIAL
<220> FEATURE:
<223> OTHER INFORMATION: gRNA

<400> SEQUENCE: 39
guuuauucag ccgggaguc                                               19

<210> SEQ ID NO 40
<211> LENGTH: 20
<212> TYPE: RNA
<213> ORGANISM: ARTIFICIAL
<220> FEATURE:
<223> OTHER INFORMATION: gRNA

<400> SEQUENCE: 40
guguacucuc ugaggugcuc                                              20

<210> SEQ ID NO 41
<211> LENGTH: 20
<212> TYPE: RNA
<213> ORGANISM: ARTIFICIAL
<220> FEATURE:
<223> OTHER INFORMATION: gRNA

<400> SEQUENCE: 41
gacgcagaua agaaccaguu                                              20

<210> SEQ ID NO 42
<211> LENGTH: 20
<212> TYPE: RNA
<213> ORGANISM: ARTIFICIAL
<220> FEATURE:
<223> OTHER INFORMATION: gRNA

<400> SEQUENCE: 42
gcaucaaguc agccaucagc                                              20

<210> SEQ ID NO 43
<211> LENGTH: 19
<212> TYPE: RNA
<213> ORGANISM: ARTIFICIAL
<220> FEATURE:
```

-continued

<223> OTHER INFORMATION: gRNA

<400> SEQUENCE: 43
gagucacccu ccuggaaac                                        19

<210> SEQ ID NO 44
<211> LENGTH: 20
<212> TYPE: RNA
<213> ORGANISM: ARTIFICIAL
<220> FEATURE:
<223> OTHER INFORMATION: gRNA

<400> SEQUENCE: 44
gagcgcggag ccaucuggcc                                       20

<210> SEQ ID NO 45
<211> LENGTH: 20
<212> TYPE: RNA
<213> ORGANISM: ARTIFICIAL
<220> FEATURE:
<223> OTHER INFORMATION: gRNA

<400> SEQUENCE: 45
gcgcggcgcg gaagggguua                                       20

<210> SEQ ID NO 46
<211> LENGTH: 20
<212> TYPE: RNA
<213> ORGANISM: ARTIFICIAL
<220> FEATURE:
<223> OTHER INFORMATION: gRNA

<400> SEQUENCE: 46
gcggcgcggc gcgggccggc                                       20

<210> SEQ ID NO 47
<211> LENGTH: 20
<212> TYPE: RNA
<213> ORGANISM: ARTIFICIAL
<220> FEATURE:
<223> OTHER INFORMATION: gRNA

<400> SEQUENCE: 47
gcgguuauaa ccagccaacc                                       20

<210> SEQ ID NO 48
<211> LENGTH: 21
<212> TYPE: RNA
<213> ORGANISM: ARTIFICIAL
<220> FEATURE:
<223> OTHER INFORMATION: gRNA

<400> SEQUENCE: 48
gccuugguga agucuccuuu g                                     21

<210> SEQ ID NO 49
<211> LENGTH: 21
<212> TYPE: RNA
<213> ORGANISM: ARTIFICIAL
<220> FEATURE:
<223> OTHER INFORMATION: gRNA

<400> SEQUENCE: 49
gauguuaaaa uccgaaaaug c                                     21

<210> SEQ ID NO 50
<211> LENGTH: 20
<212> TYPE: RNA
<213> ORGANISM: ARTIFICIAL
<220> FEATURE:
<223> OTHER INFORMATION: gRNA

<400> SEQUENCE: 50
gggcacaguc cucagguuug                                             20

<210> SEQ ID NO 51
<211> LENGTH: 21
<212> TYPE: RNA
<213> ORGANISM: ARTIFICIAL
<220> FEATURE:
<223> OTHER INFORMATION: gRNA

<400> SEQUENCE: 51
gaugagcucu cuucaacguu a                                           21

<210> SEQ ID NO 52
<211> LENGTH: 22
<212> TYPE: RNA
<213> ORGANISM: ARTIFICIAL
<220> FEATURE:
<223> OTHER INFORMATION: gRNA

<400> SEQUENCE: 52
guuaggguua ggguuagggu ua                                          22

<210> SEQ ID NO 53
<211> LENGTH: 26
<212> TYPE: DNA
<213> ORGANISM: ARTIFICIAL
<220> FEATURE:
<223> OTHER INFORMATION: primer

<400> SEQUENCE: 53
agatacgact cactatgttt aagagc                                      26

<210> SEQ ID NO 54
<211> LENGTH: 23
<212> TYPE: DNA
<213> ORGANISM: ARTIFICIAL
<220> FEATURE:
<223> OTHER INFORMATION: primer

<400> SEQUENCE: 54
tcaagttgat aacggactag cct                                         23

<210> SEQ ID NO 55
<211> LENGTH: 21
<212> TYPE: DNA
<213> ORGANISM: ARTIFICIAL
<220> FEATURE:
<223> OTHER INFORMATION: primer

<400> SEQUENCE: 55
cagccgttca gtaccaagtc t                                           21

<210> SEQ ID NO 56
<211> LENGTH: 19
<212> TYPE: DNA
<213> ORGANISM: ARTIFICIAL
<220> FEATURE:
<223> OTHER INFORMATION: primer

<400> SEQUENCE: 56
ggaccatgtc cgtcagctt                19

<210> SEQ ID NO 57
<211> LENGTH: 24
<212> TYPE: DNA
<213> ORGANISM: ARTIFICIAL
<220> FEATURE:
<223> OTHER INFORMATION: primer

<400> SEQUENCE: 57
ttcgacagtc agccgcatct tctt            24

<210> SEQ ID NO 58
<211> LENGTH: 24
<212> TYPE: DNA
<213> ORGANISM: ARTIFICIAL
<220> FEATURE:
<223> OTHER INFORMATION: primer

<400> SEQUENCE: 58
gcccaatacg accaaatccg ttga            24

<210> SEQ ID NO 59
<211> LENGTH: 20
<212> TYPE: DNA
<213> ORGANISM: ARTIFICIAL
<220> FEATURE:
<223> OTHER INFORMATION: primer

<400> SEQUENCE: 59
ggagcttctc gacttcacca                20

<210> SEQ ID NO 60
<211> LENGTH: 20
<212> TYPE: DNA
<213> ORGANISM: ARTIFICIAL
<220> FEATURE:
<223> OTHER INFORMATION: primer

<400> SEQUENCE: 60
aacgccactg acaagaaagc                20

<210> SEQ ID NO 61
<211> LENGTH: 20
<212> TYPE: DNA
<213> ORGANISM: ARTIFICIAL
<220> FEATURE:
<223> OTHER INFORMATION: primer

<400> SEQUENCE: 61
ggaatccatg gagggaagat                20

<210> SEQ ID NO 62
<211> LENGTH: 20
<212> TYPE: DNA
<213> ORGANISM: ARTIFICIAL
<220> FEATURE:
<223> OTHER INFORMATION: primer

<400> SEQUENCE: 62
tgttctcgct caggtcagtg                20

<210> SEQ ID NO 63
<211> LENGTH: 26

```
<212> TYPE: DNA
<213> ORGANISM: ARTIFICIAL
<220> FEATURE:
<223> OTHER INFORMATION: primer

<400> SEQUENCE: 63
gataaacact ggaactctca gtgcaa                                          26

<210> SEQ ID NO 64
<211> LENGTH: 21
<212> TYPE: DNA
<213> ORGANISM: ARTIFICIAL
<220> FEATURE:
<223> OTHER INFORMATION: primer

<400> SEQUENCE: 64
gccagcccac gagtttattg t                                               21

<210> SEQ ID NO 65
<211> LENGTH: 20
<212> TYPE: DNA
<213> ORGANISM: ARTIFICIAL
<220> FEATURE:
<223> OTHER INFORMATION: primer

<400> SEQUENCE: 65
tgttgccact ggtgctaaag                                                 20

<210> SEQ ID NO 66
<211> LENGTH: 20
<212> TYPE: DNA
<213> ORGANISM: ARTIFICIAL
<220> FEATURE:
<223> OTHER INFORMATION: primer

<400> SEQUENCE: 66
acagcagtct tctccgcttc                                                 20

<210> SEQ ID NO 67
<211> LENGTH: 20
<212> TYPE: DNA
<213> ORGANISM: ARTIFICIAL
<220> FEATURE:
<223> OTHER INFORMATION: primer

<400> SEQUENCE: 67
ggatgcagtt cacacctcca                                                 20

<210> SEQ ID NO 68
<211> LENGTH: 20
<212> TYPE: DNA
<213> ORGANISM: ARTIFICIAL
<220> FEATURE:
<223> OTHER INFORMATION: primer

<400> SEQUENCE: 68
cctttcccgc aattccgaag                                                 20

<210> SEQ ID NO 69
<211> LENGTH: 16
<212> TYPE: DNA
<213> ORGANISM: ARTIFICIAL
<220> FEATURE:
<223> OTHER INFORMATION: primer

<400> SEQUENCE: 69
```

```
gtcggtgacg cgacct                                                          16

<210> SEQ ID NO 70
<211> LENGTH: 23
<212> TYPE: DNA
<213> ORGANISM: ARTIFICIAL
<220> FEATURE:
<223> OTHER INFORMATION: primer

<400> SEQUENCE: 70
taacttgcta cgaatacgag tcc                                                  23

<210> SEQ ID NO 71
<211> LENGTH: 21
<212> TYPE: DNA
<213> ORGANISM: ARTIFICIAL
<220> FEATURE:
<223> OTHER INFORMATION: primer

<400> SEQUENCE: 71
gcaggtttca cagagggaag a                                                    21

<210> SEQ ID NO 72
<211> LENGTH: 20
<212> TYPE: DNA
<213> ORGANISM: ARTIFICIAL
<220> FEATURE:
<223> OTHER INFORMATION: primer

<400> SEQUENCE: 72
ccactgagga caccgactac                                                      20

<210> SEQ ID NO 73
<211> LENGTH: 20
<212> TYPE: DNA
<213> ORGANISM: ARTIFICIAL
<220> FEATURE:
<223> OTHER INFORMATION: primer

<400> SEQUENCE: 73
agtcggtgtc ctcagtggta                                                      20

<210> SEQ ID NO 74
<211> LENGTH: 20
<212> TYPE: DNA
<213> ORGANISM: ARTIFICIAL
<220> FEATURE:
<223> OTHER INFORMATION: primer

<400> SEQUENCE: 74
aagagcaggc tacaagtgct                                                      20

<210> SEQ ID NO 75
<211> LENGTH: 20
<212> TYPE: DNA
<213> ORGANISM: ARTIFICIAL
<220> FEATURE:
<223> OTHER INFORMATION: primer

<400> SEQUENCE: 75
gtggttttac gtggccgatt                                                      20

<210> SEQ ID NO 76
<211> LENGTH: 20
<212> TYPE: DNA
<213> ORGANISM: ARTIFICIAL
```

```
<220> FEATURE:
<223> OTHER INFORMATION: primer

<400> SEQUENCE: 76
gcctgacgtg aagtagcttt                                               20

<210> SEQ ID NO 77
<211> LENGTH: 20
<212> TYPE: DNA
<213> ORGANISM: ARTIFICIAL
<220> FEATURE:
<223> OTHER INFORMATION: primer

<400> SEQUENCE: 77
agtacccgac gagcgttatg                                               20

<210> SEQ ID NO 78
<211> LENGTH: 20
<212> TYPE: DNA
<213> ORGANISM: ARTIFICIAL
<220> FEATURE:
<223> OTHER INFORMATION: primer

<400> SEQUENCE: 78
aggctggtac agatgggtct                                               20

<210> SEQ ID NO 79
<211> LENGTH: 20
<212> TYPE: DNA
<213> ORGANISM: ARTIFICIAL
<220> FEATURE:
<223> OTHER INFORMATION: primer

<400> SEQUENCE: 79
ggagtttgca gtgagccaag                                               20

<210> SEQ ID NO 80
<211> LENGTH: 21
<212> TYPE: DNA
<213> ORGANISM: ARTIFICIAL
<220> FEATURE:
<223> OTHER INFORMATION: primer

<400> SEQUENCE: 80
acgaatcgag aaagagcctc a                                             21

<210> SEQ ID NO 81
<211> LENGTH: 21
<212> TYPE: DNA
<213> ORGANISM: ARTIFICIAL
<220> FEATURE:
<223> OTHER INFORMATION: primer

<400> SEQUENCE: 81
agtcggtgct tcattcactc t                                             21

<210> SEQ ID NO 82
<211> LENGTH: 18
<212> TYPE: DNA
<213> ORGANISM: ARTIFICIAL
<220> FEATURE:
<223> OTHER INFORMATION: primer

<400> SEQUENCE: 82
gccccgatgg gcgaataa                                                 18
```

```
<210> SEQ ID NO 83
<211> LENGTH: 20
<212> TYPE: DNA
<213> ORGANISM: ARTIFICIAL
<220> FEATURE:
<223> OTHER INFORMATION: primer

<400> SEQUENCE: 83
gggttgttgc actctctgga                                               20

<210> SEQ ID NO 84
<211> LENGTH: 20
<212> TYPE: DNA
<213> ORGANISM: ARTIFICIAL
<220> FEATURE:
<223> OTHER INFORMATION: primer

<400> SEQUENCE: 84
tcattctctg ccaaagcggt                                               20

<210> SEQ ID NO 85
<211> LENGTH: 20
<212> TYPE: DNA
<213> ORGANISM: ARTIFICIAL
<220> FEATURE:
<223> OTHER INFORMATION: primer

<400> SEQUENCE: 85
aaggtcttgc cgcagtgtaa                                               20

<210> SEQ ID NO 86
<211> LENGTH: 20
<212> TYPE: DNA
<213> ORGANISM: ARTIFICIAL
<220> FEATURE:
<223> OTHER INFORMATION: primer

<400> SEQUENCE: 86
caacgcctgc catattgtcc                                               20

<210> SEQ ID NO 87
<211> LENGTH: 20
<212> TYPE: DNA
<213> ORGANISM: ARTIFICIAL
<220> FEATURE:
<223> OTHER INFORMATION: primer

<400> SEQUENCE: 87
atggtagggt gttggtgctg                                               20

<210> SEQ ID NO 88
<211> LENGTH: 20
<212> TYPE: DNA
<213> ORGANISM: ARTIFICIAL
<220> FEATURE:
<223> OTHER INFORMATION: primer

<400> SEQUENCE: 88
cccagaaccc ctcgacaaaa                                               20

<210> SEQ ID NO 89
<211> LENGTH: 20
<212> TYPE: DNA
<213> ORGANISM: ARTIFICIAL
<220> FEATURE:
<223> OTHER INFORMATION: primer
```

```
<400> SEQUENCE: 89
tctcgcctct gactctgttc                                               20

<210> SEQ ID NO 90
<211> LENGTH: 20
<212> TYPE: DNA
<213> ORGANISM: ARTIFICIAL
<220> FEATURE:
<223> OTHER INFORMATION: primer

<400> SEQUENCE: 90
gaagagtcgg taaacaccgc                                               20

<210> SEQ ID NO 91
<211> LENGTH: 20
<212> TYPE: DNA
<213> ORGANISM: ARTIFICIAL
<220> FEATURE:
<223> OTHER INFORMATION: primer

<400> SEQUENCE: 91
ttacgcccgc aacaaaacag                                               20

<210> SEQ ID NO 92
<211> LENGTH: 20
<212> TYPE: DNA
<213> ORGANISM: ARTIFICIAL
<220> FEATURE:
<223> OTHER INFORMATION: primer

<400> SEQUENCE: 92
ccctccttcc ttcaaacgct                                               20

<210> SEQ ID NO 93
<211> LENGTH: 20
<212> TYPE: DNA
<213> ORGANISM: ARTIFICIAL
<220> FEATURE:
<223> OTHER INFORMATION: primer

<400> SEQUENCE: 93
ttccaccttt gcccgataca                                               20

<210> SEQ ID NO 94
<211> LENGTH: 20
<212> TYPE: DNA
<213> ORGANISM: ARTIFICIAL
<220> FEATURE:
<223> OTHER INFORMATION: primer

<400> SEQUENCE: 94
ggagatgggt acctaggggt                                               20

<210> SEQ ID NO 95
<211> LENGTH: 21
<212> TYPE: DNA
<213> ORGANISM: ARTIFICIAL
<220> FEATURE:
<223> OTHER INFORMATION: primer

<400> SEQUENCE: 95
gcttggcaac ttcagaaagc a                                             21

<210> SEQ ID NO 96
```

```
<211> LENGTH: 20
<212> TYPE: DNA
<213> ORGANISM: ARTIFICIAL
<220> FEATURE:
<223> OTHER INFORMATION: primer

<400> SEQUENCE: 96
agcagccggg tagtgtaaaa                                               20

<210> SEQ ID NO 97
<211> LENGTH: 20
<212> TYPE: DNA
<213> ORGANISM: ARTIFICIAL
<220> FEATURE:
<223> OTHER INFORMATION: primer

<400> SEQUENCE: 97
ccctactagc tcctcggaca                                               20

<210> SEQ ID NO 98
<211> LENGTH: 20
<212> TYPE: DNA
<213> ORGANISM: ARTIFICIAL
<220> FEATURE:
<223> OTHER INFORMATION: primer

<400> SEQUENCE: 98
acacatgcag cgtggtatct                                               20

<210> SEQ ID NO 99
<211> LENGTH: 20
<212> TYPE: DNA
<213> ORGANISM: ARTIFICIAL
<220> FEATURE:
<223> OTHER INFORMATION: primer

<400> SEQUENCE: 99
gtggacgagt agccagtgaa                                               20

<210> SEQ ID NO 100
<211> LENGTH: 21
<212> TYPE: DNA
<213> ORGANISM: ARTIFICIAL
<220> FEATURE:
<223> OTHER INFORMATION: primer

<400> SEQUENCE: 100
gcctctatca atgggcagac a                                             21

<210> SEQ ID NO 101
<211> LENGTH: 21
<212> TYPE: DNA
<213> ORGANISM: ARTIFICIAL
<220> FEATURE:
<223> OTHER INFORMATION: primer

<400> SEQUENCE: 101
ctcgtattcg cagcatagca a                                             21

<210> SEQ ID NO 102
<211> LENGTH: 24
<212> TYPE: DNA
<213> ORGANISM: ARTIFICIAL
<220> FEATURE:
<223> OTHER INFORMATION: primer

<400> SEQUENCE: 102
```
ttcaagttga taacggacta gcct                                              24

<210> SEQ ID NO 103
<211> LENGTH: 97
<212> TYPE: RNA
<213> ORGANISM: ARTIFICIAL
<220> FEATURE:
<223> OTHER INFORMATION: pRNA

<400> SEQUENCE: 103 cgauggluggc guuuugggg acaggugucc gugucgcgug ucgcgcgucg ccugggccgg         60 cggcguggguc ggugacgcga ccucccggcc ccgggga                                97

<210> SEQ ID NO 104
<211> LENGTH: 566
<212> TYPE: RNA
<213> ORGANISM: ARTIFICIAL
<220> FEATURE:
<223> OTHER INFORMATION: FALEC  ncRNA_a1

<400> SEQUENCE: 104
gcgcaucucc uacggccucc aggacagagg aaccggggga ggcaggggga aaaggccggc         60
ccagcaauuc cccuaccccc cggucccacg uguacccucc uggccugggu cgccccagcc       120
cacggggagc gggcggaguc cuggcccacg aagccuuguc accugcgggg cgaauccgca       180
agcggagacu ugucuuuaaa gggcuuuggg ccgggcgcgg uggcucaugc cuggaauccc       240
agcacuuugg gaggccgagg cgguggauca cgaggucagg aguucaagac cagccuggcc       300
aagaagcuca uacugacuaa ggcagcagaa cauacaggag gaagaggagc agguuucaca       360
gagggaagac augaguucaa uuuuggacuu cucaguaguc ggguccucca gugguagcaa       420
cuucaaacgg aagguguccaa aagucaaauu cuggagaguu gaguaugaau gggagaugaa       480
gaaaaggagg cagcacuugu agccugcucu uaauguauuu cugcacucua cacuagcagc       540
cuauuacaca ggacacuugg augucu                                            566

<210> SEQ ID NO 105
<211> LENGTH: 596
<212> TYPE: RNA
<213> ORGANISM: ARTIFICIAL
<220> FEATURE:
<223> OTHER INFORMATION: TRERNA1 ncRNA_a7

<400> SEQUENCE: 105
ccguuccugc cucccacaga caccuauuaa gugccuccag uuuuaggaac uggguauaga         60
uauggcuggg aacaaaaugg aagaaaacaa aaacaaaaau cccugcccuc auggugcuga       120
cucuccugug gcagagacgg agaagaugaa cagggauuuu auaccaggcg ucagaaggga       180
accagugcua aagaaaauga aaacaccagg ccgggagagg cagcuggcau gcgggccgug       240
gugguuuuac guggccgauu ugagagagug agacccccugg ggucuggag ccaggccugg       300 gaaaagcuac uucacgucag gccagggggcu guagcccugg caaccuccac uccgccugga       360
aauccuccac cucggggccu cucuuugccc agaccuggcc caggaggagc acugggagc        420 cgggaccuuc ccaacaauccc uugccguugg cuccacaaac cucagccagu ccugcaaccu      480
gggaugccuu uuccaccagg augccugcua cugucacugu ugcauuaga uaauuaauga       540 acuauaauua gaaaucauau caauaaaauu ucacagucua aggcuguuga aauagg           596

<210> SEQ ID NO 106

<211> LENGTH: 921
<212> TYPE: RNA
<213> ORGANISM: ARTIFICIAL
<220> FEATURE:
<223> OTHER INFORMATION: ncRNA_a3

<400> SEQUENCE: 106

```
gaaguugagc uucaggcgcg gcucuucccc gucacacugg gaccggacgc auuuccaugg      60
cguggaccca ggaaccucuc agagugaacu gaauuggaug caagaucacg gugcgucaga     120
gcuagcaaga uccuuaggau cauuuagccu gguuuacuaa uauuacacua uggaauuuaa     180
gcccaaggaa uggagaguac ccgacgagcg uuauguaagg agucgaguga aaguaagcu      240
ggaugcucug cuuggcuggc agguacagaa ugugccagac ccaucuguac cagccuggau     300
cucuugaggc aucagcacaa uggaccuggc cacaccaguu uauuccacac cgcugaggcu     360
ggucuuugag gaaucaccac acugucuucc acaaugcacc auggaauacu augcagacau     420
aaaaaggaau gagaucaugu cguuugcagg gacauggaug gagcuagaag ccauuauccu     480
cagaaaacua acacaggaac agaaaaccaa auaccacaug uucucacuua uaagugggag     540
cugaaugaug agaacacaug gacacguggu gcgggaacaa uacaccuggg gccuguugga     600
ggugggggc ugggaggagg gagagcauca agaauagcua augaggccag gcacaguggc     660
ucacgccugu aauccuagca uuuggggagg cugaggcggg cagaucauuu gaggucagga     720
guuugagacc agccuggcca auauggugaa accccgucuc uauuaaaaau acaaaaauau     780
uagccaggca ugguggcaau gcccguaguc ccugcaacuu gggaggcuga ggcaggagaa     840
ucguuugaac cugggaggug gaguuugcag ugagccaaga ucgcgccacu gcacuccagc     900
cugggcgaca gagugaggcu c                                              921
```

<210> SEQ ID NO 107
<211> LENGTH: 1461
<212> TYPE: RNA
<213> ORGANISM: ARTIFICIAL
<220> FEATURE:
<223> OTHER INFORMATION: RepA

<400> SEQUENCE: 107

```
cacucucuuu ucuauauuuu gcccaucggg gcugcggaua ccugguuuua uuauuuuuuc      60
uuugcccaac ggggccgugg auaccugccu uuuaauucuu uuuauuucgc ccaucggggc     120
cgcggauacc ugcuuuuuau uuuuuuuucc uuagcccauc gggguaucgg auaccugcug     180
auucccuucc ccucugaacc cccaacacuc uggcccaucg gggugacgga uaucugcuuu     240
uuaaaaauuu ucuuuuuuug gcccaucggg gcuucggaua ccugcuuuuu uuuuuuuuau     300
uuuuccuugc ccaucggggc cucggauacc ugcuuuaauu uuuguuuuuc uggcccaucg     360
gggccgcgga uaccugcuuu gauuuuuuuu uuucaucgcc caucgugcu uuuuauggau     420
gaaaaaaugu ugguuugug gguuguugca cucucuggaa uaucuacacu uuuuuuugcu     480
gcugaucauu ugguggugug ugagugguacc uaccgcuuug gcagagaaug acucugcagu     540
uaagcuaagg gcguguucag auuguggagg aaaaguggcc gccauuuuag acuugccgca     600
uaacucggcu uagggcuagu cguuugcgcu aguuaaacu agggaggcaa gauggaugau     660
agcaggucag gcagaggaag ucaugugcau ugcaugagcu aaaccuaucu gaaugaauug     720
auuuggggcu uguuaggagc uuucgcgau uguguaucg ggaggcagua agaaucaucu      780
uuuaucagua caagggacua guuaaaaaug gaagguuagg aaagacuaag gugcagggcu     840
uaaaaauggcg auuuugacau ugcggcauug cucagcaugg cgggcugugc uuuguuaggu     900
```

```
uguccaaaau ggcggaucca guucugucgc aguguucaag uggcgggaag gccacaucau    960
gaugggcgag gcuuuguuaa guggguuagca uggguggugga caugugcggu cacacaggaa  1020
aagauggcgg cugaaggucu ugccgcagug uaaaacaugg cgggccucuu ugucuuugcu   1080
gugugcuuuu cguguugggu uuugccgcag ggacaauaug gcaggcguug ucauauguau   1140
aucauggcuu uugucacgug gacaucaugg cgggcuugcc gcauuguuaa agauggcggg   1200
uuuugccgcc uagugccacg cagagcggga gaaaaggugg gauggacagu gcuggauugc   1260
ugcauaaccc aaccaauuag aaaugggggu ggaauugauc acagccaauu agagcagaag   1320
auggaauuag acugaugaca cacuguccag cuacucagcg aagaccuggg ugaauuagca   1380
uggcacuucg cagcugucuu uagccaguca ggagaaagaa guggaggggc cacguguaug   1440
ucucccagug ggcgguacac c                                             1461

<210> SEQ ID NO 108
<211> LENGTH: 4821
<212> TYPE: RNA
<213> ORGANISM: ARTIFICIAL
<220> FEATURE:
<223> OTHER INFORMATION: HOTTIP

<400> SEQUENCE: 108
guggggccca gacccgcgca accaggcggg gaggggaggu gggcgcgcga uuggguugcg     60
aucuggagca guggggacag gucaggaacc ggcgcguauu ucugcaguga gaccacagga   120
cggacaucgg cgccuucggc uucgauggag uugcgauuuu gcucuuucca gggaaacagu   180
ggcagggugu uugcugcuua ucgguuccug cggauaugcc ugggucccag gacauuccac   240
uggaggcuug gacugcauuu aggagccccu aucccuuccc uguccacacu guuagugagc   300
aauuucauau guuugcauuu agacccauag acucagaacg acucaucaca cacacacaca   360
guguacacug acacacucac auucgcacac uuagguauac agccugaucc uugcucugac   420
cugguaacaa cgcuuccucc uccagagacu uugagauaga gcgagcgauc ccugugcacc   480
auucauccau gcucccaccu cgccaguaug gcuggcuuag uucggaaggg gcuuaagag    540 gaacaagccc cagcugugcu ucuggcuggg acuuaaaccc cccuucuggg cccuaaagcc   600
acgcuucuuu guggaccgga ccugacucuc caggaaucug gaacccgcu auuucacucu    660 auuugggac aagaaaaagg ggcucuuugg ggccacuucc ugccuucccc ucaaguagga    720
ucuccagccu gcagagggug ccuaguccuu cuuugcccaa gaaccagucc aagaagccuu    780
uccucugugc cugggaaaug caaccuuuuc ugggagcau gguagggugu ggugcugaa    840 gaaccaagca gcgacccguc uuguagcugc cauguuuugu cgaggggu ugggggu ccu    900 gcugcuuuag agccacauac uuccacuccc ugauucacua cugugagcug ucagaugcc    960 uagaagagga caagcguuc aaagugaaag ugggcacauu accggaauag ugcuggggag   1020
agugcuggau ucuuuccac cccaggcgga cuggugagaa gccaggcuug gaccuguccu   1080
cugcuccuag cuugcacacu cagcccuaaa ucagagcag cacgcauacc accccucaca   1140
cacaccccac caucugcugu cuaaggcccc ugggcuuccu gcaggaucca gaccaaugug   1200
gcugggcuug ggcuuuuauc ugccugauc cuggauuugu ccugaccaau guaagugucg   1260
cccaauaaaa ccuucuauga ccccacaccc agccacccc ccaccaagug ugcccuuucc   1320
uucuugacuu uuuagcaguu cugggauaaau uugauuugc cccaguuua ccuucucccu   1380 gacuggccau uugcagacuc aggaacuagc cucuguaggg acuugauuuu ucuguuacuu   1440
```

-continued

```
ucuggccguu ucaccacccc ccuuccuccc uccaaguggc auuguaaaac ucacagugac   1500
aaagagacag aguagggeuc uaggccccug uuccugggga cuugaaggcg guuuuacaua   1560
cuggucagac acggcuggag gccaagguca aguugaaagu gcaguccag ccagcaugag    1620 aacugccaug cgagcguaga gacacaggca gcagcaaaag gcccauugcc cacauccccu   1680
cacucuuaau uuucucucuc uuuuuaaaau ucucgccucu gacucuguuc ggcugccag    1740 aauuuuuugg ugccuucgug ggguuuuugg ggcgguguuu accgacucuu cucugccucc   1800
gcccugcuca gccagggcuu ugagccucuu cgguuuuccg gccagacccg gaaaaacgaa   1860
aacacagcuu ggggagcccc cacuagccgg cgccugugcc agcucaccuc uggccauggc   1920
gcagcugccg gugcacacgg cggccaaggc cagcccaca uucuuccccuc ccccucccac    1980 uucaccguag ccccgaaccc ugcgcgcaga gaaagggucu cagcuccaca gacgacuggg   2040
ucccuccuca ccaaaaaugg ugagacaaga uuucaucugu cggccgagga gccacaagca   2100
gguaccacaa agccacuagu gcacagggac ucagaaaaga cggcaggagc ccaaggaaaa   2160
cuccaauuug aguacagccc ugccuuguuu cccccagaga gucccugagc aaggagaccu   2220
ccaccccaca cacaccauuu cagaacaacc agguuccaga cucccaugag gagcaucucc   2280
cacugcagag ccuuggccag ccgcgcccgg acuccacaga gcuggcgcaa acuccgccuc   2340
ccaaaacucg gcucugggag gccuaaguga cuccgaagcc ggcggcagcc gcggcagcgg   2400
ccguggucgu ggaagagcuc uuuucccga cagugccacu gaucgcucuu cacuggagcu    2460
ggaaacagcc uucgcggaaa ggaccggagc augcguuaga agcagaggga gcuuggugaa   2520
gggcucggcu ggaaggagga aacgccuucu cgcagugcgc ggccagcccg cgggggacac   2580
cggcuugcug gacugcaggg gcccgugcca ccaggaagu gaccugcggg ucacucagcc     2640
ggggcgcugg gcgagcgcgg gacggcccgg agaauuccgu gcggcugcga cgggaaaagg   2700 acgaggggc ucuguacccg acgcugccac uggcccaaag gaauuuuacc cgcgagcgcc    2760
caccccaccc uagcuugaug cuuacgcccg caacaaaaca ggaaaccagg acugggcagu   2820
gcauucuuua agucaacaaa uacacugaag acuucgagcg uuugaaggaa ggaggggguu   2880
ugcacguaag ccuggccccg ccgggcucgg cuuucucgcu gagaaagcgg cgcaggcagc   2940
caggcggccu gggcccgcgg ggguccaucu cgcccuagac uccuaagaac ucccacggcc   3000
cuguucccag cugcgaauuc uuaaugcaca acgcgacgga gggaaggaaa uuccagcg    3060 cagcgacgag gaagggaac ucaggaccc uucaaguaca cacugaggug ugaucagagu     3120
uuuaugggca cuuuauaugc uguaaucaua acgaugugug ugccuugaua ugcacgcaua   3180
uucacgcauc aaacgugcau acacacacag agugaaugug cgcauccaau gucauggg     3240 ugaaauacaa gcaucauacc cagcccuacg aaaaaaaaau ucaccuguc ggaccaggcu    3300 ggugacauac uucgcuggcg caucccuua cucacucuua cuuuuccgac cccucaccau    3360
ucccucuccu guggcuuggu aaauacaccu gcccuccgug gaaggugagu ccuggacugg   3420
cguugccagg uucgcaugue cucccagaa ccuccgucug gcuccaggga cucucacuga    3480
gcgggucuag agcacccagc acuuuucaag gaacagccgc gguuccuuug ucccgcggcu   3540
ccagccccgu ucgcccagc ucucaggaa acgaagcgcu caguaagaac uuuugauauu     3600
aguuuguaug ggauuuuaca cucuggugag gggagcugag uacggaaguu ccauuaauca   3660
uacuccaacc uuggguuuag auauucaguu uaugggguugg gagagggagu uugccggaaa  3720
gaaagcauca agguuggccg cugacuccag agaaaugaaa agggagcaag gucguuuucu   3780
guuucuggaa aucaagaauu aggaaugggc aacuacaggu gcuaaccaac agaccacuuu   3840
```

| | |
|---|---|
| uuuguuuuuu ggusgcccuu uggcagggau aguuuuucca ccuuugcccg auacaauuua | 3900 |
| aaaaaaaaaa uccuuuuauu auggaauuug ucaaacacac acacaagcau aacaaacccc | 3960 |
| uagguaccca ucuccaaguu uugacccua uuauaauuuc aucuucagug uuuuauuauc | 4020 |
| cacuccucu cucucuaucu uuaguauuuu aaaguaaauc ccagauagca ucaucauu | 4080 |
| ucaccccac cauaggauuu caaagaucug uuauauuuca agauugagua aaagggcuug | 4140 |
| aaauggguu auugcaauga aacucuagaa aaagcuugag gguucaccca ggaguaagcu | 4200 |
| ggacaaaaaa gggguuugag ggguggaccc aucuugccua aaaaucuugu cucaucuuuc | 4260 |
| uaaaaauuac auaugaaaga ggaagauuua uguuacuuuu uuauaugaga gaaucguccu | 4320 |
| uuaauagaaa auuucuauug cugcaucaga auuauggagg aacacaaaaa acauaccuca | 4380 |
| guccuuagug uguccuaaau uaacacauau ucacuuauua guggguaaau gacuauauuu | 4440 |
| cauuucagca caacuucucc ccugguagaa acacaaaaga aauuucuaau gauuaaacua | 4500 |
| ggaaaguuug cacugaauug auggcuuauc agagcaaccg caguuuucag gaagaaauuc | 4560 |
| aaugccaugc guugaaaaua uccccuagc aauaagggau uauuuuaaa aagaaugaa | 4620 |
| uaaagauguu cugguucu uuguuuaau cgguagucu cauuuacaac gagcaugauu | 4680 |
| cucccugucg aacucugaaa gugacuuaac ugaaggcuu ggcaacuuca gaaagcaaaa | 4740 |
| agguaaaac agaaauagc acacggguuga auugacaac uuuuacacua cccggcugcu | 4800 |
| uaauaaauuc uaaccccacu u | 4821 |

```
<210> SEQ ID NO 109
<211> LENGTH: 130
<212> TYPE: DNA
<213> ORGANISM: ARTIFICIAL
<220> FEATURE:
<223> OTHER INFORMATION: insertion construct

<400> SEQUENCE: 109
```

| | |
|---|---|
| gaucuagaua cgacucacua uguuuaagag cuaugcugcg aauacgagcu cguauucgca | 60 |
| gcauagcaag uuuaaauaag gcuaguccgu uaucaacuug aaaaaguggc accgagucgg | 120 |
| ugcuuuuuuu | 130 |

```
<210> SEQ ID NO 110
<211> LENGTH: 25
<212> TYPE: DNA
<213> ORGANISM: ARTIFICIAL
<220> FEATURE:
<223> OTHER INFORMATION: insertion construct

<400> SEQUENCE: 110
```

| | |
|---|---|
| ggagcagacg auauggcguc gctcc | 25 |

```
<210> SEQ ID NO 111
<211> LENGTH: 43
<212> TYPE: RNA
<213> ORGANISM: ARTIFICIAL
<220> FEATURE:
<223> OTHER INFORMATION: insertion construct

<400> SEQUENCE: 111
```

| | |
|---|---|
| ccgaccagaa ucaugcaagu gcguaagaua gucgcgggcc ggc | 43 |

```
<210> SEQ ID NO 112
<211> LENGTH: 63
<212> TYPE: RNA
```

```
<213> ORGANISM: ARTIFICIAL
<220> FEATURE:
<223> OTHER INFORMATION: insertion construct

<400> SEQUENCE: 112
cguacaccau caggguacgu cucagacacc aucagggucu gucugguaca gcaucagcgu    60
acc                                                                 63

<210> SEQ ID NO 113
<211> LENGTH: 67
<212> TYPE: RNA
<213> ORGANISM: ARTIFICIAL
<220> FEATURE:
<223> OTHER INFORMATION: insertion construct

<400> SEQUENCE: 113
ucuuacugcu guauaagcag cucuuacugc cguguaggca gcuucuacuu cuguauaaga    60
agcuuuc                                                             67

<210> SEQ ID NO 114
<211> LENGTH: 81
<212> TYPE: RNA
<213> ORGANISM: ARTIFICIAL
<220> FEATURE:
<223> OTHER INFORMATION: insertion construct

<400> SEQUENCE: 114
ggagcagacg auauggcguc gcuccucucc acgagagcau augggcuccg uggucuccag    60
cagacgauau ggcgucgcug g                                             81

<210> SEQ ID NO 115
<211> LENGTH: 83
<212> TYPE: RNA
<213> ORGANISM: ARTIFICIAL
<220> FEATURE:
<223> OTHER INFORMATION: insertion construct

<400> SEQUENCE: 115
gcuucuggac ugcgauggga gcacgaaacg ucguggcgca auugguggg gaaaguccuu     60 aaaagagggc caccacagaa gcc                                           83

<210> SEQ ID NO 116
<211> LENGTH: 95
<212> TYPE: RNA
<213> ORGANISM: ARTIFICIAL
<220> FEATURE:
<223> OTHER INFORMATION: insertion construct

<400> SEQUENCE: 116
gauguaacug aaugaaaugg ugaaggacgg guccaguagg cugcuucggc agccuacuug    60
uugaguagag ugugagcucc guaacuaguu acauc                              95

<210> SEQ ID NO 117
<211> LENGTH: 99
<212> TYPE: RNA
<213> ORGANISM: ARTIFICIAL
<220> FEATURE:
<223> OTHER INFORMATION: insertion construct

<400> SEQUENCE: 117
ucugcucccg ugauggcgaa agccugagga gcucucuggc cgugauggcg aaagccugag    60
ccagucucug cccgugaugg cgaaagccug aggcagucu                          99
```

```
<210> SEQ ID NO 118
<211> LENGTH: 129
<212> TYPE: RNA
<213> ORGANISM: ARTIFICIAL
<220> FEATURE:
<223> OTHER INFORMATION: insertion construct

<400> SEQUENCE: 118
aaggacgggu ccggacgcaa ggacggaucc gaccgaaagg acggguccaa uggaggaaac      60
accauuguug aguagagugu gagucggucg uugaguagag ugugaggcgu ccguugagua     120
gagugugag                                                             129

<210> SEQ ID NO 119
<211> LENGTH: 137
<212> TYPE: RNA
<213> ORGANISM: ARTIFICIAL
<220> FEATURE:
<223> OTHER INFORMATION: insertion construct

<400> SEQUENCE: 119
ggagcagacg auauggcguc gcuccucucc acgagagcau augggcuccg uggucugcag      60
cagacgauau ggcgucgcug cucucguaga ugccauaugg ggcacuacgu cuccagcaga     120
cgauauggcg ucgcugg                                                    137

<210> SEQ ID NO 120
<211> LENGTH: 247
<212> TYPE: RNA
<213> ORGANISM: ARTIFICIAL
<220> FEATURE:
<223> OTHER INFORMATION: insertion construct

<400> SEQUENCE: 120
ucuggaauug cgggaaaggg gucaacagcc guucaguacc aagucucagg ggaaacuuug      60
agauggccuu gcaaagggua ugguaauaag cugacggaca uggccuaac acgcagccaa     120 guccuaaguc aacagucugg agcagacgau auggcgucgc uccucuccac gagagcauau    180
gggcuccgug gucuccagca gacgauaugg cgucgcuggu cucuguugau auggaugcag    240
uucaucu                                                              247

<210> SEQ ID NO 121
<211> LENGTH: 18
<212> TYPE: DNA
<213> ORGANISM: ARTIFICIAL
<220> FEATURE:
<223> OTHER INFORMATION: primer

<400> SEQUENCE: 121
cgactcggtg ccactttt                                                    18

<210> SEQ ID NO 122
<211> LENGTH: 85
<212> TYPE: DNA
<213> ORGANISM: ARTIFICIAL
<220> FEATURE:
<223> OTHER INFORMATION: primer
<220> FEATURE:
<221> NAME/KEY: misc_feature
<222> LOCATION: (25)..(30)
<223> OTHER INFORMATION: nnnnnn corresponds to IlluminA indexes 1 to 7

<400> SEQUENCE: 122
```

```
caagcagaag acggcatacg agatnnnnnn gtgactggag ttcagacgtg tgctcttccg    60
atcttcaagt tgataacgga ctagc                                         85

<210> SEQ ID NO 123
<211> LENGTH: 78
<212> TYPE: DNA
<213> ORGANISM: ARTIFICIAL
<220> FEATURE:
<223> OTHER INFORMATION: primer

<400> SEQUENCE: 123
aatgatacgg cgaccaccga gatctacact ctttccctac acgacgctct tccgatctag    60
ctatgctgcg aatacgag                                                 78
```